(12) United States Patent
Kaplan et al.

(10) Patent No.: US 10,689,712 B2
(45) Date of Patent: *Jun. 23, 2020

(54) COMPOSITIONS AND METHODS FOR DETECTING NUCLEIC ACID FROM MOLLICUTES

(71) Applicant: Gen-Probe Incorporated, San Diego, CA (US)

(72) Inventors: Shannon K. Kaplan, San Diego, CA (US); Kristin W. Livezey, San Diego, CA (US); Michael M. Becker, San Diego, CA (US); James J. Hogan, Coronado, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 21 days.

This patent is subject to a terminal disclaimer.

(21) Appl. No.: 15/699,502

(22) Filed: Sep. 8, 2017

(65) Prior Publication Data

US 2018/0073059 A1 Mar. 15, 2018

Related U.S. Application Data

(63) Continuation of application No. 14/938,630, filed on Nov. 11, 2015, now Pat. No. 9,920,382, which is a continuation of application No. 12/821,608, filed on Jun. 23, 2010, now Pat. No. 9,212,397.

(60) Provisional application No. 61/219,674, filed on Jun. 23, 2009.

(51) Int. Cl.
*C12Q 1/68* (2018.01)
*C12Q 1/689* (2018.01)

(52) U.S. Cl.
CPC ......... *C12Q 1/689* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 5,693,467 A * | 12/1997 | Roblin, III | C12Q 1/689 435/6.12 |
| 5,851,767 A | 12/1998 | Stanbridge et al. | |
| 5,969,122 A | 10/1999 | Hammond et al. | |
| 6,074,826 A | 6/2000 | Hogan et al. | |
| 6,150,517 A | 11/2000 | Hogan et al. | |
| 6,261,769 B1 | 7/2001 | Everett et al. | |
| 6,677,153 B2 | 1/2004 | Iversen | |
| 6,720,139 B1 | 4/2004 | Zyskind et al. | |
| 6,821,770 B1 | 11/2004 | Hogan | |
| 7,018,794 B2 | 3/2006 | Berka et al. | |
| 7,214,780 B2 | 5/2007 | Cunningham et al. | |
| 7,238,675 B2 | 7/2007 | Iversen | |
| 7,341,835 B2 | 3/2008 | Blume et al. | |
| 7,345,155 B2 | 3/2008 | Cunningham et al. | |
| 7,361,470 B2 | 4/2008 | Kelley et al. | |
| 7,449,328 B2 | 11/2008 | Hogan | |
| 7,504,493 B2 | 3/2009 | Velculescu et al. | |
| 9,212,397 B2 * | 12/2015 | Kaplan | C12Q 1/689 |
| 2003/0175709 A1 | 9/2003 | Murphy et al. | |
| 2005/0250112 A1 | 11/2005 | Padmabandu et al. | |
| 2006/0046265 A1 | 3/2006 | Becker et al. | |
| 2006/0252081 A1 * | 11/2006 | Hyldig-Nielsen | C12Q 1/6816 435/5 |
| 2007/0112277 A1 | 5/2007 | Fischer et al. | |
| 2007/0275378 A1 | 11/2007 | Werner | |
| 2008/0138808 A1 | 6/2008 | Hall et al. | |
| 2008/0187916 A1 | 8/2008 | Ikonomi et al. | |
| 2008/0233570 A1 | 9/2008 | Hall | |
| 2008/0311558 A1 | 12/2008 | Ecker et al. | |
| 2010/0323362 A1 * | 12/2010 | Kaplan | C12Q 1/689 435/6.12 |
| 2011/0189687 A1 * | 8/2011 | Sampath | C12Q 1/6858 435/6.15 |
| 2016/0060685 A1 | 3/2016 | Kaplan et al. | |

FOREIGN PATENT DOCUMENTS

| | | |
|---|---|---|
| EP | 2 028 273 A1 | 2/2009 |
| EP | 2 446 057 B1 | 11/2014 |
| WO | 90/15157 A1 | 12/1990 |
| WO | 96/37177 A2 | 11/1996 |
| WO | 00/036142 A1 | 6/2000 |
| WO | 05/003384 A1 | 1/2005 |

(Continued)

OTHER PUBLICATIONS

USPTO Notice of Allowance and Examiner Initiated Interview Summary, U.S. Appl. No. 14/938,630, dated Nov. 13, 2017.
EPO Communication Pursuant to Article 94(3) EPC, European Patent Application No. 14188675.4, dated Nov. 23, 2017.
Grondahl et al., "Rapid Identification of Nine Microorganisms Causing Acute Respiratory Tract Infections by Single-Tube Multiplex Reverse Transcription-PCR: Feasibility Study," J. Clin. Microbial., Jan. 1999, pp. 1-7, vol. 37(1), American Society for Microbiology, Washington, D.C.
Layani-Milon et al., "Incidence of Upper Respiratory Tract Mycoplasma pneumonia Infections among Outpatients in Rhône-Alpes, France, during Five Successive Winter Periods," J. Clin. Microbiol., Jun. 1999, pp. 1721-1726, vol. 36(6), American Society for Microbiology, Washington, D.C.

(Continued)

*Primary Examiner* — Gary Benzion
*Assistant Examiner* — Olayinka A Oyeyemi
(74) *Attorney, Agent, or Firm* — Alston & Bird LLP

(57) ABSTRACT

Compositions, reaction mixtures, kits and methods used in amplifying and detecting nucleic acids from various species of the class Mollicutes. Particular regions of the 23S rRNA or its gene have been identified as preferred targets for nucleic acid amplification reactions of a sample suspected containing at least one species of Mollicutes. Some oligomers comprise tag regions, target closing regions, promoter sequences, and/or binding moieties. Samples can be from any source suspected of containing a species of the class Mollicutes. Preferred sample sources include bioreactors, cell lines, cell culture wares and pharmaceutical manufacturing wares.

21 Claims, No Drawings

Specification includes a Sequence Listing.

(56) References Cited

FOREIGN PATENT DOCUMENTS

| WO | 2006/025672 A1 | 3/2006 |
|---|---|---|
| WO | 06/126040 A1 | 11/2006 |
| WO | 08/080029 A2 | 7/2008 |

OTHER PUBLICATIONS

Kong et al., "Species-Specific PCR for Identification of Common Contaminant Mollicutes in Cell Culture," J. Clin. Microbial., Jul. 2001, pp. 3195-3200, vol. 67(7), American Society for Microbiology, Washington, D.C.

Eldering et al., "Development of a PCR method for Mycoplasma testing of Chinese hamster ovary cell cultures used in the manufacture of recombinant therapeutic proteins," Biologicals 32, 2004, pp. 183-193, Elsevier Science Ltd., London, UK.

Sung et al., "PCR-Based Detection of Mycoplasma Species," J. Microbiol., 2006, pp. 42-49, vol. 44(1), The Microbiological Society of Korea.

Volokhov et al., "Sequencing of the intergenic 16S-23S rRNA spacer (ITS) region of Mollicutes species and their identification using microarray-based assay and DNA sequencing," Appl. Microbiol. Biotechnology, Feb. 2006, 71(5):680-698, Springer, Berlin, DE.

Hardick et al., "Performance of the Gen-Probe Transmission-Mediated Amplification Research Assay Compared to That of a Multitarget Real-Time PCR for Mycoplasma genitalium Detection," J. Clin. Microbial., Apr. 2006, pp. 1236-1240, vol. 44(4), American Society for Microbiology, Washington, D.C.

EBI Database Accession No. L08897, "Mycoplasma gallisepticum (strain A5969) 16S-, 23S-, 5S ribosomal RNA (rrsA, rrlA, rrfA) genes," Jan. 26, 1993 [Retrieved from the Internet Aug. 18, 2010: <http://ibis/IBIS/exam/dbfetch.jsp?id=EM_PRO:L08897>] XP-002597075.

EBI Database Accession No. AF443616, "Mycoplasma hominis DNA-dependent RNA polymerase alpha chain gene, partial cds; 50S ribosomal protein L17 and 50S ribosomal protein L17 and 50S ribosomal protein L32 genes, complete cds; rrnA operon, complete sequence, 50S ribosomal protein L10 and 50S ribosomal protein L7/L12 genes, complete cds; and DNA-dependent RNA polymerase," Sep. 26, 2002 [Retrieved from the Internet Aug. 18, 2010: <http://ibis/IBIS/exam/dbfetch.jsp?id=EM_PRO:AF443616>] XP-002597076.

EBI Database Accession No. EU582532, "Spiroplasma insolitum strain M55 23S ribosomal RNA gene, partial sequence; 23S-5S ribosomal intergentic spacer, complete sequence, and 5S ribosomal RNA gene, partial sequence," Apr. 13, 2008 [Retrieved from the Internet Aug. 18, 2010: <http://ibis/IBIS/exam/dbfetch.jsp?id=EM_PRO:EU582532>] XP-002597077.

International Search Report and Written Opinion of the International Searching Authority, PCT Patent Application PCT/US2010/039592 dated Aug. 30, 2010.

"Mycoplasma Detection Polymerase Chain Reaction Kit (16S rRNA gene), Technical Bulletin," Clongen Laboratories, LLC. [Retrieved from the Internet Mar. 14, 2011: <http://replay.waybackmachine.org/20080609041545/http://clongen.com/product_detail.php?prod_id=120&PHPSESSID=b982cdf18dba34e5a73aaf235696731b].

"Mycoplasma Testing—An Overview," Clongen Laboratories, LLC. [Retrieved from the Internet Mar. 14, 2011: <http://replay.waybackmachine.org/200800305033312/http://clongen.com/mycoplasma_testing.php].

"MicroSEQ Mycoplasma Detection Assay," Product Bulletin, Applied Biosystems. [Retrieved from the Internet Mar. 14, 2011: Applied Biosystems, Foster City, CA].

Brown et al., "Assay Validation for Rapid Detection of Mycoplasma Contamination," BioProcess International, Apr. 2009, pp. 30-40, vol. 7(4), BioProcess International, Westborough, MA.

Florentini, "Mycoplasma: Effective Detection and Treatment," Technical Resources, May 18, 2009, Biological Industries Israel Beit-Haemek Ltd., Israel (http://www.bioind.com/HTMLs/print.aspx?C2004=12573&BSP=12570).

APO Notice of Acceptance, Australian Patent Application No. 2010264468, dated Jan. 6, 2015.

CIPO Office Action, Canadian Patent Application No. 2,768,768, dated Jul. 8, 2015.

EPO International Preliminary Report on Patentability and ritten Opinion of the International Searching Authority, PCT Patent Application PCT/US2010/039592 dated Jan. 12, 2012.

EPO Exam Report, European Patent Application No. 10729011.6, dated Oct. 4, 2013.

EPO Decision to Grant, European Patent Application No. 10729011.6, dated Jun. 4, 2014.

EPO Extended Search Report, European Patent Application No. 14188675.4, dated Jan. 7, 2015.

USPTO, Office Action, U.S. Appl. No. 12/821,608, dated Mar. 21, 2012.

USPTO, Final Office Action, U.S. Appl. No. 12/821,608, dated Jul. 13, 2012.

USPTO, Office Action, U.S. Appl. No. 12/821,608, dated Jul. 24, 2014.

USPTO, Final Office Action, U.S. Appl. No. 12/821,608, dated Jan. 28, 2015.

USPTO, Notice of Allowance, U.S. Appl. No. 12/821,608, dated Jul. 16, 2015.

Furneri et al., "Two New Point Mutations at A2062 Associated with Resistance to 16-Membered Macrolide Antibiotics in Mutant Strains of Mycoplasma hominis," Antimicrob. Agents Chemother., 2001, 45(10):2958-2960, Am. Society for Microbiology, Washington, D.C., U.S.A.

Kong et al., "Postgenomic taxonomy of human ureaplasmas—a case study based on multiple gene sequences,", Int. J. Syst. Evol. Microbial., 2004, 54:1815-1821, Microbiology Soc. United Kingdom.

Lowe et al., "A computer program for selection of oligonucleotide primers for polymerase chain reactions," Nucleic Acids Res., 1990,18(7):1757-1761, Oxford University Press, Oxford, United Kingdom.

Westberg et al., The Genome Sequence of *Mycoplasma mycoides* subsp. mycoides SC Type Strain PC1 T, the Causative Agent of Contagious Bovine Pleuropneumonia (CBPP), Genome Res., 2004, 14:221-227, Cold Spring Harbor Laboratory Press, USA.

Nucleic acid sequence search reports: AC. AF317663, AF272616, AF272615, BX293980.2 and AR493523.

EPO, Acknowledgment of Receipt, European Patent Application No. 10729011.6, dated Jan. 23, 2012, (2 pp.).

EPO, Entry into the European Phase, European Patent Application No. 10729011.6, dated Jan. 23, 2012, (217 pp.).

EPO, Communication Pursuant to Rules 161(1) and 162 EPC, European Patent Application No. 10729011.6, dated Feb. 2, 2012, (2 pp.).

EPO, Reply to Rule 161(1) and 162 Communication, European Patent Application No. 10729011.6, dated Feb. 2, 2012, Jun. 8, 2012, (20 pp.).

EPO, Communication Pursuant to Rules 94(3) EPC, European Patent Application No. 10729011.6, dated Oct. 4, 2013, (5 pp.).

EPO, Reply to Article 94(3) EPC Communication, European Patent Application No. 10729011.6, dated Jan. 29, 2014, (12 pp.).

EPO, Communication under Rule 71(3) EPC, European Patent Application No. 10729011.6, dated Apr. 6, 2014, (123 pp.).

EPO, Decision to Grant a European Patent Pursuant to Article 97(1) EPC, European Patent Application No. 10729011.6, dated Oct. 23, 2014, (2 pp.).

EPO, Communication regarding the expiry of the time limit within which Notice of Opposition may be filed, European Patent Application No. 10729011.6, dated Sep. 23, 2016, (1 pg.).

Bi et al., "Phylogenetic analysis of Sprioplasmas from three freshwater crustaceans (Eriocheir sinensis, Procambarus clarkia and Penaeus vannamei) in China," J. Invertbr. Pathol. 2008, 99:57-58, Elsevier Inc.

Nucleic acid sequence search reports: CP000896, CP000123.

APO Examination Report No. 1, Australian Patent Application No. 2010264468, dated Jun. 30, 2014.

CIPO Office Action, Canadian Patent Application No. 2,768,768, dated Nov. 22, 2016.

(56) References Cited

OTHER PUBLICATIONS

USPTO Non-Final Rejection, U.S. Appl. No. 14/938,630, dated Jul. 15, 2016.
USPTO Non-Final Rejection, U.S. Appl. No. 14/938,630, dated Jan. 30, 2017.
USPTO Notice of Allowance and Examiner-Initiated Interview Summary U.S. Appl. No. 14/938,630, dated May 19, 2017 and May 12, 2017 (respectively).
EPO Communication Pursuant to Article 94(3) EPC, U.S. Patent Application No. 14188675.4, dated Nov. 18, 2016.

* cited by examiner

SEQUENCE LISTING

<160> NUMBER OF SEQ ID NOS: 77

<210> SEQ ID NO 1
<211> LENGTH: 10244
<212> TYPE: DNA
<213> ORGANISM: Mycoplasma hominis AF443616.3 GI:110815963

<400> SEQUENCE: 1

```
tctagaatat ggtccaaaat tagaatcaaa aatcaaaaat ggtcaattt tagcaatgga       60 tagtgacttc agtcctatta aaaagttgc gatttatt gaagaattaa attctacttc       120
taacataatt gaagaaagat taaaaattaa agttgaaacc gatggaactg ttgaagctaa       180
aaacgttatg gaagaagcag caaagattat agttgctcat ttccaaatca ttggaaacat       240
tgacgcatta ggaacaattg atttattcga tgatcaaaaa gaaaaacatg aaaaaactcc       300
aaaagtttca gtttctattg ataaattgaa tttgacaatt cgttcattga atgccttaag       360
acgtgctgga tttaataatg ttgatgaaat aatgaaatta agcgatgaag aactttcaaa       420
tattaaaaat ttgggtaaaa aatcagtaca agatattatt gaccgtcgta gagaatgact       480
tgatagtcaa ttaaataatg aagattctaa caaagaatat gctgctaacg aagaaggaga       540
ataacaatgg caaatccaaa acaactattt cgtagaaata ctgagtgatg agaccacgtt       600
gaaagatcac ttgtaacaga tttattgatt aatggcaaag taacaaccac attagaacgt       660
gctaaaagaa ttcgttcaaa tgcagaaaaa atgattactc taggtaagaa aaatacccta       720
gcttcgcgta gacaagcagc caaatattta agattaattg caacagaaaa caaaaataaa       780
aattcattac aatatttatt tgatgttgtg gcaccaaaat acgttgaacg taatggtgga       840
tatacaagaa ttacaaaatt agccaatcgt gctggtgata atgctaaaat ggcaataatc       900
gaattggtat aatttgatta tttaaaggag aaagttatgg cagtagtacc aaaaagaaaa       960
acttcaaaac aaagaaaaca tttaagaaga tcacaccacg ctctagtggc tccaacatta      1020
gttgaatgtt cacaatgtaa gaatttaatt actcctcacc aagcatgtga aaactgcggt      1080
ttttatagag gaagaaaagt tattaaagaa gcaattaacg ataaaattaa ataatattaa      1140
ataataaaaa attctcttga tttattcgag agaatttta tttatcaaac tcttcaattt      1200
aaaaaaaata aataattaaa ttactaataa gtaattatga agcatttctt aaaaaatata      1260
taagcaaata aaaaaatatc tatttttac aaaaaaaatt aattaaagtt atataataaa      1320
tcaagcaatt ttgattgcta aaaacttat aaaaaaacaa acaataaaat aaatttattt      1380
ttttatttat aatcaaccaa ttcaaattt ttataagagt ttgatcctgg ctcaggatga      1440
acgctggctg tgtgcctaat acatgcatgt cgagcgaggt tagcaataac ctagcggcga      1500
atgggtgagt aacacgtgct taatctacct tttagattgg aatacccatt ggaaacaatg      1560
gctaatgccg gatacgcatg gaaccgcatg gttccgttgt gaaaggcgct gtaaggcgcc      1620
actaaaagat gagggtgcgg aacattagtt agttggtgag gtaatggccc accaagacta      1680
tgatgtttag ccgggtcgag agactgaacg gccacattgg gactgagata cggcccaaac      1740
tcctacggga ggcagcagta gggaatattc cacaatgagc gaaagcttga tggagcgaca      1800
cagcgtgcac gatgaaggtc ttcggattgt aaagtgctgt tataagggaa gaacatttgc      1860
aataggaaat gattgcagac tgacggtacc ttgtcagaaa gcgatggcta actatgtgcc      1920
```

```
agcagccgcg gtaatacata ggtcgcaagc gttatccgga attattgggc gtaaagcgtt    1980
cgtaggctgt ttgttaagtc tggagttaaa tcccggggct caaccccggc tcgctttgga    2040
tactagcaaa ctagagttag atagaggtaa gcggaattcc atgtgaagcg gtgaaatgcg    2100
tagatatatg gaagaacacc aaaggcgaag gcagcttact gggtctatac tgacgctgag    2160
ggacgaaagc gtggggagca acaggatta gatacctgg tagtccacgc cgtaaacgat      2220
gatcattagt cggtggagaa tcactgacgc agctaacgca ttaaatgatc cgcctgagta    2280
gtatgctcgc aagagtgaaa cttaaaggaa ttgacgggga cccgcacaag cggtggagca    2340
tgtggtttaa tttgaagata cacggaaaac cttacccact cttgacatcc ttcgcaaagc    2400
tatagagata tagtggaggt tatcggagtg acagatggtg catggttgtc gtcagctcgt    2460
gtcgtgagat gtttggtcaa gtcctgcaac gagcgcaacc cctatcttta gttactaaca    2520
ttaagttgag gactctagag atactgcctg gtaactggg aggaaggtgg ggatgacgtc     2580
aaatcatcat gcctcttacg agtggggcca cacacgtgct acaatggtcg gtacaaagag    2640
aagcaatatg gcgacatgga gcaaatctca aaaagccgat ctcagttcgg attggagtct    2700
gcaattcgac tccatgaagt cggaatcgct agtaatcgca gatcagctat gctgcggtga    2760
atacgttctc gggtcttgta cacaccgccc gtcacaccat gggagctggt aatacccaaa    2820
gtcggtttgc taacctcgga ggcgaccgcc taaggtagga ctggtgactg gggtgaagtc    2880
gtaacaaggt atccctacga gaacgtgggg atggatcacc tcctttctac ggagtacaac    2940
ctacgttatg gaaaaaaaat atttgtatcc agttttgaga gatttatctc tcggttcttt    3000
gaaaactgaa tatcgacatt gatatattaa ttaatatttc aaagtttaga tcaaccatag    3060
aatatttata ttttataaga caaacaatag gtcatacaat taacaaaact attaaacaag    3120
caagagtttt tggtggatgc cttgggtctg gaagtcgatg aaggacgtga ttacctgcga    3180
taagcctcgg ttagctggaa ataagctgtt atccggggat ttccgaatgg ggaaacctaa    3240
ttgagctaat cctcaattat catatcgatg aattcatagt cgaatgaaga gacacgctgt    3300
gaattgaaac atctcagtag cagcaggaag agaaaataaa gaatgattcc ctaagtagtg    3360
gcgagcgaac ggggaagagc ccaaaccaac acatgttgtt ggggttgtag gactgcgaca    3420
tggattaatg aatttgtaca tagcagaata agttggaacg cttaaacata gagggtgaaa    3480
ttcccgtaag cgaaatgtat aaatctccta gcagtatcct gagtagggcg gggcacgtga    3540
aaccctgtct gaatttgccg ggaccacccg gtaaggctaa atactaacca gacaccgata    3600
gtgaactagt accgtgaggg aaaggtgaaa agaaccccgg gaggggagtg aaatagattc    3660
tgaaaccaat tacttacagt tagtcagagc ccgttaatgg gtgatggcgt acatcttgca    3720
gaatggaccg gcgagttatg tcaacatgcg aggttaagta gaataaagcg aagccgtaga    3780
gaaatcgagt ctgaataggg cgatttagta tgttgatata gacccgaaac caggtgatct    3840
acccatgagc aggttgaaac ttaggtaaca ctaagtggag gaccgaaccg cagtacgcta    3900
aaaagtgccc ggatgacttg tgggtagggg tgaaattcca atcgaacttg gagatagctg    3960
gttctctccg aaatagcttt agggctagcg tgtagtgtta aatgatgggg gtagagcact    4020
gaatatgaat tggcggcgcc tagccgtact gactataatc aaactccgaa tactatcatg    4080
tattactatg cagtcggtac atcggtgata acgtcgatgc acgcgagggg aacaacccag    4140
atcgtcagct aaggtcccaa aattgtgtta agtgagaaag gttgtgaagt tcttaaaaca    4200
gctaggatgt tggcttagaa gcagccaccg tttaagagt gcgtaatagc tcactagtcg    4260
```

```
agagactttg tgccgataat tcaacgggac taaaacacaa taccgaagct acgggcagaa      4320
atgcgttagg agagcgttgt aagggcttag aagccagacc gtgaggactg gtggagcgct      4380
tacaagtgag aatgccggta tgagtaacga ttcagagtga gaatctctga cgcctattgg      4440
ggaaggtttc ctgggcaagg ttcgtccacc cagggttagt cgggtcctaa gacgaggccg      4500
aaaggcgtag ccgatggaca acaggttaat attcctgtac tttcttaaca tgtgatggag      4560
tgacggggaa ggataatttt accactaatt ggattgtggg gtaagtaaca actgggttat      4620
gtaggcaaat ccgcataact taactgggag ttacgatgca tagcaaaagg gcaactgagt      4680
agcgaattag atgatttcat gcctcttaaa aaagcttcta acattaagtg ttaggaaacc      4740
cgtaccgaga acgacacac gtccccaaga tgagtattct aaggcgagcg agaaaactat       4800
tgtcaaggaa ctctgcaaat tcatcccgta agttcgcaag aagggatgcc cacaataaaa      4860
tgtgggccgc agtgaatagt aaggggggaac tgtttatcaa aaacacagct ctatgctaag     4920
tcgtaagatg atgtatatgg ggtgactcct gcccagtgcc cgaaggttaa gcagaggtgt      4980
tagcattagc gaagcattaa tgtgaagccc ggtgaacggc ggccgtaact ataacggtcc      5040
taaggtagcg aaattccttg tcggctaaat actgacctgc acgaaaggag taattatctc      5100
ttaactgtct cgacaataga ctcggtgaaa ttatggttcc ggcgaagacg ccggagaccc      5160
gcatctagac gaaagacccc gtggagcttt actataact tcatattgga gtttgattta      5220
acatgtgtag dataggtggg agacgttgat gcttgaacgc tagtttaaga gtagtcgccg      5280
ttgaaatacc acccttgtta cattgaactt ctaacttgtt cccgttatcc gggaagagga      5340
cagtgtgtgg tgggtagttt gactggggcg gtcgcctcct aaagggtaac ggaggcgttc      5400
aaagttacac tcaatacggt cagaaaccgt atctaagagc ataaaggtag aagtgtgatt      5460
gactgtgaga cctacaagtc gagcaggtgc gaaagcagga cttagtgatc cggcggttct      5520
tcgtggaaag gccgtcgctc aacggataaa agctaccccg gggataacag gcttatcttt      5580
cccaagagat cacatcgacg ggaaggttg gcacctcgat gtcggctcat cgcatcctgg       5640
agctggagtc ggttccaagg gttgggctgt tcgcccatta aagcggtacg cgagctgggt      5700
tcaaaacgtc gtgagacagt ttggttccta tctgatgtgg gcgttggaat attgatgaga      5760
gctactctta gtacgagagg accggagtgg acgcaccgat ggtgtgccag ttgtttcgcc      5820
agaagcatag ctgggtagcc aagtgcggca gggataaccg ctgaaagcat ctaagcggga     5880 agcccccctca aagattagta ttcccttttaa aattccttat agactatgag gttgataggc    5940
tggaggtgta agtgcagcaa tgcattcagc tgaccagtac taataaattt attggtttaa      6000
tagtaatatt ctatatagtt atctaaatta agtcgtattc agttttcaaa gaacaacaaa      6060
tagcctaatg gctatttttt tatttaaaaa ttataaaaat tttaaaaatt tgttataatt      6120
tcaacgcaat atatgaagac agtaacggcg tagtgcttaa taatgttacc tagtatgttt      6180
atacttgttt gtacattgca taatctttat aggaggaata ataatgagcg cattaaaaga     6240
tgccaaggtt ttagttgttg aagaaatttc aaacaattta aaagaatcac aagcattata      6300
tgtaattaat tatgctactt tggatgttgt ttcatttcaa gaaattagaa aagaattagc      6360
tccaaataat gcattgctaa aagtttacaa aaatagacaa gttaaacaag cattaaaaaa      6420
tacagaatat gcaaatatta atgatagttt agttttacaa aatgcttatg cctttgttaa      6480
aggtgattcg ttagcagcat taaagacctt gtaggcttaa aagaagaaat tccctgcatt     6540
aagaattgta agtggaattt atgaaaataa agtagttgat gaaaaacat tagacgaaat       6600 atcaaaactt ccttcattta cagaatcact tatgattctt ggaaattcat tattgagtcc      6660
```

```
attgaaacaa ttatcaattg gtttaaatga attaataaaa caaggaaaaa tttcagaata   6720 attatttta aaggagattt atcatggcaa aattaacaaa agaagaattt gtttcagcat     6780
taaaagaaat gaacattaaa gaagttatgg aattaattca aggattaaaa gaagaatttg   6840
gaattgatcc aacagcagtt gtagcagcag cagctccagc agcagcagct gacgcagcag   6900
aagaaaagac tgtatttaat gttactttaa aatcagatgg tggaaacaag ctagcagtta   6960
ttaaagttgt taaagactta ttaggtcttg gattaatgga tgctaaaaaa cttgttgaat   7020
cagcacctgt tgtaattaaa gaaaatgcta aaaagaaga agctgaagaa ctaaaagcta   7080
aattaacaga agctaaagcc gaagttactt tagactaatt acaaaaaaca caagtgaggc   7140
ttttaataca caaagccttt tttgtgtttt ttgtcgtata ttatgcacgt gtgcgtatat   7200
acaacaaaaa ataaaaatat aaacaaaatt taataaaaat tgaggtaaag catggtgaat   7260
aaggataaat acgaaattag aaaatttgga cctattaccc taagacgtga ctattcaatt   7320
agtcaaaaga aattcgaaac tcctgacttt cttgaaatgc aacgtgaatc agttgaaaaa   7380
tttctaacag ttggaattga agaagaatta agaaatatct atccaattga agcacatgga   7440
aaagttagaa ttgaatacat tcataattca gcacattttg aatatcctaa aaaaactgaa   7500
tatgaaagca ttaagaagc taaacaaaaa ggttcatcat atcaaggaaa gttaaaagca   7560
cacctaagac aaatcaatat cgaaacaggt gaagttgaag attcagaagt agtatttgct   7620
gaaattccta atgacttta tggtggatca tttattatca atggttcaga aaaagttatt   7680
gtttcgcaat taattagatc taccggggct tattttggaa ttaatgttag aaataaacaa   7740
gccaacgact tgtttaataa agtagaaatt attcctcaaa ttggttcatg agtagaaatt   7800
tatcataaag taacttctca aaatccagat actgtaaaaa tacatatcga taaaaacaaa   7860 tcattttag ttgtaacttt cttaaaagca ttaggattta gtgaatcagg tattagaaga   7920
atgtttggcg aaaatattcc agaattgaaa gaaacattta aacgtgataa aatcactgga   7980
attaatgcag aagaagttac aagagaagca caagaagcaa tttatagaat catcagaaaa   8040
ggcgatcgta tgacagctga ttctgctaga aatttaattc ctacaacttt gtttaatgaa   8100
aaaagatata gtttaactga aacaggacgt ttcactttaa atagaaaatt aaacattatt   8160
gaaagaattg ctaattctta tttagcagaa gatatttttt ctagtgaagg tgaacttctt   8220
tatgaaaaag gaatgttcat tacttgaaat atcgcaagaa agattcatga tgaatttaaa   8280
caaggaatta ttcctatgtg aaaattgcca gatattgatg aaaatgcata tggatctcaa   8340
cttgaagtta aaggaaatga acaacttgca agtagaatct tgtaacaag catttgaata   8400 tatccaactg aaaatgatat gttgcatgac caaaaagttt tggttttagg taatgatcct   8460
acatcaacag aaaatttctt gttgattcct gatttaattg caacgatttc gtattatttt   8520
aatttacttt caaaggttgg ggttgatgat gatcctgact cattagttaa taaaagaatt   8580
gtaacaatag gcgaattatt acaaaatcaa tttagaatag gctattaaa attagaaaaa   8640 aatacaagag aagaatctca gcaaaagata ttgataagat tactgctaag aacgttacaa   8700
ataataaacc aatatttaat caatttaaat cgttctttaa cacatcaaaa ctttctcaat   8760
ttatggatcc aatgtaatcc tcttgctgaa atatcaaaca agagaagaat aacctcccta   8820
ggaccaagag ggttgaaccg tgatactgca caatttgaag ttcgtgacgt tcaccctacc   8880
cattatggaa gaatttgtcc tattgaaaca cccgaaggac caaacattgg tttaatttta   8940
aatttagcat catttgctaa aattgataaa tatggtttta ttcaatcacc atatttcaga   9000
```

-continued

```
gtaaataaaa aagttgtaga tttttcagaa ccagtttaca ttactgcaat tgaagaaaca    9060
ggatatacat ttgcacaatc aactgttcac attgaaggta atgtaattgt tgatgaaaaa    9120
gtaatggtaa gacgtgacaa tgaatattta gaagtaaatg ctgaagatgt agattttatt    9180
ggtgtctcaa accgtcaaat gacctcaata gctgcttcgg ctataccatt tttggaaaac    9240
gatgatgcta accgtgcatt gatgggttca aacatgcaac gtcaagctgt tccagtgtta    9300
ttccctgaag caccattagt tgctacagga gttgaagctg atattgctaa atattcatca    9360
accaatatta gagcaaccag atcaggtgtt gttaactatg tagatgctaa cgttattaaa    9420
gtaactcctg aaaatagttc aaaaagtgat gtttatcatt taagaacatt tgaaagaagt    9480
aaccaaggta cattaattca ccaagtactt ttggttaaag ttggccaaca aattaatgca    9540
ggagatttat tagttgatgg tccttcaatg aaagatggag aattagcatt aggaaaaaac    9600
gttctagtag gttttactac ttgacatggt tataactatg aagatgccgt tgttttatct    9660
gaaagattgg ttaaagatga tgtttataca tcaattcaca ttgaagaaca atcaattcaa    9720
tttagacatt caaaggctgg cgaagatatt ttaactgcag atattcctaa cgtttcaaac    9780
tattctaaac gtttcttagg tgaaaatgga attgttagag ttggttcaga agtaacagca    9840
ggtgatattt tagtcggaag aacttctcca aaaggtgaag aaaacccaac tccagaagaa    9900
aaattaatgg ctgcaatttt tggtcaaaaa actgcctcaa gaaaagatac ttctctaaaa    9960
gtaaaacatg ccacaatgg aaccgttgtt gctgttgata ttctaagtag agaatttggc   10020
gaccaattag aagatggcat tgaaaaaata gttaaggtat caattgctca aaaacgtaaa   10080
attcaagtcg gcgacaagat ggctggtcgt cacggaaata aggtgttgt ttcaatagta   10140
ttgcctgttg aagaaatgcc ttatttagca gatggaacac cattagatat tgttttaaac   10200
cctcaaggtg tcccttcacg tatgaacatt ggtcaagttc taga                    10244
```

<210> SEQ ID NO 2
<211> LENGTH: 6663
<212> TYPE: DNA
<213> ORGANISM: Mycoplasma gallisepticum L08897.1 GI:530152

<400> SEQUENCE: 2
agatctattg gtatgtccca ttaattgctt tttcttattc atcaatcgtt tatcttttat 60
ttggttttgg tttaaataat atcttcttaa ttaatctatt taatatccaa ggtgctgata 120
atttagttgt ttctaatctt gttttaagaa ttacattagt tcaatcgatt tttattgcat 180
taagtatgaa tgcacaattg ttgtttcaat caactcagag aattgggatg gcttggatcg 240
cttcattaat gcaagggcta tttacttttg ctccagtctt ctttactatg tacaacttag 300
caattgatac aaataatatt tatctatata tttggatcca accaattaat gcgatcttaa 360
cttgtattgg taactgaatt atctcaattc cgtttgctca taaatatcgt gagtttgtta 420
gtaaacgttt tgatattggc acgatgcttg ataaatattt aaataaaact aaaaaaccta 480
aggtcaaagc aaaacaataa ttttttttcaa ataatctttt caaacgaaaa tattgtgcta 540
taattttaaa ggctatcttt tcagcaatat cgaatagcta gcctaaaatg cttcttgaaa 600
actgaataga atctgtcatt ttctgagagt ttgatcctgg ctcaggatta acgctggcgg 660
catgcctaat acatgcaagt cgatcggatg tagcaataca ttagaggcga acgggtgagt 720
aacacgtatc caatctgcct tatagtgggg gataactagt cgaaagatta gctaataccg 780
cataacaagt taactatcgc atgagaataa ctttaaagaa gcaactgctt cgctataaga 840
tgagggtgcg gcatatcagc tagttggtga ggataatggc ccaccaaggc gatgacgtgt 900

```
agttatgctg agaggtagaa taaccacaat gggactgaga cacgcccat actcctacgg      960 gaggcagcag tagggaattt ttcacaatgg acgaaagtct gatggagcaa tgccgcgtga     1020
acgatgaagg tcttttttaga ttgtaaagtt cttttatttg gaagaacag ttaatagagt     1080 ggaaagctat taatttgact gtaccatttg aataagtaac gactaactat gtgccagcag    1140
tcgcggtaat acataggttg caagcgttat ccggatttat tgggcgtaaa acaagcgcag    1200
gcggattaga aagtctggtg ttaaaagcaa ttgcttaacg attgtatgca ttggaaactt    1260
ctagtctaga gtttggtaga gagtcctgga actccatgtg gagcggtgaa atgcgtagat    1320
atatggaaga acaccagagg cgaaggcgag gacttgggcc aatactgacg cttaggcttg    1380
aaagtgtggg gagcaaatag gattagatac cctagtagtc cacactgtaa acgatggatg    1440
ttaagtgtcg gagcgaatac ttcggtgctg cagttaacac attaaacatc ctgcctgagt    1500
agtacattcg caagaatgaa actcaaacgg aattgacggg gacccgcaca agtggtggag    1560
catgttgctt aattcgacgg tacacgaaaa accttaccta gacttgacat cttgggcgaa    1620
cgtatagaaa tatagtggag gtcaacccaa tgacaggtgg tgcatggttg tcgtcagctc    1680
gtgtcgtgag atgttgggtt aagtcccgca acgagcgcaa cccttatcgt tagttacttt    1740
gtctaacgag actgccaacg taagttggag gaaggtgggg atgacgtcaa atcatcatgc    1800
cccttatgtc tagggctgca aacgtgctac aatggccaat acaatcagtt gcaaatccgt    1860
aaggtggagc taatctgtaa agttggtctc agttcggatt gagggctgca attcgccctc    1920
atgaagtcgg aatcactagt aatcgcgaat cagccatgtc gcggtgaata cgttctcggg    1980
tcttgtacac accgcccgtc aaactatgag agctggtaat atctaaaacc gtgttgctaa    2040
ccgcaaggag gcgcatgtct agggtagggc cggtgattgg agttaagtcg taacaaggta    2100
cccctacgag aacgtgggggg tggattacct cctttctatg gagtatatta atacactaac    2160
acgatataca cctgttacat ataacggtga aacaattaaa acccagcaag aaaagttaaa    2220
cccataaaag caaattgata acttaaaaat tgttggtcgg attctattca gttctcaagg    2280
ggtattttaa aagtagttat taagtttttt tctttaaagc ttttgaaact taataacact    2340
ttaagttaac cttgttaaga tcattaattt tacctttcaa agatcaaaga agaattatta    2400
aaatcttttt catctgataa ctaataaact aactaaatca ttgatgcata attaactgca    2460
tcaatgattt ttttgttatt tttaccgcaa aaaatgcaga ttcatctgtt caaaccaatt    2520
atttaaaaag gcttttttta ttattaatca ttcgttattt ttttacttgt gattttagct    2580
ttaaatctta taaaaaattt aatgataaaa gttttttttag aaaagtgttg tgcaaactga    2640
tttgttgtgc cttaatcttt aaggcttata tagctacatt gttctttgaa aactgaatac    2700
gacaaatctt tctagtccga aatttgatta aagtatcaaa tcaaatttca tataattata    2760
gattcaataa aaatagctaa tggatcaaat acataagtta ctaagggctt atggtggatg    2820
ccttggcact agaaggcgat gaaggacgtg caaacctgcg aaatgctacg gggagctggt    2880
tggaagcgat aatccgtaga tgtccgaatg ggggaacctg attaatagtg atattaatca    2940
tttagatctg aatacatagg gtctaaaagc aatacgttgt gaagtgaaac atctcagtag    3000
caacaggaaa agaaatcgaa agagattccg tgtgtagtgg cgagcgaaag cggaacaggc    3060
caaaccaaga tttatcttgg ggttatagga ctgcaatgtg gactttgaac tgataggaga    3120
agtagttgaa aagctacgcg ataaagggtt atagccccgt atcttaaatt ggtttaatac    3180
ctagcaggat cctgagtaca tcgagaaacg ttatcttgat ggaagtcgcc cagaccattg    3240
```

```
ggcaagccta aatactaact agtgaccgat agcgtatagt accgtgaggg aaaggtgaaa    3300
agaacccagg gatgggagtg aaatagattc tgaaaccata tgcctacaac gtgtcagagc    3360
acattaatgt gtgatggcgt gcgttttgaa gtatgagccg gcgagttatg atagcaagca    3420
ggttaacctt tagaagggaa gccgaagcga agcgagttt gaatagagcg aattaaagtg     3480
tttgttatta tagacccgaa acgggttgag ctagtcatgg gcaggttgaa gttagagtaa    3540
catctaatgg aggaccgaac cgactttcgt tgaaacgaca gcggatgacc tgtgactagg    3600
ggtgaaattc caatcgaaat ccgtgatagc tggttctcgt cgaaatagtt ttaagactag    3660
cgtaagatca tgatcaactg gaggtagagc tactgaatgt atgatggcgc gccttggtg    3720 tactgaatac aattaaactc cgaatgccaa ttgatttatt cttgcagtca gacagtgggg    3780
gataagcttc attgtcacaa ggggaagagc ccagatcatt aaataaggtc cctaaaatat    3840
gctaagtgga aaaggttgtt aaaatactta aacagcaagg atgttggctt agaagcagcc    3900
atcgtttaaa gagtgcgtaa cagctcactt gtcgagtgtt tttgcgccga agatgtaacg    3960
gggctaagca tattaccgaa tttatggatt attattcgta agaatgatag tggtagacga    4020
gcgttgtata tgggatgaag tcaaaccgtg aggattggtg gactgtatac aagtgagaat    4080
gccggtgtaa gtaacgcttg agagtgagaa tctctcaaac cgattgacta aggtttcctg    4140
gacgagggtc gtccttccag ggttagtctg gacctaaggc gaggcagaaa tgcgtagtcg    4200
atggaagaac aggttaatat tcctgtacaa acaaatagct gatggagtga cggagaaggt    4260
taatgcatcc ccattatcgg atttggggtt aaataagaag tcttaagggt tggcaaatcc    4320
gcctttttta aggagaactt atgaatacga gtgaacgctt tgcaagtagc gaagatgcat    4380
acatcacgct tccaagaaaa gcttctaggg ttaactattt gtttccagta ccgagaacga    4440
acacacgtgg tcaaggagaa gatcctaagg ttagcgagtg aactatagct aaggaactct    4500
gcaaattcat cccgtaagtt cgcaagaagg gatgctcaat gtaacagttg agccgcagtg    4560
aagaacgagg ggggactgtt taactaaaac acagctctat gctaaatcgc aagatgatgt    4620
atatggggtg acacctgccc agtgctggaa ggttaaagaa gggtgttaga gcaatcaaag    4680
ctcccgactg aagcccccagt gaacggcggc cgtaactata acggtcctaa ggtagcgaaa    4740
ttccttgtcg ggtaaattcc gtcccgcttg aatggtgtaa ccatctcttg actgtctcgg    4800
ctatagactc ggtgaaatcc aggtacgggt gaagacaccc gttaggcgca acgggacgga    4860
aagaccccat gaagctttac tgtaacttaa tattgggcag agtttagaca tatagagaat    4920
aggtgggaga ctttgaagca acttcgctag gagttgtgga gtcaccagtg gaataccacc    4980
tttgttaaaa ttcttctcta actagttgct gttatccagc aataggacag tgttaggcgg    5040
gcagtttgac tggggcggtc gcctcccaaa aggtaacgga ggcgtgcaaa ggtaccctca    5100
gcacggttgg aaatcgtgtt aagagtgtaa tggtataagg gtgcttgact gtgagactaa    5160
caggtcgaac aggtaagaaa ttaggtcata gtgatccggt ggttcagtat ggaatggcca    5220
tcgctcaacg gataaaagct actctgggga taacaggctg atactgccca agagttcaca    5280
tcgacggcag tgtttggcac ctcgatgtcg actcatctca tcctcgagct gaagcaggtt    5340
cgaagggttc ggctgttcgc cgattaaaga gatacgtgag ttgggttcaa accgtcgcga    5400
gacaggttgg tccctatcta ttgtgcccgc aggaagattg aaaagattta ctcttagtac    5460
gagaggaccg gagtgaagac acctcttgtg ctccagttgt agcgccaact gcaccgctgg    5520
gtagcaacgt gtcgaacgga taacgctga aagcatctaa gtgtgaaacc gactttaaga    5580
ataatcttcc cttccagcaa tggagtaaga atcgttgtag actacgacgt tgataggcta    5640
```

```
aaggtgtaag tgccgcgagg tatttagctg attagtacta ataattcgag gacttagatt    5700
tgatcaaaaa cattagctgt ttttatcta atatgatttg ttgtattttg ttttcaaag     5760 agcaatgtgt gtgatatcga tatcgtgatg gaaacacctg gtcccattcc gaacccagaa    5820
gttaagcatc atggagccaa aggtagcgca agcaagaata ggaaaatatc acgccaacaa    5880
aacgacacca ttaatttggt gtcgtttttt tacaacttaa acagatttta agtttctaaa    5940
atgaccttat tttaaccgtt attttcttc tttaaaata aataagtatt attttaaaca      6000
aaaaaaatta aacagttata atacattagt ttaacgatta agatttagaa ataaatctaa    6060
gcactcttta tcttttaaag gggctaaaca actaaccagt ttttgaataa ttccataatg    6120
ataaatgatt atggaattat taatcactag tgctaactgg ttttttatgc aacaaccaat    6180
ttagattaaa aatattaagg aatcaccata atgaaaaaat acttcaaaat cattaatgtt    6240
accaggaggc aattagcact ctttttagtt tatctggcga ccttactttt tgccagtgct    6300
ggaatcatta cgatcatgac ttatggaatt gctttccctg ggggcaataa cttcgtaatt    6360
tataatgaaa acttctttaa gacttcatta attttaccct tagttttctt tgtgatcttt    6420
gctattagtg ggcttgtgat cttactaacg ggtaaagaaa cttataagtt tgatcataaa    6480
ctgatttatc aaaattataa gtttaaacta atcttatctt taatcgaaat tattcaagcg    6540
attgcatgag tattttcctt gggaattcta atcgtttatt tttatccgat agataaaact    6600
attagtcaag tctatcaaga tcaaattgct tcagtagatt ttgctaatgc taatattaga    6660
tct                                                                   6663

<210> SEQ ID NO 3
<211> LENGTH: 2827
<212> TYPE: DNA
<213> ORGANISM: Acholeplasma laidlawii CP000896.1 GI:161984995 bases
      75178-78004

<400> SEQUENCE: 3
gaacaaaggg cacacagtgg atgccttggc accaagaggc gatgaaggac ggaactaaca      60
ccgaaatgct cggggaagct gtaagtaagc gacgattccg agatgtccga atgggggaac    120
ccactatgtt gaagacatag tatctaacac acgtgttaga ggcaatacgt agggaactga    180
aatatctaag tacctacagg aaaagaaagt aataacgatt ctgtcagtag cgacgagcga    240
acgcggagga gccagatacc taaggttaca aaattatata atagatgaac gatgtgggaa    300
aatcggtcga agaaggtgag agccctgtag tcgaaattat ataatccatg gtatcagaaa    360
gtagggcggg acacgtggaa tcccgtttga agataggagg accatctcct aaggctaaat    420
actacttggt gaccgatagt gaaccagtac agtgatggaa aggtgaaaag accccggga     480 ggggagtgaa agagaacctg aaactgtgtg cttacaatta gtcagagccc gttaatgggt    540
gatggcatgc cttttgtaga atgaaccggc gagttatgtt acatagcaag gttaaggatg    600
aaggtccgga gccgaagcga aagcgagtct gaatagggcg cttaagttgt gtgatgtaga    660
cccgaaactg ggtgatctag ccatgagcag gttgaagtaa gggtagtacc ttatggagga    720
ccgaaccgcc gcctgttgaa aaaggctcgg atgacttgtg gctaggggag aaattccaat    780
cgaactcaga gatagctggt tctccccgaa atatctttag ggatagcgtc aacaaaatag    840
gtttatcgaa ggtagagcac tgaatgtgtg atggccccac ctcggggtac tgatctcaat    900
caaactccga atgtcggtaa agtaagttgg cagtcagact acgggtgata aggttcgtgg    960
tcaaaaggga aagagcccag accgccagat aaggtcccaa aatatatgct aagtggaaaa   1020
```

```
ggaagtagag atgcacaaac agccaggagg ttggcttaga agcagccatc ctttaaagag   1080
tgcgtaaaag ctcactggtc gagtgactct gcgccgaaaa tgtaccgggg ctaagcatat   1140
taccgaagct gcggatttaa aaagattttt taagtggtag gggagcgttc ctaacagcgg   1200
tgaagctaga tcgtgaggac tagtggagcg ttaggaagtg agaatgccgg tgtaagtaac   1260
gaaaagacag gtgagaatcc tgtccgtcat aaacccaagg tttccagggg aaggttcgtc   1320
cgccctgggt aagtcgggc ctaaggtgag gctgaagagc gtagccgatg gataactagt   1380
agagattcta gtaccagtgt agtgactgat ggagtgacaa agaaggatag gcgtccaccc   1440
ttaatggatt gggtgagaag gattcgaggc tagtacttag gcaaatccgg gtactgttaa   1500
agctgagaac tgatataaag acgtacgagt tcatgctttc aagaaaagct tctaaggtta   1560
atcattatac tgcccgtacc gtaaaccgac acaggtgggt gagtagaata tattaagacg   1620
cgcgagaaaa ctgttgttaa ggaactcggc aaattgaccc cgtaacttcg ggaaaagggg   1680
gactccttat gaaaacgagg agtcgcagag aaaaggccca agcgactgtt tagcaaaaac   1740
acaggtctct gcaaaaccgt aaggtgaagt atagaggctg acgcttgccc ggtgctggaa   1800
gattaagagg agatgtcagg gttaaaccga agcattgaat tgaagtccca gtaaacggcg   1860
gccgtaacta taacggtcct aaggtagcga aattccttgg cgggtaagtt ccgtcctgca   1920
cgaaaagcgt aacgatttgg gcactgtctc aacaacagac tcggtgaaat caagctgccg   1980
gtgaaaacgc cggctacccg cgattagacg aaaagacccc atggagcttc actgtaactt   2040
gatattgaaa ctgggtgtaa gatgtacagg ataggtggga ggctatgaag atagtacgct   2100
agtattgtcg gagccaacgt tgggatacca cccttcgtgc acttagtttc taacttctag   2160
atgtgtaatc taaaggacag tgtctggtgg gcagtttgac tggggcggtc gcctcccaaa   2220
gagtaacgga ggcgctcgaa ggttacctca gaatggttgg aaatcattct atagagtgca   2280
atggcagaag gtagcttgac tgcgagacca acaagtcgag cagggacgaa agtcggacat   2340
agtgatctta cggtaccgaa tggaagggcc gtgactcaac ggataaaagt taccctgggg   2400
ataacaggct tatcgcttcc aagcgttcac agcgacgaag cggtttggca cctcgatgtc   2460
ggctcgtcgc atcctggagc tggagtaggt tccaagggtt gggctgttcg cccattaaag   2520
cggcacgcga gctgggttca gaacgtcgtg agacagttcg gtctctatct atcgtgggcg   2580
ttggaaattt gaagggagct gttcctagta tgagaagacc ggaatggacg caccctggt   2640 gcaccagtta gtacgccagt actacagctg ggtagctatg tgcggaaggg ataaacgctg   2700
aaagcatcta agcgtgaagc ccccttaag atgagatttc ccaattagta agacccctca   2760
aagactatga ggttgatagg ccaggtgtgt aagtacagcg atgtattcag cttactggta   2820
ctaaatag                                                           2827

<210> SEQ ID NO 4
<211> LENGTH: 3023
<212> TYPE: DNA
<213> ORGANISM: Spiroplasma insolitum EU582532.1 GI:175362846

<400> SEQUENCE: 4
tttgaagtta caaagggcgt atggtgaatg ccttgggaat aggagacgat gaaggacgtg     60
actacctgcg ataaggttcg gggagctgga agtaagcttt gatccggaca tgtccgaatg    120
gggaaacccg gtgagattaa tctctcatca tcctataatg aataatagtt atagagaagg    180 tataccctagg gaattgaaac atcttagtac ctagaggaaa agaaagcgaa agcgattctc    240
```

```
tgagtagcgg cgagcgaaag gggaacagcc caaaccaact tatgttgggg ttgtaggacc    300
acattagtag agttacaaaa cttgtttata gtagaaatgg ttgggaaacc atgccacaga    360
gggtgatagc cccgtatacg aaatgaacag gacttgaagt ggaatcctga gtacggcgag   420
acacgtgaaa tcttgtcgga atcaacgcgg accaccgcgt aaggctaaat actacctatt   480
caccgatagt gaaccagtac cgtgcctgga aaggtgaaaa gcaccccggg aggggagtga   540
aaaagtacct gaaaccatat gcctacaaga agtcggagcc cgttaatggg tgacggcgtg   600
ccttttgtag aatgagccgg cgagttatga tagcatgcaa ggttaagtgg aagacacgga   660
gccgtagtga aagcgagcct taatagggcg tttagtatgt tgtcatagac ccgaaaccag   720
gtgatctagc catgagcagg ttgaagttga ggtaaaactt aatggaggac cgaaccgacg   780
ttcgttgaaa agaccgcgga tgacttgtgg ctaggggtga aattccaatc gaacctggag   840
atagctggtt ctccccgata tagctttagg gctagcgtcg aggttaagca aattggaggt   900
agagcactaa atgtatgatg gccccaccta ggggtactga atgcaattaa actccgaatg   960
ccaattttgt atactcggca gtcagtacat gggtgataag gtccatgcac gtaagggaaa  1020
cagcccagat catcagctaa ggtcccaaaa tttatgctaa gtgtgtaagg atgtgaagtc  1080
gcttagacag ctaggaggtt ggcttagaag cagccaccct ttaaagagtg cgtacagctc  1140
actagtcgag taactttgcg ccgaaaatgt accggggcta agcataatac cgaagctatg  1200
ggttttgtat agtaatatac agggcggtag gggagcgttc taacagggat gaaggtagac  1260
cgtgaggact gctggactgg ttagaagtga gaatgccggc atgagtaacg tttgagggtg  1320
agaatccctc atgccgtttg accaaggttt cctgggcaag gttcgtccac ccagggttag  1380
tcaggaccta aggcgaggcc gacaggcgta gtcgatggac aacaggttga tattcctgta  1440
ccaccatata gagtgatgga gtgacggaga aggatagtat atcccggtta ttggattccg  1500
ggctaagcac aaagagggta aggttggcaa atccgccttg cataaccttg aagtgtgatg  1560
gggagtgaac ggttcgccta gtaacgaagt atatgactcc atgcttccaa gaaaagcttc  1620
tagcgttaat ctataaggtg cctgtaccta gaacgaacac acgtggtcaa ggagagaatc  1680
ctaaggcaag cgagataact gtagctaagg aactctgcaa aatagccccg taagttagcg  1740 agaagggggtg ctcatagcaa tatgagccgc agtgaagagg aagggacaac tgtttagcaa  1800
aaacacagct ctctgcaagt cgtaagacga cgtatagggg gtgacgcctg cccagtgctg  1860
gaaggttaag gggattagtt agcattagcg aagctttgaa ccgaagcccc agtgaacggc  1920
ggccgtaact ataacggtcc taaggtagcg aaattccttg tcaggtaagt tctgacccgc  1980
acgaaaggcg taatgatccc ttcgctgtct cggctgcaga ctcggtgaaa ttttagtacc  2040
tgtgaagatg caggttaccc gcaactagac ggaaagaccc catggagctt tactatagct  2100
tgatattggg ttttgacata gtatgtatag gataggtggg agactttgaa gcagcaacgc  2160
tagttgttgt ggagtcatcc ttggaatacc acccttgcta tgtcggaatc ctaacctaga  2220
tctgttagcc agatcagaga cagtgtcagg tgggtagttt gactggggcg gtcgcctcct  2280
aaaatgtaac ggaggcgccc aaaggtaccc tcagtatggt cggaaatcat acatagagcg  2340
caaaggtaga agggtgcttg actgtgagac ttacaagtcg aacaggagcg aaagctgggc  2400
ttagtgatcc ggcggtcccg cgtggaaggg ccgtcgctca acggataaaa gttaccctgg  2460
ggataacagg ctgatctccc ccaagagttc acatcgacgg ggaggtttgg cacctcgatg  2520
tcggctcatc gcatcctgga gctgaagttg gttccaaggg ttgggctgtc gccattaagg  2580
cggtacgcga gctgggttca gaacgtcgtg agacagtttg gtccctatct gttgtgggcg  2640
```

```
taggaagttt gaagagatct gtccctagta cgagaggacc gggatggacg caccgctggt    2700
gctccagttg tcacgccagt ggcacagctg ggtagctatg tgtggaaatg ataatcgctg    2760
aaggcatcta agcgagaagc atactttaag atgagacttc ccatccttcg tggagtaaga    2820
ccccttgaag acgacgaggt tgataggttg ggtgtgtaag cacggtgacg tgttcagcta    2880
accaatacta ataggtcgag gacttcaatg aagaacccat ttacaaaata aaagattgtt    2940
tattatctag ttttgagagg ataattccgc tcagcataat ctggtgctta tggcatagtg    3000
gtcacacccg ttcccatccc gaa                                           3023

<210> SEQ ID NO 5
<211> LENGTH: 58
<212> TYPE: DNA
<213> ORGANISM: Artificial Sequence
<220> FEATURE:
<223> OTHER INFORMATION: synthetic oligonucleotide

<400> SEQUENCE: 5
ctaaatactg acctgcagta ggtaccgatg acgacctttc gtgcaggtca gtatttag       58

<210> SEQ ID NO 6
<211> LENGTH: 54
<212> TYPE: DNA
<213> ORGANISM: Artificial Sequence
<220> FEATURE:
<223> OTHER INFORMATION: synthetic oligonucleotide

<400> SEQUENCE: 6
tgtaaccatc tccagtaggt accgatgacg agagacagtc aagagatggt taca           54

<210> SEQ ID NO 7
<211> LENGTH: 45
<212> TYPE: DNA
<213> ORGANISM: Artificial Sequence
<220> FEATURE:
<223> OTHER INFORMATION: synthetic oligonucleotide

<400> SEQUENCE: 7
gccggcagta ggtaccgatg acgagtagcc ggcgttttca ccggc                     45

<210> SEQ ID NO 8
<211> LENGTH: 45
<212> TYPE: DNA
<213> ORGANISM: Artificial Sequence
<220> FEATURE:
<223> OTHER INFORMATION: synthetic oligonucleotide

<400> SEQUENCE: 8
tgatccagta ggtaccgatg acgagccgag acagcgaagg gatca                     45

<210> SEQ ID NO 9
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 9
cgccguucac uggggcuuc                                                  19

<210> SEQ ID NO 10
<211> LENGTH: 19
<212> TYPE: DNA
```

```
<213> ORGANISM: Artificial Sequence
<220> FEATURE:
<223> OTHER INFORMATION: synthetic oligonucleotide

<400> SEQUENCE: 10
cgccguucac ccgggcuuc                                                    19

<210> SEQ ID NO 11
<211> LENGTH: 47
<212> TYPE: DNA
<213> ORGANISM: Artificial Sequence
<220> FEATURE:
<223> OTHER INFORMATION: synthetic oligonucleotide

<400> SEQUENCE: 11
acguguguuc guucucggaa aaaaaaaaaa aaaaaaaaaa aaaaaaa                     47

<210> SEQ ID NO 12
<211> LENGTH: 52
<212> TYPE: DNA
<213> ORGANISM: Artificial Sequence
<220> FEATURE:
<223> OTHER INFORMATION: synthetic oligonucleotide

<400> SEQUENCE: 12
caacaguuuu cucgcgcgut taaaaaaaa aaaaaaaaaa aaaaaaaaaa aa                52

<210> SEQ ID NO 13
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 13
tcgtcagtag gtaccgatga cga                                               23

<210> SEQ ID NO 14
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 14
ccaggaauuu cgcuaccuua ccugg                                             25

<210> SEQ ID NO 15
<211> LENGTH: 57
<212> TYPE: DNA
<213> ORGANISM: Artificial Sequence
<220> FEATURE:
<223> OTHER INFORMATION: synthetic oligonucleotide

<400> SEQUENCE: 15
aatttaatac gactcactat agggagaacg gcggccgtaa ctataacggt cctaagg          57

<210> SEQ ID NO 16
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 16
gaacctagtt gggcgagtta cgga                                              24
```

<210> SEQ ID NO 17
<211> LENGTH: 48
<212> TYPE: DNA
<213> ORGANISM: Artificial Sequence
<220> FEATURE:
<223> OTHER INFORMATION: synthetic oligonucleotide

<400> SEQUENCE: 17
gaacctagtt gggcgagtta cggacctttc gtgcaggtca gtagttag            48

<210> SEQ ID NO 18
<211> LENGTH: 58
<212> TYPE: DNA
<213> ORGANISM: Artificial Sequence
<220> FEATURE:
<223> OTHER INFORMATION: synthetic oligonucleotide

<400> SEQUENCE: 18
ctaactactg gaacctagtt gggcgagtta cggacctttc gtgcaggtca gtagttag   58

<210> SEQ ID NO 19
<211> LENGTH: 43
<212> TYPE: DNA
<213> ORGANISM: Artificial Sequence
<220> FEATURE:
<223> OTHER INFORMATION: synthetic oligonucleotide

<400> SEQUENCE: 19
gaacctagtt gggcgagtta cggacctttc gtgcaggtca gta                 43

<210> SEQ ID NO 20
<211> LENGTH: 48
<212> TYPE: DNA
<213> ORGANISM: Artificial Sequence
<220> FEATURE:
<223> OTHER INFORMATION: synthetic oligonucleotide

<400> SEQUENCE: 20
tactggaacc tagttgggcg agttacggac ctttcgtgca ggtcagta            48

<210> SEQ ID NO 21
<211> LENGTH: 40
<212> TYPE: DNA
<213> ORGANISM: Artificial Sequence
<220> FEATURE:
<223> OTHER INFORMATION: synthetic oligonucleotide

<400> SEQUENCE: 21
gaacctagtt gggcgagtta cggacctttc gtgcaggtca                     40

<210> SEQ ID NO 22
<211> LENGTH: 45
<212> TYPE: DNA
<213> ORGANISM: Artificial Sequence
<220> FEATURE:
<223> OTHER INFORMATION: synthetic oligonucleotide

<400> SEQUENCE: 22
tgaccgaacc tagttgggcg agttacggac ctttcgtgca ggtca               45

<210> SEQ ID NO 23
<211> LENGTH: 52
<212> TYPE: DNA
<213> ORGANISM: Artificial Sequence
<220> FEATURE:

<223> OTHER INFORMATION: synthetic oligonucleotide

<400> SEQUENCE: 23
gaacctagtt gggcgagtta cggatacacc attcaagcgg gacggaattt ac          52

<210> SEQ ID NO 24
<211> LENGTH: 62
<212> TYPE: DNA
<213> ORGANISM: Artificial Sequence
<220> FEATURE:
<223> OTHER INFORMATION: synthetic oligonucleotide

<400> SEQUENCE: 24
gtaaattccg gaacctagtt gggcgagtta cggatacacc attcaagcgg gacggaattt   60
ac                                                                  62

<210> SEQ ID NO 25
<211> LENGTH: 14
<212> TYPE: DNA
<213> ORGANISM: Artificial Sequence
<220> FEATURE:
<223> OTHER INFORMATION: synthetic oligonucleotide

<400> SEQUENCE: 25
cgccguucac cggg                                                     14

<210> SEQ ID NO 26
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 26
cgccguucac cggggcuuc                                                19

<210> SEQ ID NO 27
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 27
gcgaacgaca aggaauuucg c                                             21

<210> SEQ ID NO 28
<211> LENGTH: 52
<212> TYPE: DNA
<213> ORGANISM: Artificial Sequence
<220> FEATURE:
<223> OTHER INFORMATION: synthetic oligonucleotide

<400> SEQUENCE: 28
cgccguucac ccgggcuuct ttaaaaaaaa aaaaaaaaa aaaaaaaaaa aa             52

<210> SEQ ID NO 29
<211> LENGTH: 52
<212> TYPE: DNA
<213> ORGANISM: Artificial Sequence
<220> FEATURE:
<223> OTHER INFORMATION: synthetic oligonucleotide

<400> SEQUENCE: 29
cgccguucac uggggcuuct ttaaaaaaaa aaaaaaaaaa aaaaaaaaaa aa            52

<210> SEQ ID NO 30
<211> LENGTH: 54
<212> TYPE: DNA
<213> ORGANISM: Artificial Sequence
<220> FEATURE:
<223> OTHER INFORMATION: synthetic oligonucleotide

<400> SEQUENCE: 30
ctaattactg acctgcagta ggtaccgatg acgatcgtgc aggtcagtaa ttag         54

<210> SEQ ID NO 31
<211> LENGTH: 55
<212> TYPE: DNA
<213> ORGANISM: Artificial Sequence
<220> FEATURE:
<223> OTHER INFORMATION: synthetic oligonucleotide

<400> SEQUENCE: 31
aacagactcg gtcagtaggt accgatgacg acagcttgat ttcaccgagt ctgtt        55

<210> SEQ ID NO 32
<211> LENGTH: 57
<212> TYPE: DNA
<213> ORGANISM: Artificial Sequence
<220> FEATURE:
<223> OTHER INFORMATION: synthetic oligonucleotide

<400> SEQUENCE: 32
cguucacuau uggucucugc auucuuuaaa aaaaaaaaaa aaaaaaaaaa aaaaaaa      57

<210> SEQ ID NO 33
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 33
cagtaggtac cgatgacga                                                 19

<210> SEQ ID NO 34
<211> LENGTH: 61
<212> TYPE: DNA
<213> ORGANISM: Artificial Sequence
<220> FEATURE:
<223> OTHER INFORMATION: synthetic oligonucleotide

<400> SEQUENCE: 34
aatttaatac gactcactat agggagacca caaatagat tatataggac gacaagtaaa    60
a                                                                   61

<210> SEQ ID NO 35
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 35
cuauugucac uuccuugagu au                                             22

<210> SEQ ID NO 36
<211> LENGTH: 24
<212> TYPE: DNA

```
<213> ORGANISM: Artificial Sequence
<220> FEATURE:
<223> OTHER INFORMATION: synthetic oligonucleotide

<400> SEQUENCE: 36
gaccatgtcc caattcgcac cagg                                          24

<210> SEQ ID NO 37
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 37
ccacuugcga uguuuuaagu gg                                            22

<210> SEQ ID NO 38
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 38
tcgtgcaggt cagtadttag                                               20

<210> SEQ ID NO 39
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 39
cctttcgtgc aggtcagtad ttag                                          24

<210> SEQ ID NO 40
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 40
cagtaggtac cgatgacgat cgtgcaggtc agtadttag                          39

<210> SEQ ID NO 41
<211> LENGTH: 43
<212> TYPE: DNA
<213> ORGANISM: Artificial Sequence
<220> FEATURE:
<223> OTHER INFORMATION: synthetic oligonucleotide

<400> SEQUENCE: 41
cagtaggtac cgatgacgac ctttcgtgca ggtcagtadt tag                     43

<210> SEQ ID NO 42
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 42
acggcggccg taactataac ggtcctaagg                                    30
```

<210> SEQ ID NO 43
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 43
cagtaggtac cgatgacga                                              19

<210> SEQ ID NO 44
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 44
gaacctagtt gggcgagtta cgga                                        24

<210> SEQ ID NO 45
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 45
tacaccattc aagcgggacg gaatttac                                    28

<210> SEQ ID NO 46
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 46
gagacagtca agagatggtt aca                                         23

<210> SEQ ID NO 47
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 47
gagacagtca agagatggtt a                                           21

<210> SEQ ID NO 48
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 48
gagacagtca agagatgg                                               18

<210> SEQ ID NO 49
<211> LENGTH: 42
<212> TYPE: DNA
<213> ORGANISM: Artificial Sequence
<220> FEATURE:

<223> OTHER INFORMATION: synthetic oligonucleotide

<400> SEQUENCE: 49
cagtaggtac cgatgacgag agacagtcaa gagatggtta ca                              42

<210> SEQ ID NO 50
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 50
cagcttgatt tcaccgagtc tgtt                                                  24

<210> SEQ ID NO 51
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 51
ggcgttttca ccggcagct                                                        19

<210> SEQ ID NO 52
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 52
agccggcgtt ttcaccggca g                                                     21

<210> SEQ ID NO 53
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 53
ggtagccggc gttttcaccg gcag                                                  24

<210> SEQ ID NO 54
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 54
gtagccggcg ttttcaccgg c                                                     21

<210> SEQ ID NO 55
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 55
taatcgcggg tagccggcgt t                                                     21

```
<210> SEQ ID NO 56
<211> LENGTH: 43
<212> TYPE: DNA
<213> ORGANISM: Artificial Sequence
<220> FEATURE:
<223> OTHER INFORMATION: synthetic oligonucleotide

<400> SEQUENCE: 56
cagtaggtac cgatgacgac agcttgattt caccgagtct gtt            43

<210> SEQ ID NO 57
<211> LENGTH: 40
<212> TYPE: DNA
<213> ORGANISM: Artificial Sequence
<220> FEATURE:
<223> OTHER INFORMATION: synthetic oligonucleotide

<400> SEQUENCE: 57
cagtaggtac cgatgacgag tagccggcgt tttcaccggc                40

<210> SEQ ID NO 58
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 58
gccgagacag cgaagggatc a                                    21

<210> SEQ ID NO 59
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 59
gcagccgaga cagcgaaggg                                      20

<210> SEQ ID NO 60
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 60
aatttcaccg agtctgcagc c                                    21

<210> SEQ ID NO 61
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 61
aaatttcacc gagtctgcag cc                                   22

<210> SEQ ID NO 62
<211> LENGTH: 25
<212> TYPE: DNA
<213> ORGANISM: Artificial Sequence
<220> FEATURE:
<223> OTHER INFORMATION: synthetic oligonucleotide
```

```
<400> SEQUENCE: 62
ctaaaatttc accgagtctg cagcc                                          25

<210> SEQ ID NO 63
<211> LENGTH: 40
<212> TYPE: DNA
<213> ORGANISM: Artificial Sequence
<220> FEATURE:
<223> OTHER INFORMATION: synthetic oligonucleotide

<400> SEQUENCE: 63
cagtaggtac cgatgacgag ccgagacagc gaagggatca                          40

<210> SEQ ID NO 64
<211> LENGTH: 52
<212> TYPE: DNA
<213> ORGANISM: Artificial Sequence
<220> FEATURE:
<223> OTHER INFORMATION: synthetic oligonucleotide

<400> SEQUENCE: 64
caacagtttt ctcgcgcgtt ttaaaaaaaa aaaaaaaaaa aaaaaaaaaa aa            52

<210> SEQ ID NO 65
<211> LENGTH: 50
<212> TYPE: DNA
<213> ORGANISM: Artificial Sequence
<220> FEATURE:
<223> OTHER INFORMATION: synthetic oligonucleotide

<400> SEQUENCE: 65
acgtgtgttc gttctcggtt taaaaaaaaa aaaaaaaaaa aaaaaaaaaa               50

<210> SEQ ID NO 66
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 66
gttgacgtac cgtattga                                                  18

<210> SEQ ID NO 67
<211> LENGTH: 41
<212> TYPE: DNA
<213> ORGANISM: Artificial Sequence
<220> FEATURE:
<223> OTHER INFORMATION: synthetic oligonucleotide

<400> SEQUENCE: 67
gttgacgtac cgtattgaga gacagtcaag agatggttac a                        41

<210> SEQ ID NO 68
<211> LENGTH: 38
<212> TYPE: DNA
<213> ORGANISM: Artificial Sequence
<220> FEATURE:
<223> OTHER INFORMATION: synthetic oligonucleotide

<400> SEQUENCE: 68
gttgacgtac cgtattgatc gtgcaggtca gtaattag                            38

<210> SEQ ID NO 69
<211> LENGTH: 42
```

```
<212> TYPE: DNA
<213> ORGANISM: Artificial Sequence
<220> FEATURE:
<223> OTHER INFORMATION: synthetic oligonucleotide

<400> SEQUENCE: 69
gttgacgtac cgtattgaca gcttgatttc accgagtctg tt                          42

<210> SEQ ID NO 70
<211> LENGTH: 50
<212> TYPE: DNA
<213> ORGANISM: Artificial Sequence
<220> FEATURE:
<223> OTHER INFORMATION: synthetic oligonucleotide

<400> SEQUENCE: 70
agctgccggt gacagtaggt accgatgacg aggcgttttc accggcagct                  50

<210> SEQ ID NO 71
<211> LENGTH: 52
<212> TYPE: DNA
<213> ORGANISM: Artificial Sequence
<220> FEATURE:
<223> OTHER INFORMATION: synthetic oligonucleotide

<400> SEQUENCE: 71
tcgacggcca ctcagtaggt accgatgacg agtagccggc gttttcaccg gc               52

<210> SEQ ID NO 72
<211> LENGTH: 56
<212> TYPE: DNA
<213> ORGANISM: Artificial Sequence
<220> FEATURE:
<223> OTHER INFORMATION: synthetic oligonucleotide

<400> SEQUENCE: 72
gtgaaatttt agcagtaggt accgatgacg actaaaattt caccgagtct gcagcc           56

<210> SEQ ID NO 73
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 73
gttgacgtac cgtattgacc tttcgtgcag gtcagtagtt ag                          42

<210> SEQ ID NO 74
<211> LENGTH: 40
<212> TYPE: DNA
<213> ORGANISM: Artificial Sequence
<220> FEATURE:
<223> OTHER INFORMATION: synthetic oligonucleotide

<400> SEQUENCE: 74
gttgacgtac cgtattgatt tcgtgcaggt cagtagttag                             40

<210> SEQ ID NO 75
<211> LENGTH: 38
<212> TYPE: DNA
<213> ORGANISM: Artificial Sequence
<220> FEATURE:
<223> OTHER INFORMATION: synthetic oligonucleotide

<400> SEQUENCE: 75
```

```
gttgacgtac cgtattgatc gtgcaggtca gtagttag                              38

<210> SEQ ID NO 76
<211> LENGTH: 36
<212> TYPE: DNA
<213> ORGANISM: Artificial Sequence
<220> FEATURE:
<223> OTHER INFORMATION: synthetic oligonucleotide

<400> SEQUENCE: 76
gttgacgtac cgtattgagt gcaggtcagt agttag                               36

<210> SEQ ID NO 77
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 77
aatttaatac gactcactat agggaga                                         27
```

COMPOSITIONS AND METHODS FOR DETECTING NUCLEIC ACID FROM MOLLICUTES

CROSS REFERENCE TO RELATED APPLICATIONS

This application is a continuation of U.S. application Ser. No. 14/938,630, filed Nov. 11, 2015, which is continuation of U.S. application Ser. No. 12/821,608, filed Jun. 23, 2010, now U.S. Pat. No. 9,212,397, which claims the benefit of U.S. Provisional Application Ser. No. 61/219,674 filed on Jun. 23, 2009, the contents of each being incorporated herein by reference in their entirety.

INCORPORATION OF SEQUENCE LISTING

The sequence listing that is contained in the file named 525136_SeqListing_ST25.txt, which is 44 kilobytes (as measured in Microsoft Windows®) and was created on Jan. 24, 2019, is filed herewith by electronic submission and is incorporated by reference herein.

FIELD OF THE INVENTION

The field of the invention relates to amplification of nucleic acid from species of bacterium of the class Mollicutes.

BACKGROUND

Bacteria in the class Mollicutes are parasitic organisms commonly contaminating eukaryotic cell culture systems. Members of the Mollicutes are among the smallest and simplest of the prokaryotes. Because of their small size and lack of a rigid cell wall, Mollicutes pass easily through filters intended to remove bacterial contaminants. Mollicutes contamination of a cell culture is problematic because it can negatively impact cell growth, alter metabolism and lead to unsafe final products. Mollicutes compete with cultured cells for essential nutrients and produce toxins that can cause cell death, all of which can impact the quality and productivity of cell cultures. These organisms are therefore of significant concern to the biopharmaceutical industry, which is dependent on continuous cell culture for the production of drugs, vaccines, and other biologics.

Mollicutes include species from the genera *Mycoplasma*, *Acholeplasma* and *Spiroplasma*. Mollicutes can originate from mammalian, avian, insect, plant or fish cells. These organisms also have limited biosynthetic capabilities, making them dependent on external sources for essential nutrients and cofactors. Many species of Mollicutes have therefore evolved to become intracellular parasites. Thus, contaminating Mollicutes are present extracellularly and intracellulary in a host-cell environment.

Current culture methods for detection of Mollicutes are limited by the time required for the growth of these fastidious organisms. As a result, detection of Mollicutes using these methods can take 28 days or longer, a timeframe that is not compatible with today's fast pace of pharmaceutical manufacturing and distribution. Access to rapid, simple and relatively inexpensive methods for the detection of Mollicutes would enable the routine testing and proactive quality control of cell cultures, raw materials, equipment, fixtures and the like.

Compared to cell-culture methods, nucleic acid amplification tests are much more rapid detection methods. However, there is currently not a satisfactory nucleic acid amplification test available for detecting Mollicutes contamination of a cell-culture. Currently available nucleic acid amplification tests suffer from problems with identifying more than one or a few species of Mollicutes per assay. Further, for the assays that are designed to identify more than one species of Mollicutes, there are commonly problems with cross reactivity to related bacteria or nucleic acids that may be present in the sample. Further still, the currently available tests fail to detect some of the Mollicutes species known to contaminate and negatively impact cell cultures. Thus, there is a need in the art for an improved nucleic acid amplification test for identifying Mollicutes contamination.

SUMMARY

The present invention relates to compositions, reaction mixtures, kits and methods used in amplifying nucleic acids from various species of the class Mollicutes. Amplification reactions are uniplex reactions or, more preferably, are multiplex reactions. Amplified nucleic acids are then useful for a subsequent analysis. Subsequent analysis includes, amongst other types of analysis, nucleic acid detection, probe-based nucleic acid detection and real-time probe-based nucleic acid detection. In certain aspects and embodiments, particular regions of the 23S rRNA or gene encoding said rRNA have been identified as preferred targets for nucleic acid amplification reactions of a sample suspected containing at least one species of Mollicutes. Some oligomers comprise tag regions. Some oligomers comprise target closing regions, also referred to as tag-closing regions. Target closing regions have a nucleotide sequence that is substantially complementary to all or a portion of the target hybridizing region on the tagged amplification oligomer, thus allowing under certain conditions for the target closing region and the target hybridizing region to intramolecularly hybridize. The tagged oligomer is then considered to be in the closed/unavailable configuration. Some oligomers comprise promoter sequences. Some oligomers comprise binding moieties, such as homopolymeric and heteropolymeric nucleotide sequences. Compositions of the current invention comprise one or more separate oligomers useful in the amplification and detection of at least one species of Mollicutes. Samples can be from any source suspected of containing a species of the class Mollicutes. Preferred sample sources include bioreactors, cell lines, cell culture wares and pharmaceutical manufacturing wares, to name a few.

In one embodiment of the invention, there is provided a composition for determining the presence or absence of one or more *Mycoplasma* species in a sample, said composition comprising a tagged amplification oligomer comprising a target hybridizing region and a tag region, wherein said target hybridizing region is from 15 to 50 nucleobases in length and contains a nucleotide sequence that is configured to hybridize to a region of a target nucleic acid corresponding to residues 5065 to 5088 of SEQ ID NO:1.

In one aspect, said target-hybridizing region of said tagged amplification oligomer may contain one or more of a nucleotide addition, a nucleotide deletion, a nucleotide mismatch, a modified nucleotide or a combination thereof relative to a corresponding residue of said target nucleic acid. In another aspect, said target hybridizing region is from 20 to 24 nucleobases in length. In another aspect, said target hybridizing region comprises at least 95% sequence identity to SEQ ID NO:38. In another aspect said target hybridizing region comprises at least 95% sequence identity to SEQ ID NO:39.

In one aspect, said tag region of said tagged amplification oligomer is from 10 to 25 nucleobases in length. In another aspect, said tag region is from 18 to 24 nucleobases in length. In another aspect, said tag region is 19 nucleobases in length. In another aspect, said tag region contains a sequence that is substantially complementary to one of SEQ ID NO:13, SEQ ID NO:16 and SEQ ID NO:33. In another aspect, said tag region contains a sequence that is substantially identical to one of SEQ ID NO:13, SEQ ID NO:16 and SEQ ID NO:33. In another aspect, said tag region contains a nucleotide sequence selected from the group consisting of: a sequence with at least 95% identity to SEQ ID NO:43 or complement thereof; a sequence with at least 95% identity to SEQ ID NO:44 or complement thereof; a sequence with 100% identity to SEQ ID NO:43 or complement thereof; and a sequence with 100% identity to SEQ ID NO:44 or complement thereof.

In one aspect, said tagged amplification oligomer comprises at least 95% sequence identity to SEQ ID NO:40. In another aspect, said tagged amplification oligomer comprises at least 95% sequence identity to SEQ ID NO:41. In another aspect, said tagged amplification oligomer comprises at least 95% sequence identity to SEQ ID NO:17. In another aspect, said tagged amplification oligomer comprises 100% sequence identity to SEQ ID NO:17.

In one aspect, said tagged amplification oligomer further comprises a tag-closing region, said tag-closing region comprising a nucleotide sequence that is substantially complementary to a portion of said target hybridizing region of said tagged-amplification oligomer to allow for an intramolecular hybridization between the two regions under certain conditions. Preferably, the conditions are those that allow for the tagged oligomer to be in the closed position, while still allowing for steps of the reaction to be performed. In another aspect, said tag-closing region is 3 to 20 nucleobases in length.

In one aspect, said tagged amplification oligomer comprises at least 95% sequence identity to a sequence selected from the group consisting of SEQ ID NO:5, SEQ ID NO:18 and SEQ ID NO:30. In another aspect, said tagged amplification oligomer comprises 100% sequence identity to SEQ ID NO:5. In another aspect, said tagged amplification oligomer comprises 100% sequence identity to SEQ ID NO:18. In another aspect, said tagged amplification oligomer comprises 100% sequence identity to SEQ ID NO:30.

In one embodiment, said composition further comprises an additional oligomer comprising a target hybridizing region containing a nucleotide sequence that is configured to hybridize to a region of a target nucleic acid corresponding to residues 5003 to 5045 of SEQ ID NO:1, wherein said additional oligomer is selected from the group consisting of a blocker oligomer, a primer oligomer and a promoter-based amplification oligomer. In one aspect, said additional oligomer is a blocker oligomer. In another aspect, said additional oligomer is a blocker oligomer comprising a sequence that is at least 95% identical to SEQ ID NO:9. In another aspect, said additional oligomer is a blocker oligomer comprising a sequence that is at least 95% identical to SEQ ID NO:10. In another aspect, said additional oligomer is a blocker comprising a sequence that is SEQ ID NO:10. In one aspect, said additional oligomer is a promoter-based amplification oligomer. In another aspect, said additional oligomer is a promoter-based amplification oligomer comprising a target hybridizing region that is 10 to 50 nucleobases in length and contains a nucleotide sequence that is configured to hybridize to all or a portion of a region of a target nucleic acid corresponding to residues 5016 to 5045 of SEQ ID NO:1. In another aspect, said additional oligomer is a promoter-based amplification oligomer comprising a target hybridizing region comprising a sequence that is at least 95% identical to SEQ ID NO:42. In another aspect, said additional oligomer is a promoter-based amplification oligomer comprising a target hybridizing region comprising a sequence that is 100% identical to SEQ ID NO:42. In another aspect, said additional oligomer is a promoter-based amplification comprising a sequence that is at least 95% identical to SEQ ID NO:15. In another aspect, said additional oligomer is a promoter-based amplification oligomer comprising a sequence that is 100% identical to SEQ ID NO:15.

In one embodiment, said composition further comprises a tag-targeting amplification oligomer comprising a target hybridizing region that contains a nucleotide sequence configured to specifically hybridize to a tag region of said tagged amplification oligomer or complement thereof. In one aspect, said tag-targeting amplification oligomer comprises a target hybridization region that is 18 to 24 nucleobases in length. In another aspect, said tag-targeting amplification oligomer comprises a sequence that is at least 95% identical to a sequence selected from the group consisting of SEQ ID NO:13, SEQ ID NO:16 and SEQ ID NO:33. In another aspect, said tag-targeting amplification oligomer comprises a sequence that is 100% identical to SEQ ID NO:13. In another aspect, said tag-targeting amplification oligomer comprises a sequence that is 100% identical to SEQ ID NO:16. In another aspect, said tag-targeting amplification oligomer comprises a sequence that is 100% identical to SEQ ID NO:33.

In one embodiment, said composition further comprises a first tagged amplification oligomer comprising a target hybridizing region and a tag region, wherein said target hybridizing region is from 15 to 50 nucleobases in length and contains a nucleotide sequence that is configured to hybridize to a region of a target nucleic acid corresponding to residues 5065 to 5088 of SEQ ID NO:1, as is described above, and one or more additional tagged amplification oligomers. In one aspect, said one or more additional tagged amplification oligomers includes a tagged amplification oligomer comprising a nucleic acid sequence that is at least 95% identical to SEQ ID NO:6. In another aspect, said one or more additional tagged amplification oligomers includes a tagged amplification oligomer comprising a nucleic acid sequence that is at least 95% identical to SEQ ID NO:7. In another aspect, said one or more additional tagged amplification oligomers includes a tagged amplification oligomer comprising a nucleic acid sequence that is at least 95% identical to SEQ ID NO:8. In another aspect, said one or more additional tagged amplification oligomers includes a tagged amplification oligomer comprising a nucleic acid sequence that is 100% identical to SEQ ID NO:6. In another aspect, said one or more additional tagged amplification oligomers includes a tagged amplification oligomer comprising a nucleic acid sequence that is 100% identical to SEQ ID NO:7. In another aspect, said one or more additional tagged amplification oligomers includes a tagged amplification oligomer comprising a nucleic acid sequence that is 100% identical to SEQ ID NO:8. In another aspect, said one or more additional tagged amplification oligomers includes a first additional tagged amplification oligomer that is at least 95% identical to SEQ ID NO:6 and a second additional tagged amplification oligomer that is at least 95% identical to SEQ ID NO:7. In another aspect, said one or more additional tagged amplification oligomers includes a first additional tagged amplification oligomer that is at least 95% identical to SEQ ID NO:6 and a second additional tagged amplification oligomer that is at least 95% identical to SEQ ID NO:8. In another aspect, said one or more additional tagged amplification oligomers includes a first additional tagged amplification oligomer that is at least 95% identical to SEQ ID NO:7 and a second additional tagged amplification oligomer that is at least 95% identical to SEQ ID NO:8. In another aspect, said one or more additional tagged amplification oligomers includes a first additional tagged amplification oligomer that is at least 95% identical to SEQ ID NO:6, a second additional tagged amplification oligomer that is at least 95% identical to SEQ ID NO:7 and a third additional tagged amplification oligomer that is at least 95% identical to SEQ ID NO:8.

In one embodiment, said composition comprises at least two oligomers, one of which is a tagged amplification oligomer and the other of which is a blocker oligomer. In one aspect, said tagged amplification oligomer comprises a nucleotide sequence that is at least 95% identical to SEQ ID NO:5. In another aspect, said blocker oligomer comprises a nucleotide sequence that is at least 95% identical to SEQ ID NO:9. In another aspect, said blocker oligomer comprises a nucleotide sequence that is at least 95% identical to SEQ ID NO:10. In one aspect, said tagged amplification oligomer comprises a nucleotide sequence that is 100% identical to SEQ ID NO:5. In another aspect, said blocker oligomer comprises a nucleotide sequence that is 100% identical to SEQ ID NO:9. In another aspect, said blocker oligomer comprises a nucleotide sequence that is 100% identical to SEQ ID NO:10. In another aspect, said tagged amplification oligomer comprises a nucleotide sequence that is 100% identical to SEQ ID NO:5 and said blocker oligomer comprises a nucleotide sequence that is 100% identical to SEQ ID NO:9. In another aspect, said tagged amplification oligomer comprises a nucleotide sequence that is 100% identical to SEQ ID NO:5 and said blocker oligomer comprises a nucleotide sequence that is 100% identical to SEQ ID NO:10.

In one embodiment, said composition further comprises at least at least two additional oligomers, one of which is a tag-targeting oligomer, the other of which is a promoter based amplification oligomer. In one aspect, said tag-targeting amplification oligomer comprises a nucleotide sequence that is at least 95% identical to SEQ ID NO:13. In another aspect, said promoter-based amplification oligomer comprises a nucleotide sequence that is at least 95% identical to SEQ ID NO:15. In one aspect, said tag-targeting amplification oligomer comprises a nucleotide sequence that is 100% identical to SEQ ID NO:13. In another aspect, said promoter-based amplification oligomer comprises a nucleotide sequence that is 100% identical to SEQ ID NO:15. In another aspect, said tag-targeting amplification oligomer comprises a nucleotide sequence that is 100% identical to SEQ ID NO:13 and said promoter-based amplification oligomer comprises a nucleotide sequence that is 100% identical to SEQ ID NO:15.

In one embodiment, said composition comprises at least two oligomers, one of which is a tagged amplification oligomer comprising a target hybridizing region and a tag region, wherein said target hybridizing region is from 15 to 50 nucleobases in length and contains a nucleotide sequence that is configured to hybridize to a region of a target nucleic acid corresponding to residues 5065 to 5088 of SEQ ID NO:1, as is described above; and the others of which can be selected from the group consisting of: an additional tagged amplification oligomer; a blocker oligomer; a tag-targeting oligomer; and a promoter based amplification oligomer. In one aspect, said tagged amplification oligomer comprises a nucleotide sequence that is at least 95% identical to SEQ ID NO:5. In another aspect, said blocker oligomer comprises a nucleotide sequence that is at least 95% identical to SEQ ID NO:9. In another aspect, said blocker oligomer comprises a nucleotide sequence that is at least 95% identical to SEQ ID NO:10. In another aspect, said tag-targeting amplification oligomer comprises a nucleotide sequence that is at least 95% identical to SEQ ID NO:13. In another aspect, said promoter-based amplification oligomer comprises a nucleotide sequence that is at least 95% identical to SEQ ID NO:15. In another aspect, said additional tagged amplification oligomer comprises a nucleic acid sequence that is at least 95% identical to SEQ ID NO:6. In another aspect, said additional tagged amplification oligomer comprises a nucleic acid sequence that is at least 95% identical to SEQ ID NO:7. In another aspect, said additional tagged amplification oligomer comprises a nucleic acid sequence that is at least 95% identical to SEQ ID NO:8. In one aspect, said tagged amplification oligomer comprises a nucleotide sequence that is 100% identical to SEQ ID NO:5. In another aspect, said blocker oligomer comprises a nucleotide sequence that is 100% identical to SEQ ID NO:9. In another aspect, said blocker oligomer comprises a nucleotide sequence that is 100% identical to SEQ ID NO:10. In one aspect, said tag-targeting amplification oligomer comprises a nucleotide sequence that is 100% identical to SEQ ID NO:13. In another aspect, said promoter-based amplification oligomer comprises a nucleotide sequence that is 100% identical to SEQ ID NO:15. In another aspect, said tagged amplification oligomer comprises a nucleotide sequence that is 100% identical to SEQ ID NO:5, said blocker oligomer comprises a nucleotide sequence that is 100% identical to SEQ ID NO:9, said tag-targeting amplification oligomer comprises a nucleotide sequence that is 100% identical to SEQ ID NO:13, and said promoter-based amplification oligomer comprises a nucleotide sequence that is 100% identical to SEQ ID NO:15. In another aspect, said tagged amplification oligomer comprises a nucleotide sequence that is 100% identical to SEQ ID NO:5, said blocker oligomer comprises a nucleotide sequence that is 100% identical to SEQ ID NO:10, said tag-targeting amplification oligomer comprises a nucleotide sequence that is 100% identical to SEQ ID NO:13, and said promoter-based amplification oligomer comprises a nucleotide sequence that is 100% identical to SEQ ID NO:15. In another aspect, said additional tagged amplification oligomer comprises a nucleic acid sequence that is 100% identical to SEQ ID NO:6. In another aspect, said additional tagged amplification oligomer comprises a nucleic acid sequence that is 100% identical to SEQ ID NO:7. In another aspect, said additional tagged amplification oligomer comprises a nucleic acid sequence that is 100% identical to SEQ ID NO:8.

In one embodiment, there is a reaction mixture for generating from one or more *Mycoplasma* species in a sample an initial nucleic acid amplification product containing a tag sequence or complement thereof, wherein said reaction mixture comprises a tagged amplification oligomer comprising a target hybridizing region and a tag region, wherein said target hybridizing region is from 15 to 50 nucleobases in length and contains a nucleotide sequence that is configured to hybridize to a region of a target nucleic acid corresponding to residues 5065 to 5088 of SEQ ID NO:1. In one aspect, said initial amplification product comprises a tag sequence that is from 10 to 25 nucleobases in length. In another aspect said initial amplification product comprises a tag sequence that is from 18 to 24 nucleobases in length. In another aspect, said initial amplification product comprises a tag sequence that is 19 nucleobases in length. In another aspect, said initial amplification product comprises a tag sequence that contains a sequence that is substantially complementary to one of SEQ ID NO:13, SEQ ID NO:16 and SEQ ID NO:33. In another aspect, said initial amplification product comprises a tag sequence that contains a sequence that is substantially identical to one of SEQ ID NO:13, SEQ ID NO:16 and SEQ ID NO:33. In another aspect, said initial amplification product comprises a tag sequence that contains a nucleotide sequence selected from the group consisting of: a sequence with at least 95% identity to SEQ ID NO:43 or complement thereof; a sequence with at least 95% identity to SEQ ID NO:44 or complement thereof; a sequence with 100% identity to SEQ ID NO:43 or complement thereof; and a sequence with 100% identity to SEQ ID NO:44 or complement thereof.

In one embodiment, there is an amplification reaction mixture for generating from an initial nucleic acid amplification product containing a tag sequence or complement thereof, as described above, a further nucleic acid amplification product, wherein said amplification reaction mixture comprises a tag-targeting amplification oligomer comprising a target hybridizing region containing a nucleic acid sequence configured to specifically hybridize to said tag sequence, or complement thereof, that contained within the nucleotide sequence of said initial nucleic acid amplification product, and wherein said amplification reaction mixture comprises a promoter-based amplification oligomer comprising a target hybridizing region that is 10 to 50 nucleobases in length and contains a nucleotide sequence that is configured to hybridize to all or a portion of a region of a target nucleic acid corresponding to residues 5016 to 5045 of SEQ ID NO:1.

In one aspect, said target hybridizing region of said promoter-based amplification oligomer comprises a sequence that is at least 95% identical to SEQ ID NO:42. In another aspect, said target hybridizing region of said promoter-based amplification oligomer comprises a sequence that is 100% identical to SEQ ID NO:42. In another aspect, said promoter-based amplification oligomer comprising a sequence that is 100% identical to SEQ ID NO:15. In another aspect, said target hybridizing region of said tag-targeting amplification oligomer is 18 to 24 nucleobases in length. In another aspect, said tag-targeting amplification oligomer comprises a sequence that is at least 95% identical to a sequence selected from the group consisting of: SEQ ID NO:13, SEQ ID NO:16 and SEQ ID NO:33. In another aspect, said tag-targeting amplification oligomer comprises a sequence that is 100% identical to a sequence selected from the group consisting of: SEQ ID NO:13, SEQ ID NO:16 and SEQ ID NO:33.

In one aspect, there is provided an initial amplification product generated using a tagged amplification oligomer comprising a target hybridizing region and a tag region, wherein said target hybridizing region is from 15 to 50 nucleobases in length and contains a nucleotide sequence that is configured to hybridize to a region of a target nucleic acid corresponding to residues 5065 to 5088 of SEQ ID NO:1, wherein said initial amplification product contains a nucleotide sequence comprising a tag sequence region, and wherein said tag sequence is from 10 to 25 nucleobases in length. In another aspect said initial amplification product comprises a tag sequence that is from 18 to 24 nucleobases in length. In another aspect, said initial amplification product comprises a tag sequence that is 19 nucleobases in length. In another aspect, said initial amplification product comprises a tag sequence that contains a sequence that is substantially complementary to one of SEQ ID NO:13, SEQ ID NO:16 and SEQ ID NO:33. In another aspect, said initial amplification product comprises a tag sequence that contains a sequence that is substantially identical to one of SEQ ID NO:13, SEQ ID NO:16 and SEQ ID NO:33. In another aspect, said initial amplification product comprises a tag sequence that contains a nucleotide sequence selected from the group consisting of: a sequence with at least 95% identity to SEQ ID NO:43 or complement thereof; a sequence with at least 95% identity to SEQ ID NO:44 or complement thereof; a sequence with 100% identity to SEQ ID NO:43 or complement thereof; and a sequence with 100% identity to SEQ ID NO:44 or complement thereof.

In one aspect, there is provided an amplification product generated from said initial amplification product and containing a nucleotide sequence comprising a tag sequence region, wherein the sequence of said tag region is from 10 to 25 nucleobases in length. In another aspect said tag sequence region is from 18 to 24 nucleobases in length. In another aspect, said initial amplification product comprises a tag sequence that is 19 nucleobases in length. In another aspect, said tag sequence region contains a sequence that is substantially complementary to one of SEQ ID NO:13, SEQ ID NO:16 and SEQ ID NO:33. In another aspect, said tag sequence region contains a sequence that is substantially identical to one of SEQ ID NO:13, SEQ ID NO:16 and SEQ ID NO:33. In another aspect, a tag sequence region contains a nucleotide sequence selected from the group consisting of: a sequence with at least 95% identity to SEQ ID NO:43 or complement thereof; a sequence with at least 95% identity to SEQ ID NO:44 or complement thereof; a sequence with 100% identity to SEQ ID NO:43 or complement thereof; and a sequence with 100% identity to SEQ ID NO:44 or complement thereof.

In one embodiment, there is provided a method for the in vitro amplification of a nucleic acid from one or more *Mycoplasma* species in a sample, comprising the steps of: (a.) contacting a sample with a tagged amplification oligomer comprising a target hybridizing region and a tag region, wherein said target hybridizing region is from 15 to 50 nucleobases in length and contains a nucleotide sequence that is configured to specifically hybridize to a region of a target nucleic acid corresponding to residues 5065 to 5088 of SEQ ID NO:1; and (b.) providing suitable conditions for performing an amplification reaction.

In one aspect said nucleotide sequence contained within said tagged amplification oligomer target hybridizing region has at least one of a nucleotide addition, a nucleotide deletion, a nucleotide mismatch, a modified nucleotide or a combination thereof relative to a corresponding residue of said target nucleic acid. In another aspect, said target hybridizing region of said tagged amplification oligomer is from 20 to 24 nucleobases in length. In another aspect, said target hybridizing region of said tagged amplification oligomer comprises at least 95% sequence identity to SEQ ID NO:38. In another aspect, said target hybridizing region of said tagged amplification oligomer comprises at least 95% sequence identity to SEQ ID NO:39.

In one aspect, said tag region of said tagged amplification oligomer is from 10 to 25 nucleobases in length. In another aspect, said tag region is from 18 to 24 nucleobases in length. In another aspect, said tag region is 19 nucleobases in length. In another aspect, said tag region contains a sequence that is substantially complementary to one of SEQ ID NO:13, SEQ ID NO:16 and SEQ ID NO:33. In another aspect, said tag region contains a sequence that is substantially identical to one of SEQ ID NO:13, SEQ ID NO:16 and SEQ ID NO:33. In another aspect, said tag region contains a nucleotide sequence selected from the group consisting of: a sequence with at least 95% identity to SEQ ID NO:43 or complement thereof; a sequence with at least 95% identity to SEQ ID NO:44 or complement thereof; a sequence with 100% identity to SEQ ID NO:43 or complement thereof; and a sequence with 100% identity to SEQ ID NO:44 or complement thereof. In one aspect, said tagged amplification oligomer comprises at least 95% sequence identity to SEQ ID NO:40. In another aspect, said tagged amplification oligomer comprises at least 95% sequence identity to SEQ ID NO:41. In another aspect, said tagged amplification oligomer comprises at least 95% sequence identity to SEQ ID NO:17. In another aspect, said tagged amplification oligomer comprises 100% sequence identity to SEQ ID NO:17.

In one aspect, said tagged amplification oligomer further comprises a tag-closing region, said tag-closing region comprising a nucleotide sequence that is substantially complementary to a portion of said target hybridizing region of said tagged-amplification oligomer to allow for an intramolecular hybridization between the two regions under certain conditions. Preferably, the conditions are those that allow for the tagged oligomer to be in the closed position, while still allowing for steps of the reaction to be performed. In another aspect, said tag-closing region is 3 to 20 nucleobases in length.

In one aspect, said tagged amplification oligomer comprises at least 95% sequence identity to a sequence selected from the group consisting of SEQ ID NO:5, SEQ ID NO:18 and SEQ ID NO:30. In another aspect, said tagged amplification oligomer comprises 100% sequence identity to SEQ ID NO:5. In another aspect, said tagged amplification oligomer comprises 100% sequence identity to SEQ ID NO:18. In another aspect, said tagged amplification oligomer comprises 100% sequence identity to SEQ ID NO:30.

In one aspect, said method further comprises the step of contacting said sample with an additional oligomer. In another aspect, said additional oligomer is a blocker oligomer. In another aspect, said additional oligomer is a blocker oligomer comprising a sequence that is at least 95% identical to SEQ ID NO:9. In another aspect, said additional oligomer is a blocker oligomer comprising a sequence that is at least 95% identical to SEQ ID NO:10. In another aspect, said additional oligomer is a blocker comprising a sequence that is SEQ ID NO:10.

In one aspect, said method comprises contacting said sample with a tagged amplification oligomer with a nucleotide sequence that is at least 95% identical to SEQ ID NO:5, a nucleotide sequence that is at least 95% identical to SEQ ID NO:17, a nucleotide sequence that is at least 95% identical to SEQ ID NO:18, a nucleotide sequence that is at least 95% identical to SEQ ID NO:30, a nucleotide sequence that is 100% identical to SEQ ID NO:5, a nucleotide sequence that is 100% identical to SEQ ID NO:17, a nucleotide sequence that is 100% identical to SEQ ID NO:18, a nucleotide sequence that is 100% identical to SEQ ID NO:30, a nucleotide sequence that is 100% identical to SEQ ID NO:40, or a nucleotide sequence that is 100% identical to SEQ ID NO:41; and wherein said contacting step further comprises contacting said sample with a blocker oligomer. In another aspect, said blocker oligomer comprises a sequence that is at least 95% identical to SEQ ID NO:9. In another aspect, said blocker oligomer comprises a sequence that is at least 95% identical to SEQ ID NO:10. In another aspect, said blocker comprises a sequence that is SEQ ID NO:10.

In one aspect, said method at step (b.) results in an initial amplification product containing a tag sequence, or complement thereof. In another aspect, there is provided an initial amplification product with a nucleotide sequence comprising a tag sequence region, wherein said tag sequence is from 10 to 25 nucleobases in length. In another aspect said initial amplification product comprises a tag sequence that is from 18 to 24 nucleobases in length. In another aspect, said initial amplification product comprises a tag sequence that is 19 nucleobases in length. In another aspect, said initial amplification product comprises a tag sequence that contains a sequence that is substantially complementary to one of SEQ ID NO:13, SEQ ID NO:16 and SEQ ID NO:33. In another aspect, said initial amplification product comprises a tag sequence that contains a sequence that is substantially identical to one of SEQ ID NO:13, SEQ ID NO:16 and SEQ ID NO:33. In another aspect, said initial amplification product comprises a tag sequence that contains a nucleotide sequence selected from the group consisting of: a sequence with at least 95% identity to SEQ ID NO:43 or complement thereof; a sequence with at least 95% identity to SEQ ID NO:44 or complement thereof; a sequence with 100% identity to SEQ ID NO:43 or complement thereof; and a sequence with 100% identity to SEQ ID NO:44 or complement thereof. In one aspect, said initial amplification product has a 3' end defined by a blocker oligomer. In another aspect, said initial amplification product has a 3' end that is not defined by a blocker oligomer.

In one embodiment of the current invention, there is provided a method for the in vitro amplification of an initial amplification product, comprising the steps of (c.) contacting the sample with at least one additional amplification oligomer selected from the group consisting of a tag-targeting amplification oligomer, a primer oligomer and a promoter-based amplification oligomer; and (d.) providing suitable conditions for performing a second amplification reaction. In one aspect, the oligomers of step (c.) and the oligomers of step (a.) are contacted to said sample at the same time point. In one aspect, the oligomers of step (c.) and the oligomers of step (a.) are contacted to the sample and a single amplification reaction is performed. In this aspect, steps (b.) and (d.) are combined to provide suitable conditions for performing an amplification reaction to generate an initial amplification product and for performing an amplification reaction generate a second amplification product therefrom. Though all of the amplification oligomers are present in this combined amplification reaction aspect, the tag-targeting amplification oligomers are configured to not participate in amplification until a tagged amplification oligomer is incorporated into an initial amplification product. In another aspect, the oligomers of step (c.) and the oligomers of step (a.) are contacted to said sample at separate time points. In one aspect, the method comprises the step of (c.) providing to an amplification product generated in step (b.) a second reaction mixture comprising a tag-targeting amplification oligomer consisting essentially of a target hybridizing region that contains a nucleotide sequence configured to specifically hybridize to a tag region of said tagged amplification oligomer, and comprising a second amplification oligomer; and (d.) providing suitable conditions for performing a second amplification reaction.

In one aspect for generating an amplification product, said sample is contacted with a first additional amplification oligomer that is a tag-targeting amplification oligomer comprising a target hybridizing region that contains a nucleotide sequence configured to specifically hybridize to a tag region of said, or complement thereof in an initial amplification oligomer, and is contacted with a second additional amplification oligomer. In another aspect, said tag-targeting amplification oligomer comprises a target hybridization region that is 18 to 24 nucleobases in length. In another aspect, said tag-targeting amplification oligomer comprises a sequence that is at least 95% identical to a sequence selected from the group consisting of SEQ ID NO:13, SEQ ID NO:16 and SEQ ID NO:33. In another aspect, said tag-targeting amplification oligomer comprises a sequence that is 100% identical to SEQ ID NO:13. In another aspect, said tag-targeting amplification oligomer comprises a sequence that is 100% identical to SEQ ID NO:16. In another aspect, said tag-targeting amplification oligomer comprises a sequence that is 100% identical to SEQ ID NO:33. In one aspect, said second amplification oligomer is a primer amplification oligomer, a promoter based amplification oligomer or a tagged amplification oligomer. In another aspect, said second amplification oligomer is a promoter-based amplification oligomer comprising a target hybridizing region that is 10 to 50 nucleobases in length and contains a nucleotide sequence that is configured to hybridize to all or a portion of a region of a target nucleic acid corresponding to residues 5016 to 5045 of SEQ ID NO:1. In another aspect, said second additional amplification oligomer is a promoter-based amplification oligomer comprising a target hybridizing region that comprises a sequence that is at least 95% identical to SEQ ID NO:42. In another aspect, said second additional amplification oligomer is a promoter-based amplification oligomer that comprises a sequence that is 100% identical to SEQ ID NO:42. In another aspect, said second additional amplification oligomer is a promoter-based amplification oligomer that comprises a sequence that is 100% identical to SEQ ID NO:15.

In one aspect for the in vitro amplification of a nucleic acid from one or more *Mycoplasma* species in a sample, there is provided at least one tagged amplification oligomer that is at least 95% identical to SEQ ID NO:5; at least one blocker oligomer that is at least 95% identical to SEQ ID NO:10; at least one tag-targeting amplification oligomer that is at least 95% identical to SEQ ID NO:13 and at least one promoter-based amplification oligomer that is at least 95% identical to SEQ ID NO:15. In another aspect, said at least one tagged amplification oligomer is 100% identical to SEQ ID NO:5. In another aspect, said at least one blocker oligomer is 100% identical to SEQ ID NO:10. In another aspect, said at least one tag-targeting amplification oligomer is 100% identical to SEQ ID NO:13. In another aspect, said at least one promoter-based amplification oligomer is 95% identical to SEQ ID NO:15. In another aspect there are provided one or more additional tagged amplification oligomers each or which could be selected from the group consisting of: a tagged amplification oligomer with at least 95% identity to SEQ ID NO:6; a tagged amplification oligomer with at least 95% identity to SEQ ID NO:7, a tagged amplification oligomer with at least 95% identity to SEQ ID NO:8, a tagged amplification oligomer with 100% identity to SEQ ID NO:6, a tagged amplification oligomer with 100% identity to SEQ ID NO:7 and a tagged amplification oligomer with 100% identity to SEQ ID NO:8.

In one embodiment there is further provided an analysis step, wherein an initial amplification product, an amplification product or both are analyzed. In one aspect, said analysis comprises a detection step to identify the presence or absence of an initial amplification product from an amplification reaction in step (b.), an amplification product generated in step (d.) or both initial amplification and amplification products generated in steps (b.) and (d.). In another aspect, said detection step is a probe-based detection step. In another aspect, said probe-based detection step uses a probe with a nucleotide sequence that is at least 95% identical to SEQ ID NO:14. In another aspect, said detection step is a probe-based detection step. In another aspect, said probe-based detection step uses a probe with a nucleotide sequence that is 100% identical to SEQ ID NO:14.

In one embodiment of the invention, there is provided a composition for determining the presence or absence of one or more *Mycoplasma* species in a sample, said composition comprising a tagged amplification oligomer comprising a target hybridizing region and a tag region, wherein said target hybridizing region is from 15 to 50 nucleobases in length and contains a nucleotide sequence that is configured to hybridize to a region of a target nucleic acid corresponding to residues 4752 to 4798 of SEQ ID NO:2.

In one aspect, said target-hybridizing region of said tagged amplification oligomer may contain one or more of a nucleotide addition, a nucleotide deletion, a nucleotide mismatch, a modified nucleotide or a combination thereof relative to a corresponding residue of said target nucleic acid. In another aspect, said target hybridizing region is from 18 to 28 nucleobases in length. In another aspect, said target hybridizing region comprises at least 95% sequence identity to SEQ ID NO:45. In another aspect, said target hybridizing region comprises at least 95% sequence identity to SEQ ID NO:46. In another aspect, said target hybridizing region comprises at least 95% sequence identity to SEQ ID NO:47. In another aspect, said target hybridizing region comprises at least 95% sequence identity to SEQ ID NO:48. In another aspect, said target hybridizing region is 15 to 30 nucleobases in length and contains a nucleotide sequence that is configured to hybridize to a region of a target nucleic acid corresponding to residues 4776 to 4798 of SEQ ID NO:2.

In one aspect, said tag region of said tagged amplification oligomer is from 10 to 25 nucleobases in length. In another aspect, said tag region is from 18 to 24 nucleobases in length. In another aspect, said tag region is 19 nucleobases in length. In another aspect, said tag region contains a sequence that is substantially complementary to one of SEQ ID NO:13, SEQ ID NO:16 and SEQ ID NO:33. In another aspect, said tag region contains a sequence that is substantially identical to one of SEQ ID NO:13, SEQ ID NO:16 and SEQ ID NO:33. In another aspect, said tag region contains a nucleotide sequence selected from the group consisting of: a sequence with at least 95% identity to SEQ ID NO:43 or complement thereof; a sequence with at least 95% identity to SEQ ID NO:44 or complement thereof; a sequence with 100% identity to SEQ ID NO:43 or complement thereof; and a sequence with 100% identity to SEQ ID NO:44 or complement thereof.

In one aspect, said tagged amplification oligomer comprises at least 95% sequence identity to SEQ ID NO:23. In another aspect, said tagged amplification oligomer comprises at least 95% sequence identity to SEQ ID NO:49. In another aspect, said tagged amplification oligomer comprises 100% sequence identity to SEQ ID NO:23.

In one aspect, said tagged amplification oligomer further comprises a tag-closing region, said tag-closing region comprising a nucleotide sequence that is substantially complementary to a portion of said target hybridizing region of said tagged-amplification oligomer to allow for an intramolecular hybridization between the two regions under certain conditions. Preferably, the conditions are those that allow for the tagged oligomer to be in the closed position, while still allowing for steps of the reaction to be performed. In another aspect, said tag-closing region is 3 to 20 nucleobases in length.

In one aspect, said tagged amplification oligomer comprises at least 95% sequence identity to a sequence selected from the group consisting of: SEQ ID NO:6 and SEQ ID NO:24. In another aspect, said tagged amplification oligomer comprises 100% sequence identity to SEQ ID NO:6. In another aspect, said tagged amplification oligomer comprises 100% sequence identity to SEQ ID NO:24.

In one embodiment, said composition further comprises an additional oligomer comprising a target hybridizing region containing a nucleotide sequence that is configured to hybridize to a region of a target nucleic acid corresponding to residues 4690 to 4732 of SEQ ID NO:2, wherein said additional oligomer is selected from the group consisting of a blocker oligomer, a primer oligomer and a promoter-based amplification oligomer. In one aspect, said additional oligomer is a blocker oligomer. In another aspect, said additional oligomer is a blocker oligomer comprising a sequence that is at least 95% identical to SEQ ID NO:9. In another aspect, said additional oligomer is a blocker oligomer comprising a sequence that is at least 95% identical to SEQ ID NO:10. In another aspect, said additional oligomer is a blocker comprising a sequence that is SEQ ID NO:10. In one aspect, said additional oligomer is a promoter-based amplification oligomer. In another aspect, said additional oligomer is a promoter-based amplification oligomer comprising a target hybridizing region that is 10 to 50 nucleobases in length and contains a nucleotide sequence that is configured to hybridize to all or a portion of a region of a target nucleic acid corresponding to residues 4703 to 4732 of SEQ ID NO:2. In another aspect, said additional oligomer is a promoter-based amplification oligomer comprising a target hybridizing region comprising a sequence that is at least 95% identical to SEQ ID NO:42. In another aspect, said additional oligomer is a promoter-based amplification oligomer comprising a target hybridizing region comprising a sequence that is 100% identical to SEQ ID NO:42. In another aspect, said additional oligomer is a promoter-based amplification comprising a sequence that is at least 95% identical to SEQ ID NO:15. In another aspect, said additional oligomer is a promoter-based amplification oligomer comprising a sequence that is 100% identical to SEQ ID NO:15.

In one embodiment, said composition further comprises a tag-targeting amplification oligomer comprising a target hybridizing region that contains a nucleotide sequence configured to specifically hybridize to a tag region of said tagged amplification oligomer or complement thereof. In one aspect, said tag-targeting amplification oligomer comprises a target hybridization region that is 18 to 24 nucleobases in length. In another aspect, said tag-targeting amplification oligomer comprises a sequence that is at least 95% identical to a sequence selected from the group consisting of SEQ ID NO:13, SEQ ID NO:16 and SEQ ID NO:33. In another aspect, said tag-targeting amplification oligomer comprises a sequence that is 100% identical to SEQ ID NO:13. In another aspect, said tag-targeting amplification oligomer comprises a sequence that is 100% identical to SEQ ID NO:16. In another aspect, said tag-targeting amplification oligomer comprises a sequence that is 100% identical to SEQ ID NO:33.

In one embodiment, said composition further comprises a first tagged amplification oligomer comprising a target hybridizing region and a tag region, wherein said target hybridizing region is from 15 to 50 nucleobases in length and contains a nucleotide sequence that is configured to hybridize to a region of a target nucleic acid corresponding to residues 4752 to 4798 of SEQ ID NO:2, as is described above, and one or more additional tagged amplification oligomers. In one aspect, said one or more additional tagged amplification oligomers includes a tagged amplification oligomer comprising a nucleic acid sequence that is at least 95% identical to SEQ ID NO:5. In another aspect, said one or more additional tagged amplification oligomers includes a tagged amplification oligomer comprising a nucleic acid sequence that is at least 95% identical to SEQ ID NO:7. In another aspect, said one or more additional tagged amplification oligomers includes a tagged amplification oligomer comprising a nucleic acid sequence that is at least 95% identical to SEQ ID NO:8. In another aspect, said one or more additional tagged amplification oligomers includes a tagged amplification oligomer comprising a nucleic acid sequence that is 100% identical to SEQ ID NO:5. In another aspect, said one or more additional tagged amplification oligomers includes a tagged amplification oligomer comprising a nucleic acid sequence that is 100% identical to SEQ ID NO:7. In another aspect, said one or more additional tagged amplification oligomers includes a tagged amplification oligomer comprising a nucleic acid sequence that is 100% identical to SEQ ID NO:8. In another aspect, said one or more additional tagged amplification oligomers includes a first additional tagged amplification oligomer that is at least 95% identical to SEQ ID NO:5 and a second additional tagged amplification oligomer that is at least 95% identical to SEQ ID NO:7. In another aspect, said one or more additional tagged amplification oligomers includes a first additional tagged amplification oligomer that is at least 95% identical to SEQ ID NO:5 and a second additional tagged amplification oligomer that is at least 95% identical to SEQ ID NO:8. In another aspect, said one or more additional tagged amplification oligomers includes a first additional tagged amplification oligomer that is at least 95% identical to SEQ ID NO:7 and a second additional tagged amplification oligomer that is at least 95% identical to SEQ ID NO:8. In another aspect, said one or more additional tagged amplification oligomers includes a first additional tagged amplification oligomer that is at least 95% identical to SEQ ID NO: 5, a second additional tagged amplification oligomer that is at least 95% identical to SEQ ID NO:7 and a third additional tagged amplification oligomer that is at least 95% identical to SEQ ID NO:8.

In one embodiment, said composition comprises at least two oligomers, one of which is a tagged amplification oligomer and the other of which is a blocker oligomer. In one aspect, said tagged amplification oligomer comprises a nucleotide sequence that is at least 95% identical to SEQ ID NO:6. In another aspect, said blocker oligomer comprises a nucleotide sequence that is at least 95% identical to SEQ ID NO:9. In another aspect, said blocker oligomer comprises a nucleotide sequence that is at least 95% identical to SEQ ID NO:10. In one aspect, said tagged amplification oligomer comprises a nucleotide sequence that is 100% identical to SEQ ID NO:6. In another aspect, said blocker oligomer comprises a nucleotide sequence that is 100% identical to SEQ ID NO:9. In another aspect, said blocker oligomer comprises a nucleotide sequence that is 100% identical to SEQ ID NO:10. In another aspect, said tagged amplification oligomer comprises a nucleotide sequence that is 100% identical to SEQ ID NO:6 and said blocker oligomer comprises a nucleotide sequence that is 100% identical to SEQ ID NO:9. In another aspect, said tagged amplification oligomer comprises a nucleotide sequence that is 100% identical to SEQ ID NO:6 and said blocker oligomer comprises a nucleotide sequence that is 100% identical to SEQ ID NO:10.

In one embodiment, said composition further comprises at least two additional oligomers, one of which is a tag-targeting oligomer, the other of which is a promoter based amplification oligomer. In one aspect, said tag-targeting amplification oligomer comprises a nucleotide sequence that is at least 95% identical to SEQ ID NO:13. In another aspect, said promoter-based amplification oligomer comprises a nucleotide sequence that is at least 95% identical to SEQ ID NO:15. In one aspect, said tag-targeting amplification oligomer comprises a nucleotide sequence that is 100% identical to SEQ ID NO:13. In another aspect, said promoter-based amplification oligomer comprises a nucleotide sequence that is 100% identical to SEQ ID NO:15. In another aspect, said tag-targeting amplification oligomer comprises a nucleotide sequence that is 100% identical to SEQ ID NO:13 and said promoter-based amplification oligomer comprises a nucleotide sequence that is 100% identical to SEQ ID NO:15.

In one embodiment, said composition comprises at least two oligomers, one of which is a tagged amplification oligomer comprising a target hybridizing region and a tag region, wherein said target hybridizing region is from 15 to 50 nucleobases in length and contains a nucleotide sequence that is configured to hybridize to a region of a target nucleic acid corresponding to residues 4752 to 4798 of SEQ ID NO:2, as is described above; and the others of which can be selected from the group consisting of: an additional tagged amplification oligomer; a blocker oligomer; a tag-targeting oligomer; and a promoter based amplification oligomer. In one aspect, said tagged amplification oligomer comprises a nucleotide sequence that is at least 95% identical to SEQ ID NO:6. In another aspect, said blocker oligomer comprises a nucleotide sequence that is at least 95% identical to SEQ ID NO:9. In another aspect, said blocker oligomer comprises a nucleotide sequence that is at least 95% identical to SEQ ID NO:10. In another aspect, said tag-targeting amplification oligomer comprises a nucleotide sequence that is at least 95% identical to SEQ ID NO:13. In another aspect, said promoter-based amplification oligomer comprises a nucleotide sequence that is at least 95% identical to SEQ ID NO:15. In another aspect, said additional tagged amplification oligomer comprises a nucleic acid sequence that is at least 95% identical to SEQ ID NO:5. In another aspect, said additional tagged amplification oligomer comprises a nucleic acid sequence that is at least 95% identical to SEQ ID NO:7. In another aspect, said additional tagged amplification oligomer comprises a nucleic acid sequence that is at least 95% identical to SEQ ID NO:8. In one aspect, said tagged amplification oligomer comprises a nucleotide sequence that is 100% identical to SEQ ID NO:6. In another aspect, said blocker oligomer comprises a nucleotide sequence that is 100% identical to SEQ ID NO:9. In another aspect, said blocker oligomer comprises a nucleotide sequence that is 100% identical to SEQ ID NO:10. In one aspect, said tag-targeting amplification oligomer comprises a nucleotide sequence that is 100% identical to SEQ ID NO:13. In another aspect, said promoter-based amplification oligomer comprises a nucleotide sequence that is 100% identical to SEQ ID NO:15. In another aspect, said tagged amplification oligomer comprises a nucleotide sequence that is 100% identical to SEQ ID NO:6, said blocker oligomer comprises a nucleotide sequence that is 100% identical to SEQ ID NO:9, said tag-targeting amplification oligomer comprises a nucleotide sequence that is 100% identical to SEQ ID NO:13, and said promoter-based amplification oligomer comprises a nucleotide sequence that is 100% identical to SEQ ID NO:15. In another aspect, said tagged amplification oligomer comprises a nucleotide sequence that is 100% identical to SEQ ID NO:6, said blocker oligomer comprises a nucleotide sequence that is 100% identical to SEQ ID NO:10, said tag-targeting amplification oligomer comprises a nucleotide sequence that is 100% identical to SEQ ID NO:13, and said promoter-based amplification oligomer comprises a nucleotide sequence that is 100% identical to SEQ ID NO:15. In another aspect, said additional tagged amplification oligomer comprises a nucleic acid sequence that is 100% identical to SEQ ID NO:5. In another aspect, said additional tagged amplification oligomer comprises a nucleic acid sequence that is 100% identical to SEQ ID NO:7. In another aspect, said additional tagged amplification oligomer comprises a nucleic acid sequence that is 100% identical to SEQ ID NO:8.

In one embodiment, there is a reaction mixture for generating from one or more *Mycoplasma* species in a sample an initial nucleic acid amplification product containing a tag sequence or complement thereof, wherein said reaction mixture comprises a tagged amplification oligomer comprising a target hybridizing region and a tag region, wherein said target hybridizing region is from 15 to 50 nucleobases in length and contains a nucleotide sequence that is configured to hybridize to a region of a target nucleic acid corresponding to residues 4752 to 4798 of SEQ ID NO:2, as is described above. In one aspect, said initial amplification product comprises a tag sequence that is from 10 to 25 nucleobases in length. In another aspect said initial amplification product comprises a tag sequence that is from 18 to 24 nucleobases in length. In another aspect, said initial amplification product comprises a tag sequence that is 19 nucleobases in length. In another aspect, said initial amplification product comprises a tag sequence that contains a sequence that is substantially complementary to one of SEQ ID NO:13, SEQ ID NO:16 and SEQ ID NO:33. In another aspect, said initial amplification product comprises a tag sequence that contains a sequence that is substantially identical to one of SEQ ID NO:13, SEQ ID NO:16 and SEQ ID NO:33. In another aspect, said initial amplification product comprises a tag sequence that contains a nucleotide sequence selected from the group consisting of: a sequence with at least 95% identity to SEQ ID NO:43 or complement thereof; a sequence with at least 95% identity to SEQ ID NO:44 or complement thereof; a sequence with 100% identity to SEQ ID NO:43 or complement thereof; and a sequence with 100% identity to SEQ ID NO:44 or complement thereof.

In one embodiment, there is an amplification reaction mixture for generating from an initial nucleic acid amplification product containing a tag sequence or complement thereof, as described above, a further nucleic acid amplification product, wherein said amplification reaction mixture comprises a tag-targeting amplification oligomer comprising a target hybridizing region containing a nucleic acid sequence configured to specifically hybridize to said tag sequence, or complement thereof, that is contained within the nucleotide sequence of said initial nucleic acid amplification product, and wherein said amplification reaction mixture comprises a promoter-based amplification oligomer comprising a target hybridizing region that is 10 to 50 nucleobases in length and contains a nucleotide sequence that is configured to hybridize to all or a portion of a region of a target nucleic acid corresponding to residues 4703 to 4732 of SEQ ID NO:2.

In one aspect, said target hybridizing region of said promoter-based amplification oligomer comprises a sequence that is at least 95% identical to SEQ ID NO:42. In another aspect, said target hybridizing region of said promoter-based amplification oligomer comprises a sequence that is 100% identical to SEQ ID NO:42. In another aspect, said promoter-based amplification oligomer comprising a sequence that is 100% identical to SEQ ID NO:15. In another aspect, said target hybridizing region of said tag-targeting amplification oligomer is 18 to 24 nucleobases in length. In another aspect, said tag-targeting amplification oligomer comprises a sequence that is at least 95% identical to a sequence selected from the group consisting of: SEQ ID NO:13, SEQ ID NO:16 and SEQ ID NO:33. In another aspect, said tag-targeting amplification oligomer comprises a sequence that is 100% identical to a sequence selected from the group consisting of: SEQ ID NO:13, SEQ ID NO:16 and SEQ ID NO:33.

In one aspect, there is provided an initial amplification product that was generated using a tagged amplification oligomer comprising a target hybridizing region and a tag region, wherein said target hybridizing region is from 15 to 50 nucleobases in length and contains a nucleotide sequence that is configured to hybridize to a region of a target nucleic acid corresponding to residues 4752 to 4798 of SEQ ID NO:2, wherein said initial amplification product contains a nucleotide sequence comprising a tag sequence region, and wherein the sequence of said tag region is from 10 to 25 nucleobases in length. In another aspect said initial amplification product comprises a tag sequence that is from 18 to 24 nucleobases in length. In another aspect, said initial amplification product comprises a tag sequence that is 19 nucleobases in length. In another aspect, said initial amplification product comprises a tag sequence that contains a sequence that is substantially complementary to one of SEQ ID NO:13, SEQ ID NO:16 and SEQ ID NO:33. In another aspect, said initial amplification product comprises a tag sequence that contains a sequence that is substantially identical to one of SEQ ID NO:13, SEQ ID NO:16 and SEQ ID NO:33. In another aspect, said initial amplification product comprises a tag sequence that contains a nucleotide sequence selected from the group consisting of: a sequence with at least 95% identity to SEQ ID NO:43 or complement thereof; a sequence with at least 95% identity to SEQ ID NO:44 or complement thereof; a sequence with 100% identity to SEQ ID NO:43 or complement thereof; and a sequence with 100% identity to SEQ ID NO:44 or complement thereof.

In one aspect, there is provided an amplification product generated from said initial amplification product and containing a nucleotide sequence comprising a tag sequence region, wherein the sequence of said tag region is from 10 to 25 nucleobases in length. In another aspect said tag sequence region is from 18 to 24 nucleobases in length. In another aspect, said tag sequence region is 19 nucleobases in length. In another aspect, said tag sequence region contains a sequence that is substantially complementary to one of SEQ ID NO:13, SEQ ID NO:16 and SEQ ID NO:33. In another aspect, said tag sequence region contains a sequence that is substantially identical to one of SEQ ID NO:13, SEQ ID NO:16 and SEQ ID NO:33. In another aspect, said tag sequence region contains a nucleotide sequence selected from the group consisting of: a sequence with at least 95% identity to SEQ ID NO:43 or complement thereof; a sequence with at least 95% identity to SEQ ID NO:44 or complement thereof; a sequence with 100% identity to SEQ ID NO:43 or complement thereof; and a sequence with 100% identity to SEQ ID NO:44 or complement thereof.

In one embodiment, there is provided a method for the in vitro amplification of a nucleic acid from one or more *Mycoplasma* species in a sample, comprising the steps of: (a.) contacting a sample with a tagged amplification oligomer comprising a target hybridizing region and a tag region, wherein said target hybridizing region is from 15 to 50 nucleobases in length and contains a nucleotide sequence that is configured to hybridize to a region of a target nucleic acid corresponding to residues 4752 to 4798 of SEQ ID NO:2; and (b.) providing suitable conditions for performing an amplification reaction.

In one aspect said nucleotide sequence contained within said tagged amplification oligomer target hybridizing region has at least one of a nucleotide addition, a nucleotide deletion, a nucleotide mismatch, a modified nucleotide or a combination thereof relative to a corresponding residue of said target nucleic acid. In another aspect, said target hybridizing region of said tagged amplification oligomer is from 18 to 28 nucleobases in length. In another aspect, said target hybridizing region of said tagged amplification oligomer is 15 to 30 nucleobases in length and contains a nucleotide sequence that is configured to hybridize to a region of a target nucleic acid corresponding to residues 4776 to 4798 of SEQ ID NO:2. In another aspect, said target hybridizing region of said tagged amplification oligomer comprises at least 95% sequence identity to SEQ ID NO:45, SEQ ID NO:46, SEQ ID NO:47 or SEQ ID NO:48.

In one aspect, said tag region of said tagged amplification oligomer is from 10 to 25 nucleobases in length. In another aspect, said tag region is from 18 to 24 nucleobases in length. In another aspect, said tag region is 19 nucleobases in length. In another aspect, said tag region contains a sequence that is substantially complementary to one of SEQ ID NO:13, SEQ ID NO:16 and SEQ ID NO:33. In another aspect, said tag region contains a sequence that is substantially identical to one of SEQ ID NO:13, SEQ ID NO:16 and SEQ ID NO:33. In another aspect, said tag region contains a nucleotide sequence selected from the group consisting of: a sequence with at least 95% identity to SEQ ID NO:43 or complement thereof; a sequence with at least 95% identity to SEQ ID NO:44 or complement thereof; a sequence with 100% identity to SEQ ID NO:43 or complement thereof; and a sequence with 100% identity to SEQ ID NO:44 or complement thereof. In one aspect, said tagged amplification oligomer comprises at least 95% sequence identity to SEQ ID NO:23 or SEQ ID NO:49. In another aspect, said tagged amplification oligomer comprises 100% sequence identity to SEQ ID NO:23.

In one aspect, said tagged amplification oligomer further comprises a tag-closing region, said tag-closing region comprising a nucleotide sequence that is substantially complementary to a portion of said target hybridizing region of said tagged-amplification oligomer to allow for an intramolecular hybridization between the two regions under certain conditions. Preferably, the conditions are those that allow for the tagged oligomer to be in the closed position, while still allowing for steps of the reaction to be performed. In another aspect, said tag-closing region is 3 to 20 nucleobases in length.

In one aspect, said tagged amplification oligomer comprises at least 95% sequence identity to a sequence selected from the group consisting of SEQ ID NO:6 and SEQ ID NO:24. In another aspect, said tagged amplification oligomer comprises 100% sequence identity to SEQ ID NO:6. In another aspect, said tagged amplification oligomer comprises 100% sequence identity to SEQ ID NO:24.

In one aspect, said method further comprises the step of contacting said sample with an additional oligomer. In another aspect, said additional oligomer is a blocker oligomer. In another aspect, said additional oligomer is a blocker oligomer comprising a sequence that is at least 95% identical to SEQ ID NO:9. In another aspect, said additional oligomer is a blocker oligomer comprising a sequence that is at least 95% identical to SEQ ID NO:10. In another aspect, said additional oligomer is a blocker comprising a sequence that is SEQ ID NO:10.

In one aspect, said method comprises contacting said sample with a tagged amplification oligomer with a nucleotide sequence that is at least 95% identical to SEQ ID NO:6, a nucleotide sequence that is at least 95% identical to SEQ ID NO:23, a nucleotide sequence that is at least 95% identical to SEQ ID NO:24, a nucleotide sequence that is 100% identical to SEQ ID NO:6, a nucleotide sequence that is 100% identical to SEQ ID NO:23, or a nucleotide sequence that is 100% identical to SEQ ID NO:24; and wherein said contacting step further comprises contacting said sample with a blocker oligomer. In another aspect, said blocker oligomer comprises a sequence that is at least 95% identical to SEQ ID NO:9. In another aspect, said blocker oligomer comprises a sequence that is at least 95% identical to SEQ ID NO:10. In another aspect, said blocker comprises a sequence that is SEQ ID NO:9.

In one aspect, said method at step (b.) results in an initial amplification product containing a tag sequence, or complement thereof. In another aspect, there is provided an initial amplification product with a nucleotide sequence comprising a tag sequence region, wherein said tag sequence is from 10 to 25 nucleobases in length. In another aspect said initial amplification product comprises a tag sequence that is from 18 to 24 nucleobases in length. In another aspect, said initial amplification product comprises a tag sequence that is 19 nucleobases in length. In another aspect, said initial amplification product comprises a tag sequence that contains a sequence that is substantially complementary to one of SEQ ID NO:13, SEQ ID NO:16 and SEQ ID NO:33. In another aspect, said initial amplification product comprises a tag sequence that contains a sequence that is substantially identical to one of SEQ ID NO:13, SEQ ID NO:16 and SEQ ID NO:33. In another aspect, said initial amplification product comprises a tag sequence that contains a nucleotide sequence selected from the group consisting of: a sequence with at least 95% identity to SEQ ID NO:43 or complement thereof; a sequence with at least 95% identity to SEQ ID NO:44 or complement thereof; a sequence with 100% identity to SEQ ID NO:43 or complement thereof; and a sequence with 100% identity to SEQ ID NO:44 or complement thereof. In one aspect, said initial amplification product has a 3' end defined by a blocker oligomer. In another aspect, said initial amplification product has a 3' end that is not defined by a blocker oligomer.

In one embodiment of the current invention, there is provided a method for the in vitro amplification of an initial amplification product, comprising the steps of (c.) contacting the sample with at least one additional amplification oligomer selected from the group consisting of a tag-targeting amplification oligomer, a primer oligomer and a promoter-based amplification oligomer; and (d.) providing suitable conditions for performing a second amplification reaction. In one aspect, the oligomers of step (c.) and the oligomers of step (a.) are contacted to said sample at the same time point. In one aspect, the oligomers of step (c.) and the oligomers of step (a.) are contacted to the sample and a single amplification reaction is performed. In this aspect, steps (b.) and (d.) are combined to provide suitable conditions for performing an amplification reaction to generate an initial amplification product and for performing an amplification reaction generate a second amplification product therefrom. Though all of the amplification oligomers are present in this combined amplification reaction aspect, the tag-targeting amplification oligomers are configured to not participate in amplification until a tagged amplification oligomer is incorporated into an initial amplification product. In another aspect, the oligomers of step (c.) and the oligomers of step (a.) are contacted to said sample at separate time points. In one aspect, the method comprises the step of (c.) providing to an amplification product generated in step (b.) a second reaction mixture comprising a tag-targeting amplification oligomer consisting essentially of a target hybridizing region that contains a nucleotide sequence configured to specifically hybridize to a tag region of said tagged amplification oligomer, and comprising a second amplification oligomer; and (d.) providing suitable conditions for performing a second amplification reaction.

In one aspect for generating an amplification product, said sample is contacted with a first additional amplification oligomer that is a tag-targeting amplification oligomer comprising a target hybridizing region that contains a nucleotide sequence configured to specifically hybridize to a tag region of said, or complement thereof in an initial amplification oligomer, and is contacted with a second additional amplification oligomer. In another aspect, said tag-targeting amplification oligomer comprises a target hybridization region that is 18 to 24 nucleobases in length. In another aspect, said tag-targeting amplification oligomer comprises a sequence that is at least 95% identical to a sequence selected from the group consisting of SEQ ID NO:13, SEQ ID NO:16 and SEQ ID NO:33. In another aspect, said tag-targeting amplification oligomer comprises a sequence that is 100% identical to SEQ ID NO:13. In another aspect, said tag-targeting amplification oligomer comprises a sequence that is 100% identical to SEQ ID NO:16. In another aspect, said tag-targeting amplification oligomer comprises a sequence that is 100% identical to SEQ ID NO:33. In one aspect, said second amplification oligomer is a primer amplification oligomer, a promoter based amplification oligomer or a tagged amplification oligomer. In another aspect, said second amplification oligomer is a promoter-based amplification oligomer comprising a target hybridizing region that is 10 to 50 nucleobases in length and contains a nucleotide sequence that is configured to hybridize to all or a portion of a region of a target nucleic acid corresponding to residues 4703 to 4732 of SEQ ID NO:2. In another aspect, said second additional amplification oligomer is a promoter-based amplification oligomer comprising a target hybridizing region that comprises a sequence that is at least 95% identical to SEQ ID NO:42. In another aspect, said second additional amplification oligomer is a promoter-based amplification oligomer that comprises a sequence that is 100% identical to SEQ ID NO:42. In another aspect, said second additional amplification oligomer is a promoter-based amplification oligomer that comprises a sequence that is 100% identical to SEQ ID NO:15.

In one aspect for the in vitro amplification of a nucleic acid from one or more *Mycoplasma* species in a sample, there is provided at least one tagged amplification oligomer that is at least 95% identical to SEQ ID NO:6; at least one blocker oligomer that is at least 95% identical to SEQ ID NO:9; at least one tag-targeting amplification oligomer that is at least 95% identical to SEQ ID NO:13 and at least one promoter-based amplification oligomer that is at least 95% identical to SEQ ID NO:15. In another aspect, said at least one tagged amplification oligomer is 100% identical to SEQ ID NO:6. In another aspect, said at least one blocker oligomer is 100% identical to SEQ ID NO:9. In another aspect, said at least one tag-targeting amplification oligomer is 100% identical to SEQ ID NO:13. In another aspect, said at least one promoter-based amplification oligomer is 95% identical to SEQ ID NO:15. In another aspect there are provided one or more additional tagged amplification oligomers each or which could be selected from the group consisting of: a tagged amplification oligomer with at least 95% identity to SEQ ID NO:5; a tagged amplification oligomer with at least 95% identity to SEQ ID NO:7, a tagged amplification oligomer with at least 95% identity to SEQ ID NO:8, a tagged amplification oligomer with 100% identity to SEQ ID NO:5, a tagged amplification oligomer with 100% identity to SEQ ID NO:7 and a tagged amplification oligomer with 100% identity to SEQ ID NO:8.

In one embodiment there is further provided an analysis step, wherein an initial amplification product, an amplification product or both are analyzed. In one aspect, said analysis comprises a detection step to identify the presence or absence of an initial amplification product from an amplification reaction in step (b.), an amplification product generated in step (d.) or both initial amplification and amplification products generated in steps (b.) and (d.). In another aspect, said detection step is a probe-based detection step. In another aspect, said probe-based detection step uses a probe with a nucleotide sequence that is at least 95% identical to SEQ ID NO:14. In another aspect, said detection step is a probe-based detection step. In another aspect, said probe-based detection step uses a probe with a nucleotide sequence that is 100% identical to SEQ ID NO:14.

In one embodiment of the invention, there is provided a composition for determining the presence or absence of one or more *Acholeplasma* species in a sample, said composition comprising a tagged amplification oligomer comprising a target hybridizing region and a tag region, wherein said target hybridizing region is from 15 to 50 nucleobases in length and contains a nucleotide sequence that is configured to hybridize to a region of a target nucleic acid corresponding to residues1954 to 2006 SEQ ID NO:3.

In one aspect, said target-hybridizing region of said tagged amplification oligomer may contain one or more of a nucleotide addition, a nucleotide deletion, a nucleotide mismatch, a modified nucleotide or a combination thereof relative to a corresponding residue of said target nucleic acid. In another aspect, said target hybridizing region is from 18 to 28 nucleobases in length. In another aspect, said target hybridizing region comprises at least 95% sequence identity to SEQ ID NO:50. In another aspect, said target hybridizing region comprises at least 95% sequence identity to SEQ ID NO:51. In another aspect, said target hybridizing region comprises at least 95% sequence identity to SEQ ID NO:52. In another aspect, said target hybridizing region comprises at least 95% sequence identity to SEQ ID NO:53. In another aspect, said target hybridizing region comprises at least 95% sequence identity to SEQ ID NO:54. In another aspect, said target hybridizing region comprises at least 95% sequence identity to SEQ ID NO:55. In another aspect, said target hybridizing region is 15 to 30 nucleobases in length and contains a nucleotide sequence that is configured to hybridize to a region of a target nucleic acid corresponding to residues 1973 to 2006 of SEQ ID NO:3.

In one aspect, said tag region of said tagged amplification oligomer is from 10 to 25 nucleobases in length. In another aspect, said tag region is from 18 to 24 nucleobases in length. In another aspect, said tag region is 19 nucleobases in length. In another aspect, said tag region contains a sequence that is substantially complementary to one of SEQ ID NO:13, SEQ ID NO:16 and SEQ ID NO:33. In another aspect, said tag region contains a sequence that is substantially identical to one of SEQ ID NO:13, SEQ ID NO:16 and SEQ ID NO:33. In another aspect, said tag region contains a nucleotide sequence selected from the group consisting of: a sequence with at least 95% identity to SEQ ID NO:43 or complement thereof; a sequence with at least 95% identity to SEQ ID NO:44 or complement thereof; a sequence with 100% identity to SEQ ID NO:43 or complement thereof; and a sequence with 100% identity to SEQ ID NO:44 or complement thereof. In one aspect, said tagged amplification oligomer further comprises a tag-closing region, said tag-closing region comprising a nucleotide sequence that is substantially complementary to a portion of said target hybridizing region of said tagged-amplification oligomer. In another aspect, said tag-closing region is 3 to 20 nucleobases in length.

In one aspect, said tagged amplification oligomer comprises at least 95% sequence identity to SEQ ID NO:7, SEQ ID NO:31, SEQ ID NO:56 or SEQ ID NO:57. In another aspect, said tagged amplification oligomer comprises 100% sequence identity to SEQ ID NO:7. In another aspect, said tagged amplification oligomer comprises 100% sequence identity to SEQ ID NO:31.

In one embodiment, said composition further comprises an additional oligomer comprising a target hybridizing region containing a nucleotide sequence that is configured to hybridize to a region of a target nucleic acid corresponding to residues 1842 to 1884 of SEQ ID NO:3, wherein said additional oligomer is selected from the group consisting of a blocker oligomer, a primer oligomer and a promoter-based amplification oligomer. In one aspect, said additional oligomer is a blocker oligomer. In another aspect, said additional oligomer is a blocker oligomer comprising a sequence that is at least 95% identical to SEQ ID NO:9. In another aspect, said additional oligomer is a blocker oligomer comprising a sequence that is at least 95% identical to SEQ ID NO:10. In another aspect, said additional oligomer is a blocker comprising a sequence that is SEQ ID NO:10. In one aspect, said additional oligomer is a promoter-based amplification oligomer. In another aspect, said additional oligomer is a promoter-based amplification oligomer comprising a target hybridizing region that is 10 to 50 nucleobases in length and contains a nucleotide sequence that is configured to hybridize to all or a portion of a region of a target nucleic acid corresponding to residues 1855 to 1884 SEQ ID NO:3. In another aspect, said additional oligomer is a promoter-based amplification oligomer comprising a target hybridizing region comprising a sequence that is at least 95% identical to SEQ ID NO:42. In another aspect, said additional oligomer is a promoter-based amplification oligomer comprising a target hybridizing region comprising a sequence that is 100% identical to SEQ ID NO:42. In another aspect, said additional oligomer is a promoter-based amplification comprising a sequence that is at least 95% identical to SEQ ID NO:15. In another aspect, said additional oligomer is a promoter-based amplification oligomer comprising a sequence that is 100% identical to SEQ ID NO:15.

In one embodiment, said composition further comprises a tag-targeting amplification oligomer comprising a target hybridizing region that contains a nucleotide sequence configured to specifically hybridize to a tag region of said tagged amplification oligomer or complement thereof. In one aspect, said tag-targeting amplification oligomer comprises a target hybridization region that is 18 to 24 nucleobases in length. In another aspect, said tag-targeting amplification oligomer comprises a sequence that is at least 95% identical to a sequence selected from the group consisting of SEQ ID NO:13, SEQ ID NO:16 and SEQ ID NO:33. In another aspect, said tag-targeting amplification oligomer comprises a sequence that is 100% identical to SEQ ID NO:13. In another aspect, said tag-targeting amplification oligomer comprises a sequence that is 100% identical to SEQ ID NO:16. In another aspect, said tag-targeting amplification oligomer comprises a sequence that is 100% identical to SEQ ID NO:33.

In one embodiment, said composition further comprises a first tagged amplification oligomer comprising a target hybridizing region and a tag region, wherein said target hybridizing region is from 15 to 50 nucleobases in length and contains a nucleotide sequence that is configured to hybridize to a region of a target nucleic acid corresponding to residues 1954 to 2006 of SEQ ID NO:3, as is described above, and one or more additional tagged amplification oligomers. In one aspect, said one or more additional tagged amplification oligomers includes a tagged amplification oligomer comprising a nucleic acid sequence that is at least 95% identical to SEQ ID NO:5. In another aspect, said one or more additional tagged amplification oligomers includes a tagged amplification oligomer comprising a nucleic acid sequence that is at least 95% identical to SEQ ID NO:6. In another aspect, said one or more additional tagged amplification oligomers includes a tagged amplification oligomer comprising a nucleic acid sequence that is at least 95% identical to SEQ ID NO:8. In another aspect, said one or more additional tagged amplification oligomers includes a tagged amplification oligomer comprising a nucleic acid sequence that is 100% identical to SEQ ID NO:5. In another aspect, said one or more additional tagged amplification oligomers includes a tagged amplification oligomer comprising a nucleic acid sequence that is 100% identical to SEQ ID NO:6. In another aspect, said one or more additional tagged amplification oligomers includes a tagged amplification oligomer comprising a nucleic acid sequence that is 100% identical to SEQ ID NO:8. In another aspect, said one or more additional tagged amplification oligomers includes a first additional tagged amplification oligomer that is at least 95% identical to SEQ ID NO:5 and a second additional tagged amplification oligomer that is at least 95% identical to SEQ ID NO:6. In another aspect, said one or more additional tagged amplification oligomers includes a first additional tagged amplification oligomer that is at least 95% identical to SEQ ID NO:5 and a second additional tagged amplification oligomer that is at least 95% identical to SEQ ID NO:8. In another aspect, said one or more additional tagged amplification oligomers includes a first additional tagged amplification oligomer that is at least 95% identical to SEQ ID NO:6 and a second additional tagged amplification oligomer that is at least 95% identical to SEQ ID NO:8. In another aspect, said one or more additional tagged amplification oligomers includes a first additional tagged amplification oligomer that is at least 95% identical to SEQ ID NO:5, a second additional tagged amplification oligomer that is at least 95% identical to SEQ ID NO:6 and a third additional tagged amplification oligomer that is at least 95% identical to SEQ ID NO:8.

In one embodiment, said composition comprises at least two oligomers, one of which is a tagged amplification oligomer and the other of which is a blocker oligomer. In one aspect, said tagged amplification oligomer comprises a nucleotide sequence that is at least 95% identical to SEQ ID NO:7. In another aspect, said blocker oligomer comprises a nucleotide sequence that is at least 95% identical to SEQ ID NO:9. In another aspect, said blocker oligomer comprises a nucleotide sequence that is at least 95% identical to SEQ ID NO:10. In one aspect, said tagged amplification oligomer comprises a nucleotide sequence that is 100% identical to SEQ ID NO:7. In another aspect, said blocker oligomer comprises a nucleotide sequence that is 100% identical to SEQ ID NO:9. In another aspect, said blocker oligomer comprises a nucleotide sequence that is 100% identical to SEQ ID NO:10. In another aspect, said tagged amplification oligomer comprises a nucleotide sequence that is 100% identical to SEQ ID NO:7 and said blocker oligomer comprises a nucleotide sequence that is 100% identical to SEQ ID NO:9. In another aspect, said tagged amplification oligomer comprises a nucleotide sequence that is 100% identical to SEQ ID NO:7 and said blocker oligomer comprises a nucleotide sequence that is 100% identical to SEQ ID NO:10.

In one embodiment, said composition further comprises at least two additional oligomers, one of which is a tag-targeting oligomer, the other of which is a promoter based amplification oligomer. In one aspect, said tag-targeting amplification oligomer comprises a nucleotide sequence that is at least 95% identical to SEQ ID NO:13. In another aspect, said promoter-based amplification oligomer comprises a nucleotide sequence that is at least 95% identical to SEQ ID NO:15. In one aspect, said tag-targeting amplification oligomer comprises a nucleotide sequence that is 100% identical to SEQ ID NO:13. In another aspect, said promoter-based amplification oligomer comprises a nucleotide sequence that is 100% identical to SEQ ID NO:15. In another aspect, said tag-targeting amplification oligomer comprises a nucleotide sequence that is 100% identical to SEQ ID NO:13 and said promoter-based amplification oligomer comprises a nucleotide sequence that is 100% identical to SEQ ID NO:15.

In one embodiment, said composition comprises at least two oligomers, one of which is a tagged amplification oligomer comprising a target hybridizing region and a tag region, wherein said target hybridizing region is from 15 to 50 nucleobases in length and contains a nucleotide sequence that is configured to hybridize to a region of a target nucleic acid corresponding to residues 1954 to 2006 of SEQ ID NO:3, as is described above; and the others of which can be selected from the group consisting of: an additional tagged amplification oligomer; a blocker oligomer; a tag-targeting oligomer; and a promoter based amplification oligomer. In one aspect, said tagged amplification oligomer comprises a nucleotide sequence that is at least 95% identical to SEQ ID NO:7. In another aspect, said blocker oligomer comprises a nucleotide sequence that is at least 95% identical to SEQ ID NO:9. In another aspect, said blocker oligomer comprises a nucleotide sequence that is at least 95% identical to SEQ ID NO:10. In another aspect, said tag-targeting amplification oligomer comprises a nucleotide sequence that is at least 95% identical to SEQ ID NO:13. In another aspect, said promoter-based amplification oligomer comprises a nucleotide sequence that is at least 95% identical to SEQ ID NO:15. In another aspect, said additional tagged amplification oligomer comprises a nucleic acid sequence that is at least 95% identical to SEQ ID NO:5. In another aspect, said additional tagged amplification oligomer comprises a nucleic acid sequence that is at least 95% identical to SEQ ID NO:6. In another aspect, said additional tagged amplification oligomer comprises a nucleic acid sequence that is at least 95% identical to SEQ ID NO:8. In one aspect, said tagged amplification oligomer comprises a nucleotide sequence that is 100% identical to SEQ ID NO:7. In another aspect, said blocker oligomer comprises a nucleotide sequence that is 100% identical to SEQ ID NO:9. In another aspect, said blocker oligomer comprises a nucleotide sequence that is 100% identical to SEQ ID NO:10. In one aspect, said tag-targeting amplification oligomer comprises a nucleotide sequence that is 100% identical to SEQ ID NO:13. In another aspect, said promoter-based amplification oligomer comprises a nucleotide sequence that is 100% identical to SEQ ID NO:15. In another aspect, said tagged amplification oligomer comprises a nucleotide sequence that is 100% identical to SEQ ID NO:7, said blocker oligomer comprises a nucleotide sequence that is 100% identical to SEQ ID NO:9, said tag-targeting amplification oligomer comprises a nucleotide sequence that is 100% identical to SEQ ID NO:13, and said promoter-based amplification oligomer comprises a nucleotide sequence that is 100% identical to SEQ ID NO:15. In another aspect, said tagged amplification oligomer comprises a nucleotide sequence that is 100% identical to SEQ ID NO:7, said blocker oligomer comprises a nucleotide sequence that is 100% identical to SEQ ID NO:10, said tag-targeting amplification oligomer comprises a nucleotide sequence that is 100% identical to SEQ ID NO:13, and said promoter-based amplification oligomer comprises a nucleotide sequence that is 100% identical to SEQ ID NO:15. In another aspect, said additional tagged amplification oligomer comprises a nucleic acid sequence that is 100% identical to SEQ ID NO:5. In another aspect, said additional tagged amplification oligomer comprises a nucleic acid sequence that is 100% identical to SEQ ID NO:6. In another aspect, said additional tagged amplification oligomer comprises a nucleic acid sequence that is 100% identical to SEQ ID NO:8.

In one embodiment, there is a reaction mixture for generating from one or more *Acholeplasma* species in a sample an initial nucleic acid amplification product containing a tag sequence or complement thereof, wherein said reaction mixture comprises a tagged amplification oligomer comprising a target hybridizing region and a tag region, wherein said target hybridizing region is from 15 to 50 nucleobases in length and contains a nucleotide sequence that is configured to hybridize to a region of a target nucleic acid corresponding to residues 1954 to 2006 of SEQ ID NO:3, as is described above. In one aspect, said initial amplification product comprises a tag sequence that is from 10 to 25 nucleobases in length. In another aspect said initial amplification product comprises a tag sequence that is from 18 to 24 nucleobases in length. In another aspect, said initial amplification product comprises a tag sequence that is 19 nucleobases in length. In another aspect, said initial amplification product comprises a tag sequence that contains a sequence that is substantially complementary to one of SEQ ID NO:13, SEQ ID NO:16 and SEQ ID NO:33. In another aspect, said initial amplification product comprises a tag sequence that contains a sequence that is substantially identical to one of SEQ ID NO:13, SEQ ID NO:16 and SEQ ID NO:33. In another aspect, said initial amplification product comprises a tag sequence that contains a nucleotide sequence selected from the group consisting of: a sequence with at least 95% identity to SEQ ID NO:43 or complement thereof; a sequence with at least 95% identity to SEQ ID NO:44 or complement thereof; a sequence with 100% identity to SEQ ID NO:43 or complement thereof; and a sequence with 100% identity to SEQ ID NO:44 or complement thereof.

In one embodiment, there is an amplification reaction mixture for generating from an initial nucleic acid amplification product containing a tag sequence or complement thereof, as described above, a further nucleic acid amplification product, wherein said amplification reaction mixture comprises a tag-targeting amplification oligomer comprising a target hybridizing region containing a nucleic acid sequence configured to specifically hybridize to said tag sequence, or complement thereof, that contained within the nucleotide sequence of said initial nucleic acid amplification product, and wherein said amplification reaction mixture comprises a promoter-based amplification oligomer comprising a target hybridizing region that is 10 to 50 nucleobases in length and contains a nucleotide sequence that is configured to hybridize to all or a portion of a region of a target nucleic acid corresponding to residues 1855 to 1884 of SEQ ID NO:3. In one aspect, said target hybridizing region of said promoter-based amplification oligomer comprises a sequence that is at least 95% identical to SEQ ID NO:42. In another aspect, said target hybridizing region of said promoter-based amplification oligomer comprises a sequence that is 100% identical to SEQ ID NO:42. In another aspect, said promoter-based amplification oligomer comprising a sequence that is 100% identical to SEQ ID NO:15. In another aspect, said target hybridizing region of said tag-targeting amplification oligomer is 18 to 24 nucleobases in length. In another aspect, said tag-targeting amplification oligomer comprises a sequence that is at least 95% identical to a sequence selected from the group consisting of: SEQ ID NO:13, SEQ ID NO:16 and SEQ ID NO:33. In another aspect, said tag-targeting amplification oligomer comprises a sequence that is 100% identical to a sequence selected from the group consisting of: SEQ ID NO:13, SEQ ID NO:16 and SEQ ID NO:33.

In one aspect, there is provided an initial amplification product that was generated using a tagged amplification oligomer comprising a target hybridizing region and a tag region, wherein said target hybridizing region is from 15 to 50 nucleobases in length and contains a nucleotide sequence that is configured to hybridize to a region of a target nucleic acid corresponding to residues 1954 to 2006 of SEQ ID NO:3, wherein said initial amplification product contains a nucleotide sequence comprising a tag sequence region, and wherein the sequence of said tag region is from 10 to 25 nucleobases in length. In another aspect said initial amplification product comprises a tag sequence that is from 18 to 24 nucleobases in length. In another aspect, said initial amplification product comprises a tag sequence that is 19 nucleobases in length. In another aspect, said initial amplification product comprises a tag sequence that contains a sequence that is substantially complementary to one of SEQ ID NO:13, SEQ ID NO:16 and SEQ ID NO:33. In another aspect, said initial amplification product comprises a tag sequence that contains a sequence that is substantially identical to one of SEQ ID NO:13, SEQ ID NO:16 and SEQ ID NO:33. In another aspect, said initial amplification product comprises a tag sequence that contains a nucleotide sequence selected from the group consisting of: a sequence with at least 95% identity to SEQ ID NO:43 or complement thereof; a sequence with at least 95% identity to SEQ ID NO:44 or complement thereof; a sequence with 100% identity to SEQ ID NO:43 or complement thereof; and a sequence with 100% identity to SEQ ID NO:44 or complement thereof. In one aspect, there is provided an amplification product generated from said initial amplification product and containing a nucleotide sequence comprising a tag sequence region, wherein the sequence of said tag region is from 10 to 25 nucleobases in length. In another aspect said tag sequence region is from 18 to 24 nucleobases in length. In another aspect, said tag sequence region is 19 nucleobases in length. In another aspect, said tag sequence region contains a sequence that is substantially complementary to one of SEQ ID NO:13, SEQ ID NO:16 and SEQ ID NO:33. In another aspect, said tag sequence region contains a sequence that is substantially identical to one of SEQ ID NO:13, SEQ ID NO:16 and SEQ ID NO:33. In another aspect, said tag sequence region contains a nucleotide sequence selected from the group consisting of: a sequence with at least 95% identity to SEQ ID NO:43 or complement thereof; a sequence with at least 95% identity to SEQ ID NO:44 or complement thereof; a sequence with 100% identity to SEQ ID NO:43 or complement thereof; and a sequence with 100% identity to SEQ ID NO:44 or complement thereof.

In one embodiment, there is provided a method for the in vitro amplification of a nucleic acid from one or more *Acholeplasma* species in a sample, comprising the steps of: (a.) contacting a sample with a tagged amplification oligomer comprising a target hybridizing region that is from 15 to 50 nucleobases in length and contains a nucleotide sequence that is configured to hybridize to a region of a target nucleic acid corresponding to residues 1954 to 2006 of SEQ ID NO:3; and (b.) providing suitable conditions for performing an amplification reaction.

In one aspect said nucleotide sequence contained within said tagged amplification oligomer target hybridizing region has at least one of a nucleotide addition, a nucleotide deletion, a nucleotide mismatch, a modified nucleotide or a combination thereof relative to a corresponding residue of said target nucleic acid. In another aspect, said target hybridizing region of said tagged amplification oligomer is from 18 to 28 nucleobases in length. In another aspect, said target hybridizing region of said tagged amplification oligomer is 15 to 30 nucleobases in length and contains a nucleotide sequence that is configured to hybridize to a region of a target nucleic acid corresponding to residues 1973 to 2006 of SEQ ID NO:3. In another aspect, said target hybridizing region of said tagged amplification oligomer comprises at least 95% sequence identity to SEQ ID NO:50, SEQ ID NO:51, SEQ ID NO:52, SEQ ID NO:53, SEQ ID NO:54 or SEQ ID NO:55. In one aspect, said tag region of said tagged amplification oligomer is from 10 to 25 nucleobases in length. In another aspect, said tag region is from 18 to 24 nucleobases in length. In another aspect, said tag region is 19 nucleobases in length. In another aspect, said tag region contains a sequence that is substantially complementary to one of SEQ ID NO:13, SEQ ID NO:16 and SEQ ID NO:33. In another aspect, said tag region contains a sequence that is substantially identical to one of SEQ ID NO:13, SEQ ID NO:16 and SEQ ID NO:33. In another aspect, said tag region contains a nucleotide sequence selected from the group consisting of: a sequence with at least 95% identity to SEQ ID NO:43 or complement thereof; a sequence with at least 95% identity to SEQ ID NO:44 or complement thereof; a sequence with 100% identity to SEQ ID NO:43 or complement thereof; and a sequence with 100% identity to SEQ ID NO:44 or complement thereof. In one aspect, said tagged amplification oligomer further comprises a tag-closing region, said tag-closing region comprising a nucleotide sequence that is substantially complementary to a portion of said target hybridizing region of said tagged-amplification oligomer. In another aspect, said tag-closing region is 3 to 20 nucleobases in length. In one aspect, said tagged amplification oligomer comprises at least 95% sequence identity to SEQ ID NO:7, SEQ ID NO:31, SEQ ID NO:56 or SEQ ID NO:57. In another aspect, said tagged amplification oligomer comprises 100% sequence identity to SEQ ID NO:7. In another aspect, said tagged amplification oligomer comprises 100% sequence identity to SEQ ID NO:31.

In one aspect, said method further comprises the step of contacting said sample with an additional oligomer. In another aspect, said additional oligomer is a blocker oligomer. In another aspect, said additional oligomer is a blocker oligomer comprising a sequence that is at least 95% identical to SEQ ID NO:9. In another aspect, said additional oligomer is a blocker oligomer comprising a sequence that is at least 95% identical to SEQ ID NO:10. In another aspect, said additional oligomer is a blocker comprising a sequence that is SEQ ID NO:10. In one aspect, said method comprises contacting said sample with a tagged amplification oligomer with a nucleotide sequence that is at least 95% identical to SEQ ID NO:7, a nucleotide sequence that is at least 95% identical to SEQ ID NO:31, a nucleotide sequence that is 100% identical to SEQ ID NO:7, or a nucleotide sequence that is 100% identical to SEQ ID NO:31; and wherein said contacting step further comprises contacting said sample with a blocker oligomer. In another aspect, said blocker oligomer comprises a sequence that is at least 95% identical to SEQ ID NO:9. In another aspect, said blocker oligomer comprises a sequence that is at least 95% identical to SEQ ID NO:10. In another aspect, said blocker comprises a sequence that is SEQ ID NO:10.

In one aspect, said method at step (b.) results in an initial amplification product containing a tag sequence, or complement thereof. In another aspect, there is provided an initial amplification product with a nucleotide sequence comprising a tag sequence region, wherein said tag sequence is from 10 to 25 nucleobases in length. In another aspect said initial amplification product comprises a tag sequence that is from 18 to 24 nucleobases in length. In another aspect, said initial amplification product comprises a tag sequence that is 19 nucleobases in length. In another aspect, said initial amplification product comprises a tag sequence that contains a sequence that is substantially complementary to one of SEQ ID NO:13, SEQ ID NO:16 and SEQ ID NO:33. In another aspect, said initial amplification product comprises a tag sequence that contains a sequence that is substantially identical to one of SEQ ID NO:13, SEQ ID NO:16 and SEQ ID NO:33. In another aspect, said initial amplification product comprises a tag sequence that contains a nucleotide sequence selected from the group consisting of: a sequence with at least 95% identity to SEQ ID NO:43 or complement thereof; a sequence with at least 95% identity to SEQ ID NO:44 or complement thereof; a sequence with 100% identity to SEQ ID NO:43 or complement thereof; and a sequence with 100% identity to SEQ ID NO:44 or complement thereof. In one aspect, said initial amplification product has a 3' end defined by a blocker oligomer. In another aspect, said initial amplification product has a 3' end that is not defined by a blocker oligomer.

In one embodiment of the current invention, there is provided a method for the in vitro amplification of an initial amplification product, comprising the steps of (c.) contacting the sample with at least one additional amplification oligomer selected from the group consisting of a tag-targeting amplification oligomer, a primer oligomer and a promoter-based amplification oligomer; and (d.) providing suitable conditions for performing a second amplification reaction. In one aspect, the oligomers of step (c.) and the oligomers of step (a.) are contacted to said sample at the same time point. In one aspect, the oligomers of step (c.) and the oligomers of step (a.) are contacted to the sample and a single amplification reaction is performed. In this aspect, steps (b.) and (d.) are combined to provide suitable conditions for performing an amplification reaction to generate an initial amplification product and for performing an amplification reaction generate a second amplification product therefrom. Though all of the amplification oligomers are present in this combined amplification reaction aspect, the tag-targeting amplification oligomers are configured to not participate in amplification until a tagged amplification oligomer is incorporated into an initial amplification product. In another aspect, the oligomers of step (c.) and the oligomers of step (a.) are contacted to said sample at separate time points. In one aspect, the method comprises the step of (c.) providing to an amplification product generated in step (b.) a second reaction mixture comprising a tag-targeting amplification oligomer consisting essentially of a target hybridizing region that contains a nucleotide sequence configured to specifically hybridize to a tag region of said tagged amplification oligomer, and comprising a second amplification oligomer; and (d.) providing suitable conditions for performing a second amplification reaction.

In one aspect for generating an amplification product, said sample is contacted with a first additional amplification oligomer that is a tag-targeting amplification oligomer comprising a target hybridizing region that contains a nucleotide sequence configured to specifically hybridize to a tag region of said, or complement thereof in an initial amplification oligomer, and is contacted with a second additional amplification oligomer. In another aspect, said tag-targeting amplification oligomer comprises a target hybridization region that is 18 to 24 nucleobases in length. In another aspect, said tag-targeting amplification oligomer comprises a sequence that is at least 95% identical to a sequence selected from the group consisting of SEQ ID NO:13, SEQ ID NO:16 and SEQ ID NO:33. In another aspect, said tag-targeting amplification oligomer comprises a sequence that is 100% identical to SEQ ID NO:13. In another aspect, said tag-targeting amplification oligomer comprises a sequence that is 100% identical to SEQ ID NO:16. In another aspect, said tag-targeting amplification oligomer comprises a sequence that is 100% identical to SEQ ID NO:33. In one aspect, said second amplification oligomer is a primer amplification oligomer, a promoter based amplification oligomer or a tagged amplification oligomer. In another aspect, said second amplification oligomer is a promoter-based amplification oligomer comprising a target hybridizing region that is 10 to 50 nucleobases in length and contains a nucleotide sequence that is configured to hybridize to all or a portion of a region of a target nucleic acid corresponding to residues 1855 to 1884 of SEQ ID NO:3. In another aspect, said second additional amplification oligomer is a promoter-based amplification oligomer comprising a target hybridizing region that comprises a sequence that is at least 95% identical to SEQ ID NO:42. In another aspect, said second additional amplification oligomer is a promoter-based amplification oligomer that comprises a sequence that is 100% identical to SEQ ID NO:42. In another aspect, said second additional amplification oligomer is a promoter-based amplification oligomer that comprises a sequence that is 100% identical to SEQ ID NO:15.

In one aspect for the in vitro amplification of a nucleic acid from one or more *Acholeplasma* species in a sample, there is provided at least one tagged amplification oligomer that is at least 95% identical to SEQ ID NO:7; at least one blocker oligomer that is at least 95% identical to SEQ ID NO:10; at least one tag-targeting amplification oligomer that is at least 95% identical to SEQ ID NO:13 and at least one promoter-based amplification oligomer that is at least 95% identical to SEQ ID NO:15. In another aspect, said at least one tagged amplification oligomer is 100% identical to SEQ ID NO:7. In another aspect, said at least one blocker oligomer is 100% identical to SEQ ID NO:10. In another aspect, said at least one tag-targeting amplification oligomer is 100% identical to SEQ ID NO:13. In another aspect, said at least one promoter-based amplification oligomer is 95% identical to SEQ ID NO:15. In another aspect there are provided one or more additional tagged amplification oligomers each or which could be selected from the group consisting of: a tagged amplification oligomer with at least 95% identity to SEQ ID NO:5; a tagged amplification oligomer with at least 95% identity to SEQ ID NO:6, a tagged amplification oligomer with at least 95% identity to SEQ ID NO:8, a tagged amplification oligomer with 100% identity to SEQ ID NO:5, a tagged amplification oligomer with 100% identity to SEQ ID NO:6 and a tagged amplification oligomer with 100% identity to SEQ ID NO:8.

In one embodiment there is further provided an analysis step, wherein an initial amplification product, an amplification product or both are analyzed. In one aspect, said analysis comprises a detection step to identify the presence or absence of an initial amplification product from an amplification reaction in step (b.), an amplification product generated in step (d.) or both initial amplification and amplification products generated in steps (b.) and (d.). In another aspect, said detection step is a probe-based detection step. In another aspect, said probe-based detection step uses a probe with a nucleotide sequence that is at least 95% identical to SEQ ID NO:14. In another aspect, said detection step is a probe-based detection step. In another aspect, said probe-based detection step uses a probe with a nucleotide sequence that is 100% identical to SEQ ID NO:14.

In one embodiment of the invention, there is provided a composition for determining the presence or absence of one or more *Spiroplasma* species in a sample, said composition comprising a tagged amplification oligomer comprising a target hybridizing region and a tag region, wherein said target hybridizing region is from 15 to 50 nucleobases in length and contains a nucleotide sequence that is configured to hybridize to a region of a target nucleic acid corresponding to residues 1994 to 2036 of SEQ ID NO:4.

In one aspect, said target-hybridizing region of said tagged amplification oligomer may contain one or more of a nucleotide addition, a nucleotide deletion, a nucleotide mismatch, a modified nucleotide or a combination thereof relative to a corresponding residue of said target nucleic acid. In another aspect, said target hybridizing region is from 18 to 28 nucleobases in length. In another aspect, said target hybridizing region comprises at least 95% sequence identity to SEQ ID NO:58, SEQ ID NO:59, SEQ ID NO:60, SEQ ID NO:61 or SEQ ID NO:62. In another aspect, said target hybridizing region is 15 to 30 nucleobases in length and contains a nucleotide sequence that is configured to hybridize to a region of a target nucleic acid corresponding to residues 1994 to 2017 of SEQ ID NO:4. In one aspect, said tag region of said tagged amplification oligomer is from 10 to 25 nucleobases in length. In another aspect, said tag region is from 18 to 24 nucleobases in length. In another aspect, said tag region is 19 nucleobases in length. In another aspect, said tag region contains a sequence that is substantially complementary to one of SEQ ID NO:13, SEQ ID NO:16 and SEQ ID NO:33. In another aspect, said tag region contains a sequence that is substantially identical to one of SEQ ID NO:13, SEQ ID NO:16 and SEQ ID NO:33. In another aspect, said tag region contains a nucleotide sequence selected from the group consisting of: a sequence with at least 95% identity to SEQ ID NO:43 or complement thereof; a sequence with at least 95% identity to SEQ ID NO:44 or complement thereof; a sequence with 100% identity to SEQ ID NO:43 or complement thereof; and a sequence with 100% identity to SEQ ID NO:44 or complement thereof. In one aspect, said tagged amplification oligomer further comprises a tag-closing region, said tag-closing region comprising a nucleotide sequence that is substantially complementary to a portion of said target hybridizing region of said tagged-amplification oligomer. In another aspect, said tag-closing region is 3 to 20 nucleobases in length.

In one aspect, said tagged amplification oligomer comprises at least 95% sequence identity to SEQ ID NO:8, or SEQ ID NO:63. In another aspect, said tagged amplification oligomer comprises 100% sequence identity to SEQ ID NO:8.

In one embodiment, said composition further comprises an additional oligomer comprising a target hybridizing region containing a nucleotide sequence that is configured to hybridize to a region of a target nucleic acid corresponding to residues 1903 to 1945 of SEQ ID NO:4, wherein said additional oligomer is selected from the group consisting of a blocker oligomer, a primer oligomer and a promoter-based amplification oligomer. In one aspect, said additional oligomer is a blocker oligomer. In another aspect, said additional oligomer is a blocker oligomer comprising a sequence that is at least 95% identical to SEQ ID NO:9. In another aspect, said additional oligomer is a blocker oligomer comprising a sequence that is at least 95% identical to SEQ ID NO:10. In another aspect, said additional oligomer is a blocker comprising a sequence that is SEQ ID NO:9. In one aspect, said additional oligomer is a promoter-based amplification oligomer. In another aspect, said additional oligomer is a promoter-based amplification oligomer comprising a target hybridizing region that is 10 to 50 nucleobases in length and contains a nucleotide sequence that is configured to hybridize to all or a portion of a region of a target nucleic acid corresponding to residues 1916 to 1945 SEQ ID NO:4. In another aspect, said additional oligomer is a promoter-based amplification oligomer comprising a target hybridizing region comprising a sequence that is at least 95% identical to SEQ ID NO:42. In another aspect, said additional oligomer is a promoter-based amplification oligomer comprising a target hybridizing region comprising a sequence that is 100% identical to SEQ ID NO:42. In another aspect, said additional oligomer is a promoter-based amplification comprising a sequence that is at least 95% identical to SEQ ID NO:15. In another aspect, said additional oligomer is a promoter-based amplification oligomer comprising a sequence that is 100% identical to SEQ ID NO:15.

In one embodiment, said composition further comprises a tag-targeting amplification oligomer comprising a target hybridizing region that contains a nucleotide sequence configured to specifically hybridize to a tag region of said tagged amplification oligomer or complement thereof. In one aspect, said tag-targeting amplification oligomer comprises a target hybridization region that is 18 to 24 nucleobases in length. In another aspect, said tag-targeting amplification comprises a sequence that is at least 95% identical to a sequence selected from the group consisting of SEQ ID NO:13, SEQ ID NO:16 and SEQ ID NO:33. In another aspect, said tag-targeting amplification oligomer comprises a sequence that is 100% identical to SEQ ID NO:13. In another aspect, said tag-targeting amplification oligomer comprises a sequence that is 100% identical to SEQ ID NO:16. In another aspect, said tag-targeting amplification oligomer comprises a sequence that is 100% identical to SEQ ID NO:33.

In one embodiment, said composition further comprises a first tagged amplification oligomer comprising a target hybridizing region and a tag region, wherein said target hybridizing region is from 15 to 50 nucleobases in length and contains a nucleotide sequence that is configured to hybridize to a region of a target nucleic acid corresponding to residues 1994 to 2036 of SEQ ID NO:4, as is described above, and one or more additional tagged amplification oligomers. In one aspect, said one or more additional tagged amplification oligomers includes a tagged amplification oligomer comprising a nucleic acid sequence that is at least 95% identical to SEQ ID NO:5. In another aspect, said one or more additional tagged amplification oligomers includes a tagged amplification oligomer comprising a nucleic acid sequence that is at least 95% identical to SEQ ID NO:6. In another aspect, said one or more additional tagged amplification oligomers includes a tagged amplification oligomer comprising a nucleic acid sequence that is at least 95% identical to SEQ ID NO:7. In another aspect, said one or more additional tagged amplification oligomers includes a tagged amplification oligomer comprising a nucleic acid sequence that is 100% identical to SEQ ID NO:5. In another aspect, said one or more additional tagged amplification oligomers includes a tagged amplification oligomer comprising a nucleic acid sequence that is 100% identical to SEQ ID NO:6. In another aspect, said one or more additional tagged amplification oligomers includes a tagged amplification oligomer comprising a nucleic acid sequence that is 100% identical to SEQ ID NO:7. In another aspect, said one or more additional tagged amplification oligomers includes a first additional tagged amplification oligomer that is at least 95% identical to SEQ ID NO:5 and a second additional tagged amplification oligomer that is at least 95% identical to SEQ ID NO:6. In another aspect, said one or more additional tagged amplification oligomers includes a first additional tagged amplification oligomer that is at least 95% identical to SEQ ID NO:5 and a second additional tagged amplification oligomer that is at least 95% identical to SEQ ID NO:7. In another aspect, said one or more additional tagged amplification oligomers includes a first additional tagged amplification oligomer that is at least 95% identical to SEQ ID NO:6 and a second additional tagged amplification oligomer that is at least 95% identical to SEQ ID NO:7. In another aspect, said one or more additional tagged amplification oligomers includes a first additional tagged amplification oligomer that is at least 95% identical to SEQ ID NO:5, a second additional tagged amplification oligomer that is at least 95% identical to SEQ ID NO:6 and a third additional tagged amplification oligomer that is at least 95% identical to SEQ ID NO:7.

In one embodiment, said composition comprises at least two oligomers, one of which is a tagged amplification oligomer and the other of which is a blocker oligomer. In one aspect, said tagged amplification oligomer comprises a nucleotide sequence that is at least 95% identical to SEQ ID NO:8. In another aspect, said blocker oligomer comprises a nucleotide sequence that is at least 95% identical to SEQ ID NO:9. In another aspect, said blocker oligomer comprises a nucleotide sequence that is at least 95% identical to SEQ ID NO:10. In one aspect, said tagged amplification oligomer comprises a nucleotide sequence that is 100% identical to SEQ ID NO:8. In another aspect, said blocker oligomer comprises a nucleotide sequence that is 100% identical to SEQ ID NO:9. In another aspect, said blocker oligomer comprises a nucleotide sequence that is 100% identical to SEQ ID NO:10. In another aspect, said tagged amplification oligomer comprises a nucleotide sequence that is 100% identical to SEQ ID NO:8 and said blocker oligomer comprises a nucleotide sequence that is 100% identical to SEQ ID NO:9. In another aspect, said tagged amplification oligomer comprises a nucleotide sequence that is 100% identical to SEQ ID NO:8 and said blocker oligomer comprises a nucleotide sequence that is 100% identical to SEQ ID NO:10.

In one embodiment, said composition further comprises at least two additional oligomers, one of which is a tag-targeting oligomer, the other of which is a promoter based amplification oligomer. In one aspect, said tag-targeting amplification oligomer comprises a nucleotide sequence that is at least 95% identical to SEQ ID NO:13. In another aspect, said promoter-based amplification oligomer comprises a nucleotide sequence that is at least 95% identical to SEQ ID NO:15. In one aspect, said tag-targeting amplification oligomer comprises a nucleotide sequence that is 100% identical to SEQ ID NO:13. In another aspect, said promoter-based amplification oligomer comprises a nucleotide sequence that is 100% identical to SEQ ID NO:15. In another aspect, said tag-targeting amplification oligomer comprises a nucleotide sequence that is 100% identical to SEQ ID NO:13 and said promoter-based amplification oligomer comprises a nucleotide sequence that is 100% identical to SEQ ID NO:15.

In one embodiment, said composition comprises at least two oligomers, one of which is a tagged amplification oligomer comprising a target hybridizing region and a tag region, wherein said target hybridizing region is from 15 to 50 nucleobases in length and contains a nucleotide sequence that is configured to hybridize to a region of a target nucleic acid corresponding to residues 1994 to 2036 of SEQ ID NO:4, as is described above; and the others of which can be selected from the group consisting of: an additional tagged amplification oligomer; a blocker oligomer; a tag-targeting oligomer; and a promoter based amplification oligomer. In one aspect, said tagged amplification oligomer comprises a nucleotide sequence that is at least 95% identical to SEQ ID NO:8. In another aspect, said blocker oligomer comprises a nucleotide sequence that is at least 95% identical to SEQ ID NO:9. In another aspect, said blocker oligomer comprises a nucleotide sequence that is at least 95% identical to SEQ ID NO:10. In another aspect, said tag-targeting amplification oligomer comprises a nucleotide sequence that is at least 95% identical to SEQ ID NO:13. In another aspect, said promoter-based amplification oligomer comprises a nucleotide sequence that is at least 95% identical to SEQ ID NO:15. In another aspect, said additional tagged amplification oligomer comprises a nucleic acid sequence that is at least 95% identical to SEQ ID NO:5. In another aspect, said additional tagged amplification oligomer comprises a nucleic acid sequence that is at least 95% identical to SEQ ID NO:6. In another aspect, said additional tagged amplification oligomer comprises a nucleic acid sequence that is at least 95% identical to SEQ ID NO:7. In one aspect, said tagged amplification oligomer comprises a nucleotide sequence that is 100% identical to SEQ ID NO:8. In another aspect, said blocker oligomer comprises a nucleotide sequence that is 100% identical to SEQ ID NO:9. In another aspect, said blocker oligomer comprises a nucleotide sequence that is 100% identical to SEQ ID NO:10. In one aspect, said tag-targeting amplification oligomer comprises a nucleotide sequence that is 100% identical to SEQ ID NO:13. In another aspect, said promoter-based amplification oligomer comprises a nucleotide sequence that is 100% identical to SEQ ID NO:15. In another aspect, said tagged amplification oligomer comprises a nucleotide sequence that is 100% identical to SEQ ID NO:8, said blocker oligomer comprises a nucleotide sequence that is 100% identical to SEQ ID NO:9, said tag-targeting amplification oligomer comprises a nucleotide sequence that is 100% identical to SEQ ID NO:13, and said promoter-based amplification oligomer comprises a nucleotide sequence that is 100% identical to SEQ ID NO:15. In another aspect, said tagged amplification oligomer comprises a nucleotide sequence that is 100% identical to SEQ ID NO:8, said blocker oligomer comprises a nucleotide sequence that is 100% identical to SEQ ID NO:10, said tag-targeting amplification oligomer comprises a nucleotide sequence that is 100% identical to SEQ ID NO:13, and said promoter-based amplification oligomer comprises a nucleotide sequence that is 100% identical to SEQ ID NO:15. In another aspect, said additional tagged amplification oligomer comprises a nucleic acid sequence that is 100% identical to SEQ ID NO:5. In another aspect, said additional tagged amplification oligomer comprises a nucleic acid sequence that is 100% identical to SEQ ID NO:6. In another aspect, said additional tagged amplification oligomer comprises a nucleic acid sequence that is 100% identical to SEQ ID NO:7.

In one embodiment, there is a reaction mixture for generating from one or more *Spiroplasma* species in a sample an initial nucleic acid amplification product containing a tag sequence or complement thereof, wherein said reaction mixture comprises a tagged amplification oligomer comprising a target hybridizing region and a tag region, wherein said target hybridizing region is from 15 to 50 nucleobases in length and contains a nucleotide sequence that is configured to hybridize to a region of a target nucleic acid corresponding to residues 1994 to 2036 of SEQ ID NO:4, as is described above. In one aspect, said initial amplification product comprises a tag sequence that is from 10 to 25 nucleobases in length. In another aspect said initial amplification product comprises a tag sequence that is from 18 to 24 nucleobases in length. In another aspect, said initial amplification product comprises a tag sequence that is 19 nucleobases in length. In another aspect, said initial amplification product comprises a tag sequence that contains a sequence that is substantially complementary to one of SEQ ID NO:13, SEQ ID NO:16 and SEQ ID NO:33. In another aspect, said initial amplification product comprises a tag sequence that contains a sequence that is substantially identical to one of SEQ ID NO:13, SEQ ID NO:16 and SEQ ID NO:33. In another aspect, said initial amplification product comprises a tag sequence that contains a nucleotide sequence selected from the group consisting of: a sequence with at least 95% identity to SEQ ID NO:43 or complement thereof; a sequence with at least 95% identity to SEQ ID NO:44 or complement thereof; a sequence with 100% identity to SEQ ID NO:43 or complement thereof; and a sequence with 100% identity to SEQ ID NO:44 or complement thereof.

In one embodiment, there is an amplification reaction mixture for generating from an initial nucleic acid amplification product containing a tag sequence or complement thereof, as described above, a further nucleic acid amplification product, wherein said amplification reaction mixture comprises a tag-targeting amplification oligomer comprising a target hybridizing region containing a nucleic acid sequence configured to specifically hybridize to said tag sequence, or complement thereof, that contained within the nucleotide sequence of said initial nucleic acid amplification product, and wherein said amplification reaction mixture comprises a promoter-based amplification oligomer comprising a target hybridizing region that is 10 to 50 nucleobases in length and contains a nucleotide sequence that is configured to hybridize to all or a portion of a region of a target nucleic acid corresponding to residues 1916 to 1945 of SEQ ID NO:4. In one aspect, said target hybridizing region of said promoter-based amplification oligomer comprises a sequence that is at least 95% identical to SEQ ID NO:42. In another aspect, said target hybridizing region of said promoter-based amplification oligomer comprises a sequence that is 100% identical to SEQ ID NO:42. In another aspect, said promoter-based amplification oligomer comprising a sequence that is 100% identical to SEQ ID NO:15. In another aspect, said target hybridizing region of said tag-targeting amplification oligomer is 18 to 24 nucleobases in length. In another aspect, said tag-targeting amplification oligomer comprises a sequence that is at least 95% identical to a sequence selected from the group consisting of: SEQ ID NO:13, SEQ ID NO:16 and SEQ ID NO:33. In another aspect, said tag-targeting amplification oligomer comprises a sequence that is 100% identical to a sequence selected from the group consisting of: SEQ ID NO:13, SEQ ID NO:16 and SEQ ID NO:33.

In one aspect, there is provided an initial amplification product that was generated using a tagged amplification oligomer comprising a target hybridizing region and a tag region, wherein said target hybridizing region is from 15 to 50 nucleobases in length and contains a nucleotide sequence that is configured to hybridize to a region of a target nucleic acid corresponding to residues 1994 to 2036 of SEQ ID NO:4, wherein said initial amplification product contains a nucleotide sequence comprising a tag sequence region, and wherein the sequence of said tag region is from 10 to 25 nucleobases in length. In another aspect said initial amplification product comprises a tag sequence that is from 18 to 24 nucleobases in length. In another aspect, said initial amplification product comprises a tag sequence that is 19 nucleobases in length. In another aspect, said initial amplification product comprises a tag sequence that contains a sequence that is substantially complementary to one of SEQ ID NO:13, SEQ ID NO:16 and SEQ ID NO:33. In another aspect, said initial amplification product comprises a tag sequence that contains a sequence that is substantially identical to one of SEQ ID NO:13, SEQ ID NO:16 and SEQ ID NO:33. In another aspect, said initial amplification product comprises a tag sequence that contains a nucleotide sequence selected from the group consisting of: a sequence with at least 95% identity to SEQ ID NO:43 or complement thereof; a sequence with at least 95% identity to SEQ ID NO:44 or complement thereof; a sequence with 100% identity to SEQ ID NO:43 or complement thereof; and a sequence with 100% identity to SEQ ID NO:44 or complement thereof. In one aspect, there is provided an amplification product generated from said initial amplification product and containing a nucleotide sequence comprising a tag sequence region, wherein the sequence of said tag region is from 10 to 25 nucleobases in length. In another aspect said tag sequence region is from 18 to 24 nucleobases in length. In another aspect, said tag sequence region is 19 nucleobases in length. In another aspect, said tag sequence region contains a sequence that is substantially complementary to one of SEQ ID NO:13, SEQ ID NO:16 and SEQ ID NO:33. In another aspect, said tag sequence region contains a sequence that is substantially identical to one of SEQ ID NO:13, SEQ ID NO:16 and SEQ ID NO:33. In another aspect, said tag sequence region contains a nucleotide sequence selected from the group consisting of: a sequence with at least 95% identity to SEQ ID NO:43 or complement thereof; a sequence with at least 95% identity to SEQ ID NO:44 or complement thereof; a sequence with 100% identity to SEQ ID NO:43 or complement thereof; and a sequence with 100% identity to SEQ ID NO:44 or complement thereof.

In one embodiment, there is provided a method for the in vitro amplification of a nucleic acid from one or more *Spiroplasma* species in a sample, comprising the steps of: (a.) contacting a sample with a tagged amplification oligomer comprising a target hybridizing region that is from 15 to 50 nucleobases in length and contains a nucleotide sequence that is configured to hybridize to a region of a target nucleic acid corresponding to residues 1994 to 2036 of SEQ ID NO:4; and (b.) providing suitable conditions for performing an amplification reaction.

In one aspect said nucleotide sequence contained within said tagged amplification oligomer target hybridizing region has at least one of a nucleotide addition, a nucleotide deletion, a nucleotide mismatch, a modified nucleotide or a combination thereof relative to a corresponding residue of said target nucleic acid. In another aspect, said target hybridizing region of said tagged amplification oligomer is from 18 to 28 nucleobases in length. In another aspect, said target hybridizing region of said tagged amplification oligomer is 15 to 30 nucleobases in length and contains a nucleotide sequence that is configured to hybridize to a region of a target nucleic acid corresponding to residues 1994 to 2017 of SEQ ID NO:4. In another aspect, said target hybridizing region of said tagged amplification oligomer comprises at least 95% sequence identity to SEQ ID NO:58, SEQ ID NO:59, SEQ ID NO:60, SEQ ID NO:61 or SEQ ID NO:62. In one aspect, said tag region of said tagged amplification oligomer is from 10 to 25 nucleobases in length. In another aspect, said tag region is from 18 to 24 nucleobases in length. In another aspect, said tag region is 19 nucleobases in length. In another aspect, said tag region contains a sequence that is substantially complementary to one of SEQ ID NO:13, SEQ ID NO:16 and SEQ ID NO:33. In another aspect, said tag region contains a sequence that is substantially identical to one of SEQ ID NO:13, SEQ ID NO:16 and SEQ ID NO:33. In another aspect, said tag region contains a nucleotide sequence selected from the group consisting of: a sequence with at least 95% identity to SEQ ID NO:43 or complement thereof; a sequence with at least 95% identity to SEQ ID NO:44 or complement thereof; a sequence with 100% identity to SEQ ID NO:43 or complement thereof; and a sequence with 100% identity to SEQ ID NO:44 or complement thereof. In one aspect, said tagged amplification oligomer further comprises a tag-closing region, said tag-closing region comprising a nucleotide sequence that is substantially complementary to a portion of said target hybridizing region of said tagged-amplification oligomer. In another aspect, said tag-closing region is 3 to 20 nucleobases in length. In one aspect, said tagged amplification oligomer comprises at least 95% sequence identity to SEQ ID NO:8, or SEQ ID NO:63. In another aspect, said tagged amplification oligomer comprises 100% sequence identity to SEQ ID NO:8.

In one aspect, said method further comprises the step of contacting said sample with an additional oligomer. In another aspect, said additional oligomer is a blocker oligomer. In another aspect, said additional oligomer is a blocker oligomer comprising a sequence that is at least 95% identical to SEQ ID NO:9. In another aspect, said additional oligomer is a blocker oligomer comprising a sequence that is at least 95% identical to SEQ ID NO:10. In another aspect, said additional oligomer is a blocker comprising a sequence that is SEQ ID NO:9. In one aspect, said method comprises contacting said sample with a tagged amplification oligomer with a nucleotide sequence that is at least 95% identical to SEQ ID NO:8, a nucleotide sequence that is at least 95% identical to SEQ ID NO:63, or a nucleotide sequence that is 100% identical to SEQ ID NO:8; and wherein said contacting step further comprises contacting said sample with a blocker oligomer. In another aspect, said blocker oligomer comprises a sequence that is at least 95% identical to SEQ ID NO:9. In another aspect, said blocker oligomer comprises a sequence that is at least 95% identical to SEQ ID NO:10. In another aspect, said blocker comprises a sequence that is SEQ ID NO:9.

In one aspect, said method at step (b.) results in an initial amplification product containing a tag sequence, or complement thereof. In another aspect, there is provided an initial amplification product with a nucleotide sequence comprising a tag sequence region, wherein said tag sequence is from 10 to 25 nucleobases in length. In another aspect said initial amplification product comprises a tag sequence that is from 18 to 24 nucleobases in length. In another aspect, said initial amplification product comprises a tag sequence that is 19 nucleobases in length. In another aspect, said initial amplification product comprises a tag sequence that contains a sequence that is substantially complementary to one of SEQ ID NO:13, SEQ ID NO:16 and SEQ ID NO:33. In another aspect, said initial amplification product comprises a tag sequence that contains a sequence that is substantially identical to one of SEQ ID NO:13, SEQ ID NO:16 and SEQ ID NO:33. In another aspect, said initial amplification product comprises a tag sequence that contains a nucleotide sequence selected from the group consisting of: a sequence with at least 95% identity to SEQ ID NO:43 or complement thereof; a sequence with at least 95% identity to SEQ ID NO:44 or complement thereof; a sequence with 100% identity to SEQ ID NO:43 or complement thereof; and a sequence with 100% identity to SEQ ID NO:44 or complement thereof. In one aspect, said initial amplification product has a 3' end defined by a blocker oligomer. In another aspect, said initial amplification product has a 3' end that is not defined by a blocker oligomer.

In one embodiment of the current invention, there is provided a method for the in vitro amplification of an initial amplification product, comprising the steps of (c.) contacting the sample with at least one additional amplification oligomer selected from the group consisting of a tag-targeting amplification oligomer, a primer oligomer and a promoter-based amplification oligomer; and (d.) providing suitable conditions for performing a second amplification reaction. In one aspect, the oligomers of step (c.) and the oligomers of step (a.) are contacted to said sample at the same time point. In one aspect, the oligomers of step (c.) and the oligomers of step (a.) are contacted to the sample and a single amplification reaction is performed. In this aspect, steps (b.) and (d.) are combined to provide suitable conditions for performing an amplification reaction to generate an initial amplification product and for performing an amplification reaction generate a second amplification product therefrom. Though all of the amplification oligomers are present in this combined amplification reaction aspect, the tag-targeting amplification oligomers are configured to not participate in amplification until a tagged amplification oligomer is incorporated into an initial amplification product. In another aspect, the oligomers of step (c.) and the oligomers of step (a.) are contacted to said sample at separate time points. In one aspect, the method comprises the step of (c.) providing to an amplification product generated in step (b.) a second reaction mixture comprising a tag-targeting amplification oligomer consisting essentially of a target hybridizing region that contains a nucleotide sequence configured to specifically hybridize to a tag region of said tagged amplification oligomer, and comprising a second amplification oligomer; and (d.) providing suitable conditions for performing a second amplification reaction. In one aspect for generating an amplification product, said sample is contacted with a first additional amplification oligomer that is a tag-targeting amplification oligomer comprising a target hybridizing region that contains a nucleotide sequence configured to specifically hybridize to a tag region of said, or complement thereof in an initial amplification oligomer, and is contacted with a second additional amplification oligomer. In another aspect, said tag-targeting amplification oligomer comprises a target hybridization region that is 18 to 24 nucleobases in length. In another aspect, said tag-targeting amplification oligomer comprises a sequence that is at least 95% identical to a sequence selected from the group consisting of SEQ ID NO:13, SEQ ID NO:16 and SEQ ID NO:33. In another aspect, said tag-targeting amplification oligomer comprises a sequence that is 100% identical to SEQ ID NO:13. In another aspect, said tag-targeting amplification oligomer comprises a sequence that is 100% identical to SEQ ID NO:16. In another aspect, said tag-targeting amplification oligomer comprises a sequence that is 100% identical to SEQ ID NO:33. In one aspect, said second amplification oligomer is a primer amplification oligomer, a promoter based amplification oligomer or a tagged amplification oligomer. In another aspect, said second amplification oligomer is a promoter-based amplification oligomer comprising a target hybridizing region that is 10 to 50 nucleobases in length and contains a nucleotide sequence that is configured to hybridize to all or a portion of a region of a target nucleic acid corresponding to residues 1916 to 1945 of SEQ ID NO:4. In another aspect, said second additional amplification oligomer is a promoter-based amplification oligomer comprising a target hybridizing region that comprises a sequence that is at least 95% identical to SEQ ID NO:42. In another aspect, said second additional amplification oligomer is a promoter-based amplification oligomer that comprises a sequence that is 100% identical to SEQ ID NO:42. In another aspect, said second additional amplification oligomer is a promoter-based amplification oligomer that comprises a sequence that is 100% identical to SEQ ID NO:15.

In one aspect for the in vitro amplification of a nucleic acid from one or more *Spiroplasma* species in a sample, there is provided at least one tagged amplification oligomer that is at least 95% identical to SEQ ID NO:8; at least one blocker oligomer that is at least 95% identical to SEQ ID NO:9; at least one tag-targeting amplification oligomer that is at least 95% identical to SEQ ID NO:13 and at least one promoter-based amplification oligomer that is at least 95% identical to SEQ ID NO:15. In another aspect, said at least one tagged amplification oligomer is 100% identical to SEQ ID NO:8. In another aspect, said at least one blocker oligomer is 100% identical to SEQ ID NO:9. In another aspect, said at least one tag-targeting amplification oligomer is 100% identical to SEQ ID NO:13. In another aspect, said at least one promoter-based amplification oligomer is 95% identical to SEQ ID NO:15. In another aspect there are provided one or more additional tagged amplification oligomers each or which could be selected from the group consisting of: a tagged amplification oligomer with at least 95% identity to SEQ ID NO:5; a tagged amplification oligomer with at least 95% identity to SEQ ID NO:6, a tagged amplification oligomer with at least 95% identity to SEQ ID NO:7, a tagged amplification oligomer with 100% identity to SEQ ID NO:5, a tagged amplification oligomer with 100% identity to SEQ ID NO:6 and a tagged amplification oligomer with 100% identity to SEQ ID NO:7.

In one embodiment there is further provided an analysis step, wherein an initial amplification product, an amplification product or both are analyzed. In one aspect, said analysis comprises a detection step to identify the presence or absence of an initial amplification product from an amplification reaction in step (b.), an amplification product generated in step (d.) or both initial amplification and amplification products generated in steps (b.) and (d.). In another aspect, said detection step is a probe-based detection step. In another aspect, said probe-based detection step uses a probe with a nucleotide sequence that is at least 95% identical to SEQ ID NO:14. In another aspect, said detection step is a probe-based detection step. In another aspect, said probe-based detection step uses a probe with a nucleotide sequence that is 100% identical to SEQ ID NO:14.

In one embodiment of the invention, there is provided a composition for determining the presence or absence of one or more species from the Mollicutes class in a sample, said composition comprising at least two tagged amplification oligomers, each of which individually comprises a target hybridizing region and a tag region, wherein individually, each of the target hybridizing regions of the at least two tagged amplification oligomers are selected from the group consisting of: a tagged amplification oligomer comprising a target hybridizing region that is from 15 to 50 nucleobases in length and contains a nucleotide sequence that is configured to hybridize to a region of a target nucleic acid corresponding to residues 5065 to 5088 of SEQ ID NO:1; a tagged amplification oligomer comprising a target hybridizing region that is from 15 to 50 nucleobases in length and contains a nucleotide sequence that is configured to hybridize to a region of a target nucleic acid corresponding to residues 4752 to 4798 of SEQ ID NO:2; a tagged amplification oligomer comprising a target hybridizing region that is from 15 to 50 nucleobases in length and contains a nucleotide sequence that is configured to hybridize to a region of a target nucleic acid corresponding to residues 1954 to 2006 of SEQ ID NO:3; and a tagged amplification oligomer comprising a target hybridizing region that is from 15 to 50 nucleobases in length and contains a nucleotide sequence that is configured to hybridize to a region of a target nucleic acid corresponding to residues 1994 to 2036 of SEQ ID NO:4.

In one aspect, one of said at least two tagged amplification oligomers comprises a target hybridizing region that is from 20 to 24 nucleobases in length and contains a nucleotide sequence that is configured to hybridize to a region of a target nucleic acid corresponding to residues 5065 to 5088 of SEQ ID NO:1. In another aspect, said target-hybridizing region of said tagged amplification oligomer may contain one or more of a nucleotide addition, a nucleotide deletion, a nucleotide mismatch, a modified nucleotide or a combination thereof relative to a corresponding residue of said target nucleic acid. In another aspect, said target hybridizing region comprises at least 95% sequence identity to SEQ ID NO:38 or SEQ ID NO:39. In one aspect, said tag region of said tagged amplification oligomer is from 10 to 25 nucleobases in length. In another aspect, said tag region is from 18 to 24 nucleobases in length. In another aspect, said tag region is 19 nucleobases in length. In another aspect, said tag region contains a sequence that is substantially complementary to one of SEQ ID NO:13, SEQ ID NO:16 and SEQ ID NO:33. In another aspect, said tag region contains a sequence that is substantially identical to one of SEQ ID NO:13, SEQ ID NO:16 and SEQ ID NO:33. In another aspect, said tag region contains a nucleotide sequence selected from the group consisting of: a sequence with at least 95% identity to SEQ ID NO:43 or complement thereof; a sequence with at least 95% identity to SEQ ID NO:44 or complement thereof; a sequence with 100% identity to SEQ ID NO:43 or complement thereof; and a sequence with 100% identity to SEQ ID NO:44 or complement thereof. In one aspect, said tagged amplification oligomer further comprises a tag-closing region, said tag-closing region comprising a nucleotide sequence that is substantially complementary to a portion of said target hybridizing region of said tagged-amplification oligomer. In another aspect, said tag-closing region is 3 to 20 nucleobases in length.

In one aspect, said tagged amplification oligomer comprises at least 95% sequence identity to a sequence selected from the group consisting of SEQ ID NO:5, SEQ ID NO:17, SEQ ID NO:18, SEQ ID NO:30, SEQ ID NO:40 and SEQ ID NO:41. In another aspect, said tagged amplification oligomer comprises 100% sequence identity to SEQ ID NO:5. In another aspect, said tagged amplification oligomer comprises 100% sequence identity to SEQ ID NO:17. In another aspect, said tagged amplification oligomer comprises 100% sequence identity to SEQ ID NO:18. In another aspect, said tagged amplification oligomer comprises 100% sequence identity to SEQ ID NO:30.

In one aspect, one of said at least two tagged amplification oligomers comprises a target hybridizing region that is from 18 to 28 nucleobases in length and contains a nucleotide sequence that is configured to hybridize to a region of a target nucleic acid corresponding to residues 4752 to 4798 of SEQ ID NO:2. In another aspect, target-hybridizing region of said tagged amplification oligomer may contain one or more of a nucleotide addition, a nucleotide deletion, a nucleotide mismatch, a modified nucleotide or a combination thereof relative to a corresponding residue of said target nucleic acid. In another aspect, said target hybridizing region comprises at least 95% sequence identity to SEQ ID NO:45, SEQ ID NO:46, SEQ ID NO:47 or SEQ ID NO:48. In another aspect, said target hybridizing region is 15 to 30 nucleobases in length and contains a nucleotide sequence that is configured to hybridize to a region of a target nucleic acid corresponding to residues 4776 to 4798 of SEQ ID NO:2. In one aspect, said tag region of said tagged amplification oligomer is from 10 to 25 nucleobases in length. In another aspect, said tag region is from 18 to 24 nucleobases in length. In another aspect, said tag region is 19 nucleobases in length. In another aspect, said tag region contains a sequence that is substantially complementary to one of SEQ ID NO:13, SEQ ID NO:16 and SEQ ID NO:33. In another aspect, said tag region contains a sequence that is substantially identical to one of SEQ ID NO:13, SEQ ID NO:16 and SEQ ID NO:33. In another aspect, said tag region contains a nucleotide sequence selected from the group consisting of: a sequence with at least 95% identity to SEQ ID NO:43 or complement thereof; a sequence with at least 95% identity to SEQ ID NO:44 or complement thereof; a sequence with 100% identity to SEQ ID NO:43 or complement thereof; and a sequence with 100% identity to SEQ ID NO:44 or complement thereof. In one aspect, said tagged amplification oligomer further comprises a tag-closing region, said tag-closing region comprising a nucleotide sequence that is substantially complementary to a portion of said target hybridizing region of said tagged-amplification oligomer. In another aspect, said tag-closing region is 3 to 20 nucleobases in length.

In one aspect, said tagged amplification oligomer comprises at least 95% sequence identity to a sequence selected from the group consisting of SEQ ID NO:6, SEQ ID NO:23, SEQ ID NO:24 and SEQ ID NO:49. In another aspect, said tagged amplification oligomer comprises 100% sequence identity to SEQ ID NO:6. In another aspect, said tagged amplification oligomer comprises 100% sequence identity to SEQ ID NO:23. In another aspect, said tagged amplification oligomer comprises 100% sequence identity to SEQ ID NO:24.

In one aspect, one of said at least two tagged amplification oligomers comprises a target hybridizing region that is from 19 to 24 nucleobases in length and contains a nucleotide sequence that is configured to hybridize to a region of a target nucleic acid corresponding to residues 1954 to 2006 of SEQ ID NO:3. In another aspect, target-hybridizing region of said tagged amplification oligomer may contain one or more of a nucleotide addition, a nucleotide deletion, a nucleotide mismatch, a modified nucleotide or a combination thereof relative to a corresponding residue of said target nucleic acid. In another aspect, said target hybridizing region comprises at least 95% sequence identity to SEQ ID NO:50, SEQ ID NO:51, SEQ ID NO:52, SEQ ID NO:53, SEQ ID NO:54 or SEQ ID NO:55. In another aspect, said target hybridizing region is 15 to 30 nucleobases in length and contains a nucleotide sequence that is configured to hybridize to a region of a target nucleic acid corresponding to residues 1973 to 2006 of SEQ ID NO:3. In one aspect, said tag region of said tagged amplification oligomer is from 10 to 25 nucleobases in length. In another aspect, said tag region is from 18 to 24 nucleobases in length. In another aspect, said tag region is 19 nucleobases in length. In another aspect, said tag region contains a sequence that is substantially complementary to one of SEQ ID NO:13, SEQ ID NO:16 and SEQ ID NO:33. In another aspect, said tag region contains a sequence that is substantially identical to one of SEQ ID NO:13, SEQ ID NO:16 and SEQ ID NO:33. In another aspect, said tag region contains a nucleotide sequence selected from the group consisting of: a sequence with at least 95% identity to SEQ ID NO:43 or complement thereof; a sequence with at least 95% identity to SEQ ID NO:44 or complement thereof; a sequence with 100% identity to SEQ ID NO:43 or complement thereof; and a sequence with 100% identity to SEQ ID NO:44 or complement thereof. In one aspect, said tagged amplification oligomer further comprises a tag-closing region, said tag-closing region comprising a nucleotide sequence that is substantially complementary to a portion of said target hybridizing region of said tagged-amplification oligomer. In another aspect, said tag-closing region is 3 to 20 nucleobases in length.

In one aspect, said tagged amplification oligomer comprises at least 95% sequence identity to SEQ ID NO:7, SEQ ID NO:31, SEQ ID NO:56 or SEQ ID NO:57. In another aspect, said tagged amplification oligomer comprises 100% sequence identity to SEQ ID NO:7. In another aspect, said tagged amplification oligomer comprises 100% sequence identity to SEQ ID NO:31.

In one aspect, one of said at least two tagged amplification oligomers comprises a target hybridizing region that is from 20 to 25 nucleobases in length and contains a nucleotide sequence that is configured to hybridize to a region of a target nucleic acid corresponding to residues 1994 to 2036 of SEQ ID NO:4. In another aspect, target-hybridizing region of said tagged amplification oligomer may contain one or more of a nucleotide addition, a nucleotide deletion, a nucleotide mismatch, a modified nucleotide or a combination thereof relative to a corresponding residue of said target nucleic acid. In another aspect, said target hybridizing region comprises at least 95% sequence identity to SEQ ID NO:58, SEQ ID NO:59, SEQ ID NO:60, SEQ ID NO:61 or SEQ ID NO:62. In another aspect, said target hybridizing region is 15 to 30 nucleobases in length and contains a nucleotide sequence that is configured to hybridize to a region of a target nucleic acid corresponding to residues 1994 to 2017 of SEQ ID NO:4. In one aspect, said tag region of said tagged amplification oligomer is from 10 to 25 nucleobases in length. In another aspect, said tag region is from 18 to 24 nucleobases in length. In another aspect, said tag region is 19 nucleobases in length. In another aspect, said tag region contains a sequence that is substantially complementary to one of SEQ ID NO:13, SEQ ID NO:16 and SEQ ID NO:33. In another aspect, said tag region contains a sequence that is substantially identical to one of SEQ ID NO:13, SEQ ID NO:16 and SEQ ID NO:33. In another aspect, said tag region contains a nucleotide sequence selected from the group consisting of: a sequence with at least 95% identity to SEQ ID NO:43 or complement thereof; a sequence with at least 95% identity to SEQ ID NO:44 or complement thereof; a sequence with 100% identity to SEQ ID NO:43 or complement thereof; and a sequence with 100% identity to SEQ ID NO:44 or complement thereof. In one aspect, said tagged amplification oligomer further comprises a tag-closing region, said tag-closing region comprising a nucleotide sequence that is substantially complementary to a portion of said target hybridizing region of said tagged-amplification oligomer. In another aspect, said tag-closing region is 3 to 20 nucleobases in length. In one aspect, said tagged amplification oligomer comprises at least 95% sequence identity to SEQ ID NO:8, or SEQ ID NO:63. In another aspect, said tagged amplification oligomer comprises 100% sequence identity to SEQ ID NO:8.

In one aspect, said at least two tagged amplification oligomers comprises SEQ ID NO:5 and a second tagged amplification oligomer with a sequence that is at least 95% identical to SEQ ID NO:6, SEQ ID NO:7, or SEQ ID NO:8, or that is 100% identical to SEQ ID NO:6, SEQ ID NO:7 or SEQ ID NO:8. In another aspect, said at least two tagged amplification oligomers comprises SEQ ID NO:6 and a second tagged amplification oligomer that is at least 95% identical to SEQ ID NO:5, SEQ ID NO:7, or SEQ ID NO:8, or that is 100% identical to SEQ ID NO:5, SEQ ID NO:7 or SEQ ID NO:8. In another aspect, said at least two tagged amplification oligomers comprises SEQ ID NO:7 and a second tagged amplification oligomer that is at least 95% identical to SEQ ID NO:5, SEQ ID NO:6, or SEQ ID NO:8, or that is 100% identical to SEQ ID NO:5, SEQ ID NO:6 or SEQ ID NO:8. In another aspect, said at least two tagged amplification oligomers comprises SEQ ID NO:8 and a second tagged amplification oligomer that is at least 95% identical to SEQ ID NO:5, SEQ ID NO:6, or SEQ ID NO:7, or that is 100% identical to SEQ ID NO:5, SEQ ID NO:6 or SEQ ID NO:7. In another aspect, said at least two tagged amplification oligomers comprises three tagged amplification oligomers each of the three individually being a tagged amplification oligomer that is at least 95% identical to SEQ ID NO:5, SEQ ID NO:6, SEQ ID NO:7, or SEQ ID NO:8, or that is 100% identical to SEQ ID NO:5, SEQ ID NO:6, SEQ ID NO:7 or SEQ ID NO:8. In another aspect, said at least two tagged amplification oligomers comprises four tagged amplification oligomers each of the four individually being a tagged amplification oligomer that is at least 95% identical to SEQ ID NO:5, SEQ ID NO:6, SEQ ID NO:7, or SEQ ID NO:8, or that is 100% identical to SEQ ID NO:5, SEQ ID NO:6, SEQ ID NO:7 or SEQ ID NO:8.

In one embodiment, said composition further comprises at least one additional oligomer, wherein said at least one additional oligomer is selected from the group consisting of: a blocker oligomer, a primer oligomer and a promoter-based amplification oligomer. In one aspect, one of said at least one additional oligomer is a blocker oligomer. In another aspect, said blocker oligomer is at least 95% identical to SEQ ID NO:9. In another aspect, said blocker oligomer is at least 95% identical to SEQ ID NO:10. In another aspect, said blocker oligomer is SEQ ID NO:9. In another aspect, said blocker oligomer is SEQ ID NO:10. In another aspect, said at least one additional oligomer comprises two blocker oligomers, one of which is at least 95% identical to SEQ ID NO:9; or one of which is at least 95% identical to SEQ ID NO:10; or one of which is at least 95% identical to SEQ ID NO:9 and another of which is at least 95% identical to SEQ ID NO:10; or one of which is 100% identical to SEQ ID NO:9; or one of which is 100% identical to SEQ ID NO:10; or one of which is at least 95% identical to SEQ ID NO:9 and another of which is 100% identical to SEQ ID NO:10; or one of which is 100% identical to SEQ ID NO:9 and another of which is at least 95% identical to SEQ ID NO:10; or one of which is 100% identical to SEQ ID NO:9 and another of which is 100% identical to SEQ ID NO:10. In one aspect, one of said at least one additional oligomer is a promoter-based amplification oligomer. In another aspect, said promoter-based amplification oligomer comprises a target hybridizing region that is 10 to 50 nucleobases in length and contains a nucleotide sequence that is configured to hybridize to all or a portion of a region of a target nucleic acid corresponding to residues 5003 to 5045 SEQ ID NO:1. In another aspect, said promoter-based amplification oligomer comprises a target hybridizing region that is at least 95% identical to SEQ ID NO:42. In another aspect, said promoter-based amplification oligomer comprises a target hybridizing region that is 100% identical to SEQ ID NO:42. In another aspect, said a promoter-based amplification is at least 95% identical to SEQ ID NO:15. In another aspect, said promoter-based amplification oligomer is 100% identical to SEQ ID NO:15.

In one embodiment, said composition further comprises a tag-targeting amplification oligomer comprising a target hybridizing region that contains a nucleotide sequence configured to specifically hybridize to a tag region of said tagged amplification oligomer or complement thereof. In one aspect, said tag-targeting amplification oligomer comprises a target hybridization region that is 18 to 24 nucleobases in length. In another aspect, said tag-targeting amplification oligomer comprises a sequence that is at least 95% identical to a sequence selected from the group consisting of SEQ ID NO:13, SEQ ID NO:16 and SEQ ID NO:33. In another aspect, said tag-targeting amplification oligomer comprises a sequence that is 100% identical to SEQ ID NO:13. In another aspect, said tag-targeting amplification oligomer comprises a sequence that is 100% identical to SEQ ID NO:16. In another aspect, said tag-targeting amplification oligomer comprises a sequence that is 100% identical to SEQ ID NO:33.

In one embodiment, of the invention there is provided at least two tagged amplification oligomers selected from the group consisting of a tagged amplification oligomer comprising a target hybridizing region that is from 15 to 50 nucleobases in length and contains a nucleotide sequence that is configured to hybridize to a region of a target nucleic acid corresponding to residues 5065 to 5088 of SEQ ID NO:1; a tagged amplification oligomer comprising a target hybridizing region that is from 15 to 50 nucleobases in length and contains a nucleotide sequence that is configured to hybridize to a region of a target nucleic acid corresponding to residues 4752 to 4798 of SEQ ID NO:2; a tagged amplification oligomer comprising a target hybridizing region that is from 15 to 50 nucleobases in length and contains a nucleotide sequence that is configured to hybridize to a region of a target nucleic acid corresponding to residues 1954 to 2006 of SEQ ID NO:3; and a tagged amplification oligomer comprising a target hybridizing region that is from 15 to 50 nucleobases in length and contains a nucleotide sequence that is configured to hybridize to a region of a target nucleic acid corresponding to residues 1994 to 2036 of SEQ ID NO:4, as are described above; and there is at least one additional oligomer selected from the group consisting of: a blocker oligomer; a tag-targeting oligomer; and a promoter based amplification oligomer. In one aspect, said blocker oligomer is at least 95% identical to SEQ ID NO:9 or SEQ ID NO:10. In another aspect, said blocker oligomer is 100% identical to SEQ ID NO:9 or SEQ ID NO:10. In one aspect, said tag-targeting amplification oligomer is at least 95% identical to SEQ ID NO:13. In another aspect, said tag-targeting amplification oligomer is 100% identical to SEQ ID NO:13. In one aspect, said promoter-based amplification oligomer is at least 95% identical to SEQ ID NO:15. In another aspect, said promoter-based amplification oligomer is 100% identical to SEQ ID NO:15. In one aspect, said composition comprises a tagged amplification oligomer that is at least 95% identical to SEQ ID NO:5, a tagged amplification oligomer that is at least 95% identical to SEQ ID NO:7, a blocker oligomer that is at least 95% identical to SEQ ID NO:9 and a promoter-based amplification oligomer that is at least 95% identical to SEQ ID NO:15. In one aspect, said composition comprises a tagged amplification oligomer that is at least 95% identical to SEQ ID NO:6, a tagged amplification oligomer that is at least 95% identical to SEQ ID NO:8, a blocker oligomer that is at least 95% identical to SEQ ID NO:10 and a promoter-based amplification oligomer that is at least 95% identical to SEQ ID NO:15. In another aspect, said composition comprises a tagged amplification oligomer that is at least 95% identical to SEQ ID NO:5, a tagged amplification oligomer that is at least 95% identical to SEQ ID NO:6, a tagged amplification oligomer that is at least 95% identical to SEQ ID NO:7, a tagged amplification oligomer that is at least 95% identical to SEQ ID NO:8, a blocker oligomer that is at least 95% identical to SEQ ID NO:9, a blocker oligomer that is at least 95% identical to SEQ ID NO:10 and a promoter-based amplification oligomer that is at least 95% identical to SEQ ID NO:15. In another aspect, said composition comprises SEQ ID NO:5, SEQ ID NO:6, SEQ ID NO:7, SEQ ID NO:8, SEQ ID NO:9, SEQ ID NO:10 and SEQ ID NO:15.

In one embodiment, there is a reaction mixture for generating from one or more species of the class Mollicutes in a sample an initial nucleic acid amplification product containing a tag sequence or complement thereof, wherein said reaction mixture comprises at least two tagged amplification oligomers, each of which individually comprises a target hybridizing region and a tag region, and wherein individually, each of the target hybridizing regions of the at least two tagged amplification oligomers are selected from the group consisting of: a tagged amplification oligomer comprising a target hybridizing region that is from 15 to 50 nucleobases in length and contains a nucleotide sequence that is configured to hybridize to a region of a target nucleic acid corresponding to residues 5065 to 5088 of SEQ ID NO:1; a tagged amplification oligomer comprising a target hybridizing region that is from 15 to 50 nucleobases in length and contains a nucleotide sequence that is configured to hybridize to a region of a target nucleic acid corresponding to residues 4752 to 4798 of SEQ ID NO:2; a tagged amplification oligomer comprising a target hybridizing region that is from 15 to 50 nucleobases in length and contains a nucleotide sequence that is configured to hybridize to a region of a target nucleic acid corresponding to residues 1954 to 2006 of SEQ ID NO:3; and a tagged amplification oligomer comprising a target hybridizing region that is from 15 to 50 nucleobases in length and contains a nucleotide sequence that is configured to hybridize to a region of a target nucleic acid corresponding to residues 1994 to 2036 of SEQ ID NO:4, as are described above. In one aspect, said initial amplification product comprises a tag sequence that is from 10 to 25 nucleobases in length. In another aspect said initial amplification product comprises a tag sequence that is from 18 to 24 nucleobases in length. In another aspect, said initial amplification product comprises a tag sequence that is 19 nucleobases in length. In another aspect, said initial amplification product comprises a tag sequence that contains a sequence that is substantially complementary to one of SEQ ID NO:13, SEQ ID NO:16 and SEQ ID NO:33. In another aspect, said initial amplification product comprises a tag sequence that contains a sequence that is substantially identical to one of SEQ ID NO:13, SEQ ID NO:16 and SEQ ID NO:33. In another aspect, said initial amplification product comprises a tag sequence that contains a nucleotide sequence selected from the group consisting of: a sequence with at least 95% identity to SEQ ID NO:43 or complement thereof; a sequence with at least 95% identity to SEQ ID NO:44 or complement thereof; a sequence with 100% identity to SEQ ID NO:43 or complement thereof; and a sequence with 100% identity to SEQ ID NO:44 or complement thereof.

In one embodiment, there is an amplification reaction mixture for generating from an initial nucleic acid amplification product containing a tag sequence or complement thereof, as described above, a further nucleic acid amplification product, wherein said amplification reaction mixture comprises a tag-targeting amplification oligomer comprising a target hybridizing region containing a nucleic acid sequence configured to specifically hybridize to said tag sequence, or complement thereof, that contained within the nucleotide sequence of said initial nucleic acid amplification product, and wherein said amplification reaction mixture comprises a promoter-based amplification oligomer comprising a target hybridizing region that is 10 to 50 nucleobases in length and contains a nucleotide sequence that is configured to hybridize to all or a portion of a region of a target nucleic acid corresponding to residues 5016 to 5045 of SEQ ID NO:1. In one aspect, said target hybridizing region of said promoter-based amplification oligomer comprises a sequence that is at least 95% identical to SEQ ID NO:42. In another aspect, said target hybridizing region of said promoter-based amplification oligomer comprises a sequence that is 100% identical to SEQ ID NO:42. In another aspect, said promoter-based amplification oligomer comprising a sequence that is 100% identical to SEQ ID NO:15. In another aspect, said target hybridizing region of said tag-targeting amplification oligomer is 18 to 24 nucleobases in length. In another aspect, said tag-targeting amplification oligomer comprises a sequence that is at least 95% identical to a sequence selected from the group consisting of: SEQ ID NO:13, SEQ ID NO:16 and SEQ ID NO:33. In another aspect, said tag-targeting amplification oligomer comprises a sequence that is 100% identical to a sequence selected from the group consisting of: SEQ ID NO:13, SEQ ID NO:16 and SEQ ID NO:33.

In one embodiment, there is provided a method for the in vitro amplification of a nucleic acid in a sample, said nucleic acid being from one or more species in the class Mollicutes, comprising the steps of: (a.) contacting a sample with at least two tagged amplification oligomers, each of which individually comprises a target hybridizing region and a tag region, wherein said at least two tagged amplification oligomers are selected from the group consisting of: a tagged amplification oligomer comprising a target hybridizing region that is from 15 to 50 nucleobases in length and contains a nucleotide sequence that is configured to hybridize to a region of a target nucleic acid corresponding to residues 5065 to 5088 of SEQ ID NO:1; a tagged amplification oligomer comprising a target hybridizing region that is from 15 to 50 nucleobases in length and contains a nucleotide sequence that is configured to hybridize to a region of a target nucleic acid corresponding to residues 4752 to 4798 of SEQ ID NO:2; a tagged amplification oligomer comprising a target hybridizing region that is from 15 to 50 nucleobases in length and contains a nucleotide sequence that is configured to hybridize to a region of a target nucleic acid corresponding to residues 1954 to 2006 of SEQ ID NO:3; and a tagged amplification oligomer comprising a target hybridizing region that is from 15 to 50 nucleobases in length and contains a nucleotide sequence that is configured to hybridize to a region of a target nucleic acid corresponding to residues 1994 to 2036 of SEQ ID NO:4; and (b.) providing suitable conditions for performing an amplification reaction.

In one aspect, one of said at least two tagged amplification oligomers comprises a target hybridizing region that is from 20 to 24 nucleobases in length and contains a nucleotide sequence that is configured to hybridize to a region of a target nucleic acid corresponding to residues 5065 to 5088 of SEQ ID NO:1. In another aspect, said target-hybridizing region of said tagged amplification oligomer may contain one or more of a nucleotide addition, a nucleotide deletion, a nucleotide mismatch, a modified nucleotide or a combination thereof relative to a corresponding residue of said target nucleic acid. In another aspect, said target hybridizing region comprises at least 95% sequence identity to SEQ ID NO:38 or SEQ ID NO:39. In one aspect, said tag region of said tagged amplification oligomer is from 10 to 25 nucleobases in length. In another aspect, said tag region is from 18 to 24 nucleobases in length. In another aspect, said tag region is 19 nucleobases in length. In another aspect, said tag region contains a sequence that is substantially complementary to one of SEQ ID NO:13, SEQ ID NO:16 and SEQ ID NO:33. In another aspect, said tag region contains a sequence that is substantially identical to one of SEQ ID NO:13, SEQ ID NO:16 and SEQ ID NO:33. In another aspect, said tag region contains a nucleotide sequence selected from the group consisting of: a sequence with at least 95% identity to SEQ ID NO:43 or complement thereof; a sequence with at least 95% identity to SEQ ID NO:44 or complement thereof; a sequence with 100% identity to SEQ ID NO:43 or complement thereof; and a sequence with 100% identity to SEQ ID NO:44 or complement thereof. In one aspect, said tagged amplification oligomer further comprises a tag-closing region, said tag-closing region comprising a nucleotide sequence that is substantially complementary to a portion of said target hybridizing region of said tagged-amplification oligomer. In another aspect, said tag-closing region is 3 to 20 nucleobases in length.

In one aspect, said tagged amplification oligomer comprises at least 95% sequence identity to a sequence selected from the group consisting of SEQ ID NO:5, SEQ ID NO:17, SEQ ID NO:18, SEQ ID NO:30, SEQ ID NO:40 and SEQ ID NO:41. In another aspect, said tagged amplification oligomer comprises 100% sequence identity to SEQ ID NO:5. In another aspect, said tagged amplification oligomer comprises 100% sequence identity to SEQ ID NO:17. In another aspect, said tagged amplification oligomer comprises 100% sequence identity to SEQ ID NO:18. In another aspect, said tagged amplification oligomer comprises 100% sequence identity to SEQ ID NO:30.

In one aspect, one of said at least two tagged amplification oligomers comprises a target hybridizing region that is from 18 to 28 nucleobases in length and contains a nucleotide sequence that is configured to hybridize to a region of a target nucleic acid corresponding to residues 4752 to 4798 of SEQ ID NO:2. In another aspect, target-hybridizing region of said tagged amplification oligomer may contain one or more of a nucleotide addition, a nucleotide deletion, a nucleotide mismatch, a modified nucleotide or a combination thereof relative to a corresponding residue of said target nucleic acid. In another aspect, said target hybridizing region comprises at least 95% sequence identity to SEQ ID NO:45, SEQ ID NO:46, SEQ ID NO:47 or SEQ ID NO:48. In another aspect, said target hybridizing region is 15 to 30 nucleobases in length and contains a nucleotide sequence that is configured to hybridize to a region of a target nucleic acid corresponding to residues 4776 to 4798 of SEQ ID NO:2. In one aspect, said tag region of said tagged amplification oligomer is from 10 to 25 nucleobases in length. In another aspect, said tag region is from 18 to 24 nucleobases in length. In another aspect, said tag region is 19 nucleobases in length. In another aspect, said tag region contains a sequence that is substantially complementary to one of SEQ ID NO:13, SEQ ID NO:16 and SEQ ID NO:33. In another aspect, said tag region contains a sequence that is substantially identical to one of SEQ ID NO:13, SEQ ID NO:16 and SEQ ID NO:33. In another aspect, said tag region contains a nucleotide sequence selected from the group consisting of: a sequence with at least 95% identity to SEQ ID NO:43 or complement thereof; a sequence with at least 95% identity to SEQ ID NO:44 or complement thereof; a sequence with 100% identity to SEQ ID NO:43 or complement thereof; and a sequence with 100% identity to SEQ ID NO:44 or complement thereof. In one aspect, said tagged amplification oligomer further comprises a tag-closing region, said tag-closing region comprising a nucleotide sequence that is substantially complementary to a portion of said target hybridizing region of said tagged-amplification oligomer. In another aspect, said tag-closing region is 3 to 20 nucleobases in length.

In one aspect, said tagged amplification oligomer comprises at least 95% sequence identity to a sequence selected from the group consisting of SEQ ID NO:6, SEQ ID NO:23, SEQ ID NO:24 and SEQ ID NO:49. In another aspect, said tagged amplification oligomer comprises 100% sequence identity to SEQ ID NO:6. In another aspect, said tagged amplification oligomer comprises 100% sequence identity to SEQ ID NO:23. In another aspect, said tagged amplification oligomer comprises 100% sequence identity to SEQ ID NO:24.

In one aspect, one of said at least two tagged amplification oligomers comprises a target hybridizing region that is from 19 to 24 nucleobases in length and contains a nucleotide sequence that is configured to hybridize to a region of a target nucleic acid corresponding to residues 1954 to 2006 of SEQ ID NO:3. In another aspect, target-hybridizing region of said tagged amplification oligomer may contain one or more of a nucleotide addition, a nucleotide deletion, a nucleotide mismatch, a modified nucleotide or a combination thereof relative to a corresponding residue of said target nucleic acid. In another aspect, said target hybridizing region comprises at least 95% sequence identity to SEQ ID NO:50, SEQ ID NO:51, SEQ ID NO:52, SEQ ID NO:53, SEQ ID NO:54 or SEQ ID NO:55. In another aspect, said target hybridizing region is 15 to 30 nucleobases in length and contains a nucleotide sequence that is configured to hybridize to a region of a target nucleic acid corresponding to residues 1973 to 2006 of SEQ ID NO:3. In one aspect, said tag region of said tagged amplification oligomer is from 10 to 25 nucleobases in length. In another aspect, said tag region is from 18 to 24 nucleobases in length. In another aspect, said tag region is 19 nucleobases in length. In another aspect, said tag region contains a sequence that is substantially complementary to one of SEQ ID NO:13, SEQ ID NO:16 and SEQ ID NO:33. In another aspect, said tag region contains a sequence that is substantially identical to one of SEQ ID NO:13, SEQ ID NO:16 and SEQ ID NO:33. In another aspect, said tag region contains a nucleotide sequence selected from the group consisting of: a sequence with at least 95% identity to SEQ ID NO:43 or complement thereof; a sequence with at least 95% identity to SEQ ID NO:44 or complement thereof; a sequence with 100% identity to SEQ ID NO:43 or complement thereof; and a sequence with 100% identity to SEQ ID NO:44 or complement thereof. In one aspect, said tagged amplification oligomer further comprises a tag-closing region, said tag-closing region comprising a nucleotide sequence that is substantially complementary to a portion of said target hybridizing region of said tagged-amplification oligomer. In another aspect, said tag-closing region is 3 to 20 nucleobases in length.

In one aspect, said tagged amplification oligomer comprises at least 95% sequence identity to SEQ ID NO:7, SEQ ID NO:31, SEQ ID NO:56 or SEQ ID NO:57. In another aspect, said tagged amplification oligomer comprises 100% sequence identity to SEQ ID NO:7. In another aspect, said tagged amplification oligomer comprises 100% sequence identity to SEQ ID NO:31.

In one aspect, one of said at least two tagged amplification oligomers comprises a target hybridizing region that is from 20 to 25 nucleobases in length and contains a nucleotide sequence that is configured to hybridize to a region of a target nucleic acid corresponding to residues 1994 to 2036 of SEQ ID NO:4. In another aspect, target-hybridizing region of said tagged amplification oligomer may contain one or more of a nucleotide addition, a nucleotide deletion, a nucleotide mismatch, a modified nucleotide or a combination thereof relative to a corresponding residue of said target nucleic acid. In another aspect, said target hybridizing region comprises at least 95% sequence identity to SEQ ID NO:58, SEQ ID NO:59, SEQ ID NO:60, SEQ ID NO:61 or SEQ ID NO:62. In another aspect, said target hybridizing region is 15 to 30 nucleobases in length and contains a nucleotide sequence that is configured to hybridize to a region of a target nucleic acid corresponding to residues 1994 to 2017 of SEQ ID NO:4. In one aspect, said tag region of said tagged amplification oligomer is from 10 to 25 nucleobases in length. In another aspect, said tag region is from 18 to 24 nucleobases in length. In another aspect, said tag region is 19 nucleobases in length. In another aspect, said tag region contains a sequence that is substantially complementary to one of SEQ ID NO:13, SEQ ID NO:16 and SEQ ID NO:33. In another aspect, said tag region contains a sequence that is substantially identical to one of SEQ ID NO:13, SEQ ID NO:16 and SEQ ID NO:33. In another aspect, said tag region contains a nucleotide sequence selected from the group consisting of: a sequence with at least 95% identity to SEQ ID NO:43 or complement thereof; a sequence with at least 95% identity to SEQ ID NO:44 or complement thereof; a sequence with 100% identity to SEQ ID NO:43 or complement thereof; and a sequence with 100% identity to SEQ ID NO:44 or complement thereof. In one aspect, said tagged amplification oligomer further comprises a tag-closing region, said tag-closing region comprising a nucleotide sequence that is substantially complementary to a portion of said target hybridizing region of said tagged-amplification oligomer. In another aspect, said tag-closing region is 3 to 20 nucleobases in length. In one aspect, said tagged amplification oligomer comprises at least 95% sequence identity to SEQ ID NO:8, or SEQ ID NO:63. In another aspect, said tagged amplification oligomer comprises 100% sequence identity to SEQ ID NO:8.

In one aspect, said at least two tagged amplification oligomers comprises SEQ ID NO:5 and a second tagged amplification oligomer selected from the group consisting of: a tagged amplification oligomer with a sequence that is at least 95% identical to SEQ ID NO:6, a tagged amplification oligomer with a sequence that is at least 95% identical to SEQ ID NO:7, a tagged amplification oligomer with a sequence that is at least 95% identical to SEQ ID NO:8, a tagged amplification oligomer with a sequence that is 100% identical to SEQ ID NO:6, a tagged amplification oligomer with a sequence that is 100% identical to SEQ ID NO:7 and a tagged amplification oligomer with a sequence that is 100% identical to SEQ ID NO:8. In another aspect, said at least two tagged amplification oligomers comprises SEQ ID NO:6 and a second tagged amplification oligomer selected from the group consisting of: a tagged amplification oligomer that is at least 95% identical to SEQ ID NO:5, a tagged amplification oligomer that is at least 95% identical to SEQ ID NO:7, a tagged amplification oligomer that is at least 95% identical to SEQ ID NO:8, a tagged amplification oligomer that is 100% identical to SEQ ID NO:5, a tagged amplification oligomer that is 100% identical to SEQ ID NO:7 and a tagged amplification oligomer that is 100% identical to SEQ ID NO:8. In another aspect, said at least two tagged amplification oligomers comprises SEQ ID NO:7 and a second tagged amplification oligomer selected from the group consisting of: a tagged amplification oligomer that is at least 95% identical to SEQ ID NO:5, a tagged amplification oligomer that is at least 95% identical to SEQ ID NO:6, a tagged amplification oligomer that is at least 95% identical to SEQ ID NO:8, a tagged amplification oligomer that is 100% identical to SEQ ID NO:5, a tagged amplification oligomer that is 100% identical to SEQ ID NO:6 and a tagged amplification oligomer that is 100% identical to SEQ ID NO:8. In another aspect, said at least two tagged amplification oligomers comprises SEQ ID NO:8 and a second tagged amplification oligomer selected from the group consisting of: a tagged amplification oligomer that is at least 95% identical to SEQ ID NO:5, a tagged amplification oligomer that is at least 95% identical to SEQ ID NO:6, a tagged amplification oligomer that is at least 95% identical to SEQ ID NO:7, a tagged amplification oligomer that is 100% identical to SEQ ID NO:5, a tagged amplification oligomer that is 100% identical to SEQ ID NO:6 and a tagged amplification oligomer that is 100% identical to SEQ ID NO:7. In another aspect, said at least two tagged amplification oligomers comprises four tagged amplification oligomers selected from the group consisting of: a tagged amplification oligomer that is at least 95% identical to SEQ ID NO:5, a tagged amplification oligomer that is 100% identical to SEQ ID NO:5, a tagged amplification oligomer that is at least 95% identical to SEQ ID NO:6, a tagged amplification oligomer that is 100% identical to SEQ ID NO:6, a tagged amplification oligomer that is at least 95% identical to SEQ ID NO:7, a tagged amplification oligomer that is 100% identical to SEQ ID NO:7, a tagged amplification oligomer that is at least 95% identical to SEQ ID NO:8, and a tagged amplification oligomer that is 100% identical to SEQ ID NO:8.

In one aspect, said at least two tagged amplification oligomers comprises SEQ ID NO:5 and a second tagged amplification oligomer with a sequence that is at least 95% identical to SEQ ID NO:6, SEQ ID NO:7, or SEQ ID NO:8, or that is 100% identical to SEQ ID NO:6, SEQ ID NO:7 or SEQ ID NO:8. In another aspect, said at least two tagged amplification oligomers comprises SEQ ID NO:6 and a second tagged amplification oligomer that is at least 95% identical to SEQ ID NO:5, SEQ ID NO:7, or SEQ ID NO:8, or that is 100% identical to SEQ ID NO:5, SEQ ID NO:7 or SEQ ID NO:8. In another aspect, said at least two tagged amplification oligomers comprises SEQ ID NO:7 and a second tagged amplification oligomer that is at least 95% identical to SEQ ID NO:5, SEQ ID NO:6, or SEQ ID NO:8, or that is 100% identical to SEQ ID NO:5, SEQ ID NO:6 or SEQ ID NO:8. In another aspect, said at least two tagged amplification oligomers comprises SEQ ID NO:8 and a second tagged amplification oligomer that is at least 95% identical to SEQ ID NO:5, SEQ ID NO:6, or SEQ ID NO:7, or that is 100% identical to SEQ ID NO:5, SEQ ID NO:6 or SEQ ID NO:7. In another aspect, said at least two tagged amplification oligomers comprises three tagged amplification oligomers each of the three individually being a tagged amplification oligomer that is at least 95% identical to SEQ ID NO:5, SEQ ID NO:6, SEQ ID NO:7, or SEQ ID NO:8, or that is 100% identical to SEQ ID NO:5, SEQ ID NO:6, SEQ ID NO:7 or SEQ ID NO:8. In another aspect, said at least two tagged amplification oligomers comprises four tagged amplification oligomers each of the four individually being a tagged amplification oligomer that is at least 95% identical to SEQ ID NO:5, SEQ ID NO:6, SEQ ID NO:7, or SEQ ID NO:8, or that is 100% identical to SEQ ID NO:5, SEQ ID NO:6, SEQ ID NO:7 or SEQ ID NO:8.

In one embodiment, said composition further comprises at least one blocker oligomer. In one aspect, one of said at least one blocker oligomer is at least 95% identical to SEQ ID NO:9 or SEQ ID NO:10. In another aspect, one of said at least one blocker oligomer is at least 95% identical to SEQ ID NO:9 or SEQ ID NO:10. In another aspect, said at least one blocker oligomer is two blocker oligomers, one of which is at least 95% identical to SEQ ID NO:9; or one of which is at least 95% identical to SEQ ID NO:10; or one of which is at least 95% identical to SEQ ID NO:9 and another of which is at least 95% identical to SEQ ID NO:10; or one of which is 100% identical to SEQ ID NO:9; or one of which is 100% identical to SEQ ID NO:10; or one of which is at least 95% identical to SEQ ID NO:9 and another of which is 100% identical to SEQ ID NO:10; or one of which is 100% identical to SEQ ID NO:9 and another of which is at least 95% identical to SEQ ID NO:10; or one of which is 100% identical to SEQ ID NO:9 and another of which is 100% identical to SEQ ID NO:10.

In one aspect, said method at step (b.) results in at least one initial amplification product containing a tag sequence, or complement thereof. In another aspect, there is provided at least initial amplification product with a nucleotide sequence comprising a tag sequence region, wherein said tag sequence is from 10 to 25 nucleobases in length. In another aspect said initial amplification product comprises a tag sequence that is from 18 to 24 nucleobases in length. In another aspect, said initial amplification product comprises a tag sequence that is 19 nucleobases in length. In another aspect, said initial amplification product comprises a tag sequence that contains a sequence that is substantially complementary to one of SEQ ID NO:13, SEQ ID NO:16 and SEQ ID NO:33, or is substantially identical to one of SEQ ID NO:13, SEQ ID NO:16 and SEQ ID NO:33. In another aspect, said initial amplification product comprises a tag sequence that contains a nucleotide sequence selected from the group consisting of: a sequence with at least 95% identity to SEQ ID NO:43 or complement thereof; a sequence with at least 95% identity to SEQ ID NO:44 or complement thereof; a sequence with 100% identity to SEQ ID NO:43 or complement thereof; and a sequence with 100% identity to SEQ ID NO:44 or complement thereof. In one aspect, said initial amplification product has a 3' end defined by a blocker oligomer. In another aspect, said initial amplification product has a 3' end that is not defined by a blocker oligomer.

In one embodiment of the current invention, there is provided a method for the in vitro amplification of an initial amplification product, comprising the steps of (c.) contacting the sample with at least one additional amplification oligomer selected from the group consisting of a tag-targeting amplification oligomer, a primer oligomer and a promoter-based amplification oligomer; and (d.) providing suitable conditions for performing a second amplification reaction. In one aspect, the oligomers of step (c.) and the oligomers of step (a.) are contacted to said sample at the same time point. In one aspect, the oligomers of step (c.) and the oligomers of step (a.) are contacted to the sample and a single amplification reaction is performed. In this aspect, steps (b.) and (d.) are combined to provide suitable conditions for performing an amplification reaction to generate an initial amplification product and for performing an amplification reaction generate a second amplification product therefrom. Though all of the amplification oligomers are present in this combined amplification reaction aspect, the tag-targeting amplification oligomers are configured to not participate in amplification until a tagged amplification oligomer is incorporated into an initial amplification product. In another aspect, the oligomers of step (c.) and the oligomers of step (a.) are contacted to said sample at separate time points. In one aspect, the method comprises the step of (c.) providing to an amplification product generated in step (b.) a second reaction mixture comprising a tag-targeting amplification oligomer consisting essentially of a target hybridizing region that contains a nucleotide sequence configured to specifically hybridize to a tag region of said tagged amplification oligomer, and comprising a second amplification oligomer; and (d.) providing suitable conditions for performing a second amplification reaction. In one aspect for generating an amplification product, said sample is contacted with a first additional amplification oligomer that is a tag-targeting amplification oligomer comprising a target hybridizing region that contains a nucleotide sequence configured to specifically hybridize to a tag region of said, or complement thereof in an initial amplification oligomer, and is contacted with a second additional amplification oligomer. In another aspect, said tag-targeting amplification oligomer comprises a target hybridization region that is 18 to 24 nucleobases in length. In another aspect, said tag-targeting amplification oligomer comprises a sequence that is at least 95% identical to a sequence selected from the group consisting of SEQ ID NO:13, SEQ ID NO:16 and SEQ ID NO:33. In another aspect, said tag-targeting amplification oligomer comprises a sequence that is 100% identical to SEQ ID NO:13. In another aspect, said tag-targeting amplification oligomer comprises a sequence that is 100% identical to SEQ ID NO:16. In another aspect, said tag-targeting amplification oligomer comprises a sequence that is 100% identical to SEQ ID NO:33. In one aspect, said second amplification oligomer is a primer amplification oligomer, a promoter based amplification oligomer or a tagged amplification oligomer. In another aspect, said second amplification oligomer is a promoter-based amplification oligomer comprising a target hybridizing region that is 10 to 50 nucleobases in length and contains a nucleotide sequence that is configured to hybridize to all or a portion of a region of a target nucleic acid corresponding to residues 5016 to 5045 SEQ ID NO:1. In another aspect, said promoter-based amplification oligomer comprises a target hybridizing region that is at least 95% identical to SEQ ID NO:42 or that is 100% identical to SEQ ID NO:42. In another aspect, said a promoter-based amplification is at least 95% identical to SEQ ID NO:15 or is 100% identical to SEQ ID NO:15.

In one embodiment there is further provided an analysis step, wherein an initial amplification product, an amplification product or both are analyzed. In one aspect, said analysis comprises a detection step to identify the presence or absence of an initial amplification product from an amplification reaction in step (b.), an amplification product generated in step (d.) or both initial amplification and amplification products generated in steps (b.) and (d.). In another aspect, said detection step is a probe-based detection step. In another aspect, said probe-based detection step uses a probe with a nucleotide sequence that is at least 95% identical to SEQ ID NO:14. In another aspect, said detection step is a probe-based detection step. In another aspect, said probe-based detection step uses a probe with a nucleotide sequence that is 100% identical to SEQ ID NO:14.

In one embodiment, there is provided compositions, reaction mixtures and methods comprising at least one target capture oligomer. In one aspect, the target capture oligomers are also blocker oligomers. Preferred target capture oligomers include, but are not limited to SEQ ID NO:11, SEQ ID NO:12, SEQ ID NO:28, SEQ ID NO:29, SEQ ID NO:64, SEQ ID NO:65 and combinations thereof.

DETAILED DESCRIPTION

Disclosed are compositions, reaction mixtures, kits and methods for amplifying Mollicutes nucleic acids from a sample; specifically sequences of a 23S rRNA or genes encoding a 23S rRNA. Amplified nucleic acids are then useful for a subsequent analysis. The compositions, reaction mixtures, kits and methods provide oligonucleotide sequences that recognize target sequences of 23S rRNA or their complementary sequences, or genes encoding 23S rRNA or their complementary sequences from a variety of species of Mollicutes. Such oligonucleotides include tagged amplification oligomers, blocker oligomers, tag-targeting amplification oligomers and promoter-based amplification oligomers; and in some embodiments further include target capture oligomers and detection probe oligomers. Reaction mixtures include target capture reagents, lysis reagents and amplification reagents. All or some of the oligomer compositions may be present in one or more of such reaction mixtures.

The methods include performing a nucleic acid amplification of Mollicutes sequences. Amplified nucleic acids are then useful for a variety of subsequent analysis methods, including, but not limited to nucleic acid detection, for example by specifically hybridizing the amplified product with a nucleic acid probe that provides a signal to indicate the presence of a Mollicutes in the sample. The amplification step includes contacting the sample with one or more amplification oligomers specific for a target sequence in 23S rRNA to produce an amplified product if a Mollicutes nucleic acid is present in the sample. Amplification synthesizes additional copies of the target sequence or its complement by using at least one nucleic acid polymerase to extend the sequence from an amplification oligomer (a primer) using a template strand. One embodiment for detecting the amplified product uses a hybridizing step that includes contacting the amplified product with at least one probe specific for a sequence amplified by the selected amplification oligomers, e.g., a sequence contained in the target sequence flanked by a pair of selected primers.

"Amplification" refers to any known procedure for obtaining multiple copies of a target nucleic acid sequence or its complement or fragments thereof. The multiple copies may be referred to as amplicons or amplification products. Amplification of "fragments" refers to production of an amplified nucleic acid that contains less than the complete target nucleic acid or its complement, e.g., produced by using an amplification oligonucleotide that hybridizes to, and initiates polymerization from, an internal position of the target nucleic acid. Known amplification methods include, for example, replicase-mediated amplification, polymerase chain reaction (PCR), ligase chain reaction (LCR), strand-displacement amplification (SDA), and transcription-mediated or transcription-associated amplification. Replicase-mediated amplification uses self-replicating RNA molecules, and a replicase such as QB-replicase (e.g., U.S. Pat. No. 4,786,600). PCR amplification uses a DNA polymerase, pairs of primers, and thermal cycling to synthesize multiple copies of two complementary strands of dsDNA or from a cDNA (e.g., U.S. Pat. Nos. 4,683,195, 4,683,202, and 4,800,159). LCR amplification uses four or more different oligonucleotides to amplify a target and its complementary strand by using multiple cycles of hybridization, ligation, and denaturation (e.g., U.S. Pat. Nos. 5,427,930 and 5,516,663). SDA uses a primer that contains a recognition site for a restriction endonuclease and an endonuclease that nicks one strand of a hemimodified DNA duplex that includes the target sequence, whereby amplification occurs in a series of primer extension and strand displacement steps (e.g., U.S. Pat. Nos. 5,422,252; 5,547,861; and 5,648,211). Those skilled in the art will know how to provide suitable conditions for performing these amplification reactions.

In the examples below, the nucleic acid of one or more species of the class Mollicutes is amplified by a transcription-based amplification technique. One transcription-based amplification system is transcription-mediated amplification (TMA), which employs an RNA polymerase to produce multiple RNA transcripts of a target region. Exemplary TMA amplification methods are described in U.S. Pat. Nos. 4,868,105; 5,124,246; 5,130,238; 5,399,491; 5,437,990; 5,480,784; 5,554,516; and 7,374,885; and PCT Pub. Nos. WO 88/01302; WO 88/10315 and WO 95/03430. The TMA reaction used below is a single primer TMA reaction as is described in U.S. Pat. No. 7,374,885. In general, the single-primer TMA methods use a primer oligomer, a modified promoter-based oligomer (or "promoter-provider oligomer") that is modified to prevent the initiation of DNA synthesis from its 3' end (e.g., by including a 3'-blocking moiety) and, optionally, a blocker oligomer to terminate elongation of a cDNA from the target strand. Promoter-based oligomers provide an oligonucleotide sequence that is recognized by an RNA polymerase. This single primer TMA method synthesizes multiple copies of a target sequence and includes the steps of treating a target RNA that contains a target sequence with a priming oligomer and a binding molecule, where the primer hybridizes to the 3' end of the target strand. RT initiates primer extension from the 3' end of the primer to produce a cDNA which is in a duplex with the target strand (e.g., RNA:cDNA). When a blocker oligomer, is used in the reaction, it binds to the target nucleic acid adjacent near the user designated 5' end of the target sequence. When the primer is extended by DNA polymerase activity of RT to produce cDNA, the 3' end of the cDNA is determined by the position of the blocker oligomer because polymerization stops when the primer extension product reaches the binding molecule bound to the target strand. Thus, the 3' end of the cDNA is complementary to the 5' end of the target sequence. The RNA:cDNA duplex is separated when RNase (e.g., RNase H of RT) degrades the RNA strand, although those skilled in the art will appreciate that any form of strand separation may be used. Then, the promoter-provider oligomer hybridizes to the cDNA near the 3' end of the cDNA strand. The promoter-provider oligomer includes a 5' promoter sequence for an RNA polymerase and a 3' target hybridizing region complementary to a sequence in the 3' region of the cDNA. The promoter-provider oligomer also has a modified 3' end that includes a blocking moiety that prevents initiation of DNA synthesis from the 3' end of the promoter-provider oligomer. In the promoter-provider:cDNA duplex, the 3'-end of the cDNA is extended by DNA polymerase activity of RT using the promoter oligomer as a template to add a promoter sequence to the cDNA and create a functional double-stranded promoter. An RNA polymerase specific for the promoter sequence then binds to the functional promoter and transcribes multiple RNA transcripts complementary to the cDNA and substantially identical to the target region sequence that was amplified from the initial target strand. The resulting amplified RNA can then cycle through the process again by binding the primer and serving as a template for further cDNA production, ultimately producing many amplicons from the initial target nucleic acid present in the sample. Some embodiments of the single-primer transcription-associated amplification method do not include the blocking oligomer and, therefore, the cDNA product made from the primer has an indeterminate 3' end, but the amplification steps proceed substantially as described above for all other steps.

The current invention provides compositions and methods for uniplex and multiplex amplification reactions. Assays for the nucleic acid amplification of Mollicutes nucleic acid in a sample source oftentimes show false positive or false negative results caused by contaminating from the environment and non-specific binding. Partly, these problems arise because of contaminating organisms present in the assay reagents or carried by the operators. For example, when the sample source is a bioreactor and the assay is to amplify Mollicutes common to such a source, then *M. orale M. salivarium M. pneumoniae* carried in by the assay operator can contaminate the assay. Partly too, laboratory environments where assays are performed and laboratory reagents can carry contaminating organisms that will non-specifically bind the assay reagents, leading to inefficient amplification of the target or amplification of non-target. False positives and false negatives are thus a significant challenge. Further challenging these assays when performed in multiplex are the deficiencies common to multiplex reactions, e.g., spurious product formation, primer dimers, unbalanced amplification caused by more efficient amplifications outperforming the less efficient reactions and thereby suing the reagents. Herein, the amplification oligomers comprise at least one tag region to address these and other problems.

Below describes an adaptation of a reverse transcription-mediated amplification (rTMA), various aspects of which are disclosed in U.S. Pat. Appln. Pub. No. US 2006-0046265 A1. The reaction of this illustrative embodiment is initiated by treating an RNA target sequence in a nucleic acid sample with both a tagged amplification oligomer and, optionally a blocking oligomer. The tagged amplification oligomer includes a target hybridizing region that hybridizes to a 3'-end of the target sequence and a tag region situated 5' to the target hybridizing region. The blocking oligomer hybridizes to a target nucleic acid containing the target sequence in the vicinity of the 5'-end of the target sequence. Thus, the target nucleic acid forms a stable complex with the tagged amplification oligomer at the 3'-end of the target sequence and the terminating oligonucleotide located adjacent to or near the determined 5'-end of the target sequence prior to initiating a primer extension reaction. Unhybridized tagged amplification oligomers are then made unavailable for hybridization to a target sequence prior to initiating a primer extension reaction with the tagged priming oligonucleotide, preferably by inactivating and/or removing the unhybridized tagged priming oligonucleotide from the nucleic acid sample. Unhybridized tagged amplification oligomer that has been inactivated or removed from the system is then unavailable for unwanted hybridization to contaminating nucleic acids. In one example of removing unhybridized tagged amplification oligomer from a reaction mixture, the tagged amplification oligomer is hybridized to the target nucleic acid, and the tagged amplification oligomer:target nucleic acid complex is removed from the unhybridized tagged amplification oligomer using a wash step. In this example, the tagged amplification oligomer:target nucleic acid complex may be further complexed to a target capture oligomer and a solid support. In one example of inactivating the unhybridized tagged amplification oligomer, the tagged amplification oligomers further comprise a target-closing region. In this example, the target hybridizing region of the tagged amplification oligomer hybridizes to target nucleic acid under a first set of conditions (e.g., stringency). Following the formation of the tagged amplification oligomer: target nucleic acid complex the unhybridized tagged amplification oligomer is inactivated under a second set of the conditions, thereby hybridizing the target closing region to the target hybridizing region of the unhybridized tagged amplification oligomer. The inactivated tagged amplification oligomer is then unavailable for hybridizing contaminating nucleic acids. A wash step may also be included to remove the inactivated tagged amplification oligomers from the assay.

An extension reaction is then initiated from the 3'-end of the tagged amplification oligomer with a DNA polymerase, e.g., reverse transcriptase, to produce an initial amplification product that includes the tag sequence. The initial amplification product is then separated from the target sequence using an enzyme that selectively degrades the target sequence (e.g., RNAse H activity). Next, the initial amplification product is treated with a promoter-based oligomer having a target hybridizing region and an RNA polymerase promoter region situated 5' to the target hybridizing region, thereby forming a promoter-based oligomer:initial amplification product hybrid. In the examples below the promoter-based oligomer is modified to prevent the initiation of DNA synthesis, preferably by situating a blocking moiety at the 3'-end of the promoter-based oligomer (e.g., nucleotide sequence having a 3'-to-5' orientation). The 3'-end of the initial amplification product is then extended to add a sequence complementary to the promoter, resulting in the formation of a double-stranded promoter sequence. Multiple copies of a RNA product complementary to at least a portion of the initial amplification product are then transcribed using an RNA polymerase, which recognizes the double-stranded promoter and initiates transcription therefrom. As a result, the nucleotide sequence of the RNA product is substantially identical to the nucleotide sequence of the target nucleic acid and to the complement of the nucleotide sequence of the tag sequence.

The RNA products are then treated with a tag-targeting oligomer, which hybridizes to the complement of the tag sequence to form a tag-targeting oligomer: RNA product hybrid, and the 3'-end of the tag-targeting oligomer is extended with the DNA polymerase to produce an amplification product complementary to the RNA product. The DNA strand of this amplification product is then separated from the RNA strand of this amplification product using an enzyme that selectively degrades the first RNA product (e.g., RNAse H activity). The DNA strand of the amplification product is treated with the promoter-based oligomer, which hybridizes to the 3'-end of the second DNA primer extension product to form a promoter-based oligomer:amplification product hybrid. The promoter-based oligomer:amplification product hybrid then re-enters the amplification cycle, where transcription is initiated from the double-stranded promoter and the cycle continues, thereby providing amplification product of the target sequence.

Amplification product can then be used in a subsequent assay. One subsequent assay includes nucleic acid detection, preferably nucleic acid probe-based nucleic acid detection. The detection step may be performed using any of a variety of known ways to detect a signal specifically associated with the amplified target sequence, such as by hybridizing the amplification product with a labeled probe and detecting a signal resulting from the labeled probe. The detection step may also provide additional information on the amplified sequence, such as all or a portion of its nucleic acid base sequence. Detection may be performed after the amplification reaction is completed, or may be performed simultaneous with amplifying the target region, e.g., in real time. In one embodiment, the detection step allows homogeneous detection, e.g., detection of the hybridized probe without removal of unhybridized probe from the mixture (e.g., U.S. Pat. Nos. 5,639,604 and 5,283,174). In embodiments that detect the amplified product near or at the end of the amplification step, a linear probe may be used to provide a signal to indicate hybridization of the probe to the amplified product. One example of such detection uses a luminescentally labeled probe that hybridizes to target nucleic acid.

Luminescent label is then hydrolyzed from non-hybridized probe. Detection is performed by chemiluminescence using a luminometer. (e.g., WO 89/002476). In other embodiments that use real-time detection, the probe may be a hairpin probe, such as a molecular beacon, molecular torch, or hybridization switch probe, that is labeled with a reporter moiety that is detected when the probe binds to amplified product. Such probes may comprise target binding sequences and non-target binding sequences. Various forms of such probes have been described previously (e.g., U.S. Pat. Nos. 5,118,801; 5,312,728; 5,925,517; 6,150,097; 6,849,412; 6,835,542; 6,534,274; and 6,361,945; and US Pub. Nos. 20060068417A1; and US Pub. No. 20060194240A1).

To aid in understanding aspects of the invention, some terms used herein are described in more detail. All other scientific and technical terms used herein have the same meaning as commonly understood by those skilled in the relevant art, such as may be provided in *Dictionary of Microbiology and Molecular Biology*, 2nd ed. (Singleton et al., 1994, John Wiley & Sons, New York, N.Y.), *The Harper Collins Dictionary of Biology* (Hale & Marham, 1991, Harper Perennial, New York, N.Y.), and other references cited herein. Unless mentioned otherwise, the techniques employed or contemplated herein are standard methods well known to a person of ordinary skill in the art of molecular biology.

It is to be noted that the term "a" or "an" entity refers to one or more of that entity; for example, "a nucleic acid," is understood to represent one or more nucleic acids. As such, the terms "a" (or "an"), "one or more," and "at least one" can be used interchangeably herein.

"Sample" includes those that may contain one or more species from the class Mollicutes or components thereof, such as nucleic acids or fragments of nucleic acids wherein the source of that sample may contain an undesired species of Mollicutes. Samples include bioreactors; mammalian, avian, insect, fish or plant cell lines; laboratory workspaces, laboratory equipment, cell-culture wares, laboratory reagents, biological manufacturing wares, pharmaceutical manufacturing wares, biological drug product, biological bulk drug substance, pharmaceutical drug product, pharmaceutical bulk drug substance and biological samples.

"Nucleic acid" refers to a multimeric compound comprising two or more covalently bonded nucleosides or nucleoside analogs having nitrogenous heterocyclic bases, or base analogs, where the nucleosides are linked together by phosphodiester bonds or other linkages to form a polynucleotide. A "nucleotide" as used herein is a subunit of a nucleic acid consisting of a phosphate group, a 5-carbon sugar and a nitrogenous base. The 5-carbon sugar found in RNA is ribose. In DNA, the 5-carbon sugar is 2'-deoxyribose. The term also includes analogs of such subunits, such as a methoxy group at the 2' position of the ribose (2'-O-Me). As used herein, methoxy oligonucleotides containing "T" residues have a methoxy group at the 2' position of the ribose moiety, and a uracil at the base position of the nucleotide. A "non-nucleotide unit" as used herein is a unit that does not significantly participate in hybridization of a polymer. Such units must not, for example, participate in any significant hydrogen bonding with a nucleotide, and would exclude units having as a component one of the five nucleotide bases or analogs thereof.

The term "polynucleotide" as used herein denotes a nucleic acid chain. Throughout this application, nucleic acids are designated by the 5'-terminus to the 3'-terminus. Standard nucleic acids, e.g., DNA and RNA, are typically synthesized "3'-to-5'," i.e., by the addition of nucleotides to the 5'-terminus of a growing nucleic acid.

A "target nucleic acid" as used herein is a nucleic acid comprising a "target sequence" to be amplified. Target nucleic acids may be DNA or RNA as described herein, and may be either single-stranded or double-stranded. The target nucleic acid may include other sequences besides the target sequence, which may not be amplified. The preferred target nucleic acid herein is a nucleic acid from one or more species of the class Mollicutes.

By "isolated" it is meant that a sample containing a target nucleic acid is taken from its natural milieu, but the term does not connote any degree of purification. "Separating" or "purifying" means that one or more components of a sample are removed or separated from other sample components. Sample components include target nucleic acids usually in a generally aqueous solution phase, which may also include cellular fragments, proteins, carbohydrates, lipids, and other nucleic acids. Separating or purifying removes at least 70%, of the target nucleic acid from other sample components.

The term "target sequence" as used herein refers to the particular nucleotide sequence of the target nucleic acid that is to be amplified and/or detected. The "target sequence" includes the sequences to which oligomers hybridize (e.g., tagged amplification oligomer, tag-target oligomers, promoter-based amplification oligomers, blocking oligomers, target-capture oligomers, detection oligomers). Where the target nucleic acid is originally single-stranded, the term "target sequence" will also refer to the sequence complementary to the "target sequence" as present in the target nucleic acid. Where the target nucleic acid is originally double-stranded, the term "target sequence" refers to both the sense (+) and antisense (−) strands. In choosing a target sequence, the skilled artisan will understand that a "unique" sequence should be chosen so as to distinguish between unrelated or closely related target nucleic acids.

"Target binding region" is used herein to refer to the portion of an oligomer that is configured to hybridize with a target nucleic acid sequence. Preferably, the target binding regions are configured to specifically hybridize with a target nucleic acid sequence. Target binding regions may be 100% complementary to the portion of the target sequence to which they are hybridize; but not necessarily. Target-binding regions may also include inserted, deleted and/or substituted nucleotide residues relative to a target sequence. Less than 100% complementarity of a target binding region to a target sequence may arise, for example, when the target nucleic acid is a plurality of strains within a species or within a class, such as would be the case for an oligomer that hybridizes to a variety of the strains of Mollicutes class. It is understood that other reasons exist for configuring a target binding region to have less than 100% complementarity to a target nucleic acid. Target hybridizing regions are preferably about 10 to 50 nucleotides in length. In the current description, for some of the oligomers, the target hybridizing regions are described as being configured to hybridize to a region of a reference sequence. This type of description is not a limitation that an oligomer comprising such a target hybridizing region is one that is limited to hybridizing only to that reference sequence. Similarly, this description does not exclude target hybridizing regions that hybridize to the complementary strand of that illustrated by the reference sequence.

The term "targets a sequence" as used herein in reference to a region of a Mollicutes nucleic acid refers to a process whereby an oligonucleotide hybridizes to the target sequence in a manner that allows for amplification as described herein. Preferably, the oligomer specifically hybridizes to the target sequence or group of target sequences.

The term "fragment" as used herein in reference to the Mollicutes targeted nucleic acid sequence refers to a piece of contiguous nucleic acid. In certain embodiments, the fragment includes contiguous nucleotides from a Mollicutes 23S ribosomal RNA, wherein the number of 23S contiguous nucleotides in the fragment are less than that for the entire 23S.

The term "region" as used herein refers to a portion of a nucleic acid wherein said portion is smaller than the entire nucleic acid. In one example the nucleic acid in reference is an amplification oligomer, such as a tagged-amplification oligomer. Here, the term "region" may be used refer to the smaller target hybridizing-portion of the entire oligomer or the tag portion of the entire oligomer. Similarly, and also as example only, when the nucleic acid is a 23S ribosomal RNA, the term "region" may be used to refer to a smaller area of the nucleic acid, wherein the smaller area is targeted by one or more oligonucleotides of the invention. As a further non-limiting example, when the nucleic acid in reference is an initial amplification product, the term region may be used to refer to the smaller tag nucleotide sequence or complementary tag nucleotide sequence identified for hybridization by the target binding region of a tagged-amplification oligomer.

The interchangeable terms "oligomer," "oligo" and "oligonucleotide" refer to a nucleic acid having generally less than 1,000 nucleotide (nt) residues, including polymers in a range having a lower limit of about 5 nt residues and an upper limit of about 500 to 900 nt residues. In some embodiments, oligonucleotides are in a size range having a lower limit of about 10 to 15 nt and an upper limit of about 50 to 600 nt, and other embodiments are in a range having a lower limit of about 15 to 20 nt and an upper limit of about 22 to 100 nt. These ranges are merely exemplary. Oligonucleotides may be purified from naturally occurring sources, or may be synthesized using any of a variety of well known enzymatic or chemical methods. The term oligonucleotide does not denote any particular function to the reagent; rather, it is used generically to cover all such reagents described herein. An oligonucleotide may serve various different functions. Herein, the oligomers referred to are primarily amplification oligomers such as primer oligomers, promoter-based amplification oligomers, tagged amplification oligomers, tag-targeting oligomers; target capture oligomers, detection oligomers and blocker oligomers. This list of oligomers is non-limiting, as is understood by the skilled artisan.

As used herein, an oligonucleotide having a nucleic acid sequence "comprising" or "consisting of" or "consisting essentially of" a sequence selected from a group of specific sequences means that the oligonucleotide, as a basic and novel characteristic, is capable of stably hybridizing to a nucleic acid having the exact complement of one of the listed nucleic acid sequences of the group under stringent hybridization conditions. An exact complement includes the corresponding DNA or RNA sequence.

"Consisting essentially of" is used to mean that additional component(s), composition(s) or method step(s) that do not materially change the basic and novel characteristics of the present invention may be included in the compositions or kits or methods of the present invention. Such characteristics include the ability to detect Mollicutes nucleic acid in a sample. Other characteristics include limited cross-reactivity with other Bacteria or mammalian nucleic acid and targeting 23S rRNA. Any component(s), composition(s), or method step(s) that have a material effect on the basic and novel characteristics of the present invention would fall outside of this term.

As used herein, an oligonucleotide "substantially corresponding to" a specified nucleic acid sequence means that the referred to oligonucleotide is sufficiently similar to the reference nucleic acid sequence such that the oligonucleotide has similar hybridization properties to the reference nucleic acid sequence in that it would hybridize with the same target nucleic acid sequence under stringent hybridization conditions. One skilled in the art will understand that "substantially corresponding oligonucleotides" can vary from the referred to sequence and still hybridize to the same target nucleic acid sequence. It is also understood that a first nucleic acid corresponding to a second nucleic acid includes the complements thereof and includes the RNA and DNA thereof. This variation from the nucleic acid may be stated in terms of a percentage of identical bases within the sequence or the percentage of perfectly complementary bases between the probe or primer and its target sequence. Thus, an oligonucleotide "substantially corresponds" to a reference nucleic acid sequence if the nucleotide sequence of the first nucleic acid is from 100% to about 70% identical, or in some instances complementary, to the reference nucleic acid sequence. This range is inclusive of whole and partial numbers, e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. In preferred embodiments, the percentage is from 100% to about 85%. In more preferred embodiments, this percentage can be from 100% to about 90%; in other preferred embodiments, this percentage is from 100% to about 95%. Similarly, a region of a nucleic acid or amplified nucleic acid can be referred to herein as corresponding to a reference nucleic acid sequence. One skilled in the art will understand the various modifications to the hybridization conditions that might be required at various percentages of complementarity to allow hybridization to a specific target sequence without causing an unacceptable level of non-specific hybridization.

As used herein, a "blocking moiety" is a substance used to "block" the 3'-terminus of an oligonucleotide or other nucleic acid so that it cannot be efficiently extended by a nucleic acid polymerase. Oligomers not intended for extension by a nucleic acid polymerase may include a blocker group that replaces the 3'OH to prevent enzyme-mediated extension of the oligomer in an amplification reaction. For example, blocked amplification oligomers and/or detection probes present during amplification may not have functional 3'OH and instead include one or more blocking groups located at or near the 3' end. In some embodiments a blocking group near the 3' end and may be within five residues of the 3' end and is sufficiently large to limit binding of a polymerase to the oligomer. In other embodiments a blocking group is covalently attached to the 3' terminus. Many different chemical groups may be used to block the 3' end, e.g., alkyl groups, non-nucleotide linkers, alkane-diol dideoxynucleotide residues, and cordycepin.

An "amplification oligomer" is an oligomer, at least the 3'-end of which is complementary to a target nucleic acid, and which hybridizes to a target nucleic acid, or its complement, and participates in a nucleic acid amplification reaction. An example of an amplification oligomer is a "primer" that hybridizes to a target nucleic acid and contains a 3' OH end that is extended by a polymerase in an amplification process. Another example of an amplification oligomer is an oligomer that is not extended by a polymerase (e.g., because it has a 3' blocked end) but participates in or facilitates amplification. For example, the 5' region of an amplification oligonucleotide may include a promoter sequence that is non-complementary to the target nucleic acid (which may be referred to as a "promoter-primer" or "promoter provider"). Those skilled in the art will understand that an amplification oligomer that functions as a primer may be modified to include a 5' promoter sequence, and thus function as a promoter-primer. Further an amplification oligomer that functions as a primer may be modified to include a 5' tag region, thereby incorporating into an initial amplification product or amplification product a universal sequence. Size ranges for the target hybridizing regions of amplification oligonucleotides include those that are about 10 to about 70 nt in length and are substantially complementary to a region of the target nucleic acid sequence (or a complementary strand thereof).

As used herein, a "promoter" is a specific nucleic acid sequence that is recognized by a DNA-dependent RNA polymerase ("transcriptase") as a signal to bind to the nucleic acid and begin the transcription of RNA at a specific site.

As used herein, a "promoter-provider" or "provider" refers to an oligonucleotide comprising first and second regions, and which is modified to prevent the initiation of DNA synthesis from its 3'-terminus. The "first region" or "target hybridizing region" of a promoter-provider oligonucleotide comprises a base sequence which hybridizes to a DNA template, where the hybridizing sequence is situated 3', but not necessarily adjacent to, a promoter region. The target hybridizing region of a promoter-based oligonucleotide is typically at least 10 nucleotides in length, and may extend up to 50 or more nucleotides in length. The "second region" or "promoter region" comprises a promoter sequence for an RNA polymerase. A promoter oligonucleotide is engineered so that it is incapable of being extended by an RNA- or DNA-dependent DNA polymerase, e.g., reverse transcriptase, preferably comprising a blocking moiety at its 3'-terminus as described above. As referred to herein, a "T7 Provider" is a blocked promoter-provider oligonucleotide that provides an oligonucleotide sequence that is recognized by T7 RNA polymerase. A similar oligomer that lacks modification to the 3'-terminus is called a "promoter primer."

As used herein, a "blocker oligonucleotide" is an oligonucleotide comprising a base sequence that is complementary to a region of the target nucleic acid in the vicinity of the 5'-end of the target sequence, so as to "terminate" primer extension of a nascent nucleic acid that includes a priming oligonucleotide, thereby providing a defined 3'-end for the nascent nucleic acid strand.

The term "initial amplification product" is used herein in reference to synthesis of a complementary strand of nucleic acid, wherein said synthesis incorporates into the newly synthesized strand a tag region sequence. In subsequent amplifications wherein the template nucleic acid comprises such a tag region sequence or complement thereof or the term "amplification product" is used. Referencing the TMA amplification described above, the initial amplification product is the product generated from the RNA template using the tagged amplification oligomer to incorporate the tag region into the initial amplification product. The amplification product is, therefore, the product that is generated following degradation of the original target nucleic acid from the new DNA strand, which for the above exemplary amplification would include product generated using the promoter-based amplification oligomer, product generated by the RNA polymerase and product generated using the tag-targeting amplification oligomers. This detailed description is used to help with understanding of these terms. The use of two terms for the nucleic acids synthesized in the amplification reaction is merely for convenience and does not limit the current invention. Similarly, ordinarily skilled artisans will understand how these terms apply with other isothermal and cyclical amplification methods.

"Probe," "detection probe" or "detection oligonucleotide" are terms referring to a nucleic acid oligomer that hybridizes specifically to a target sequence in a nucleic acid, or in an amplified nucleic acid, under conditions that promote hybridization to allow detection of the target sequence or amplified nucleic acid. Detection may either be direct (e.g., a probe hybridized directly to its target sequence) or indirect (e.g., a probe linked to its target via an intermediate molecular structure). Probes may be DNA, RNA, analogs thereof or combinations thereof and they may be labeled or unlabeled. A probe's "target sequence" generally refers to a smaller nucleic acid sequence region within a larger nucleic acid sequence that hybridizes specifically to at least a portion of a probe oligomer by standard base pairing. A probe may comprise target-specific sequences and other sequences that contribute to the three-dimensional conformation of the probe (e.g., U.S. Pat. Nos. 5,118,801; 5,312,728; 6,849,412; 6,835,542; 6,534,274; and 6,361,945; and U.S. Pub. No. 20060068417).

As used herein, a "target capture oligomer" or "target capture probe" refers to a nucleic acid oligomer that specifically hybridizes to a target sequence in a target nucleic acid by standard base pairing and joins to a binding partner on an immobilized probe to capture the target nucleic acid to a support. One example of a target capture oligomer includes two binding regions: the first being a target-hybridizing region and the second being an immobilized probe-binding region. The two regions may be present on two different oligomers joined together by one or more linkers, or the two regions may be on the same oligomer. Another embodiment of a capture oligomer uses a target binding region that includes random or non-random poly-GU, poly-GT, or poly U sequences to bind non-specifically to a target nucleic acid and link it to an immobilized probe on a support. The immobilized probe-binding region may be a heteropolymeric nucleotide sequence or a homopolymeric nucleotide sequence. Exemplary heteropolymeric sequences include $dT_3/dT_{30}$ nucleotide sequences. Exemplary homopolymeric nucleotide sequences include $dT_{30}$, $dA_{30}$, $dC_{30}$ or $dG_{30}$ nucleotide sequences. (See e.g., U.S. Pat. Nos. 6,110,678, 6,280,952, and 6,534,273 and U.S. Pub. No. 2008-0286775 A1).

As used herein, an "immobilized oligonucleotide", "immobilized probe" or "immobilized nucleic acid" refers to a nucleic acid binding partner that joins a capture oligomer to a support, directly or indirectly. An immobilized probe joined to a support facilitates separation of a capture probe bound target from unbound material in a sample. One embodiment of an immobilized probe is an oligomer joined to a support that facilitates separation of bound target sequence from unbound material in a sample. Supports may include known materials, such as matrices and particles free in solution, which may be made of nitrocellulose, nylon, glass, polyacrylate, mixed polymers, polystyrene, silane, polypropylene, metal, or other compositions, of which one embodiment is magnetically attractable particles. Supports may be monodisperse magnetic spheres (e.g., uniform size ±5%), to which an immobilized probe is joined directly (via covalent linkage, chelation, or ionic interaction), or indirectly (via one or more linkers), where the linkage or interaction between the probe and support is stable during hybridization conditions.

By "complementary" is meant that the nucleotide sequences of similar regions of two single-stranded nucleic acids, or to different regions of the same single-stranded nucleic acid have a nucleotide base composition that allow the single-stranded regions to hybridize together in a stable double-stranded hydrogen-bonded region under stringent hybridization or amplification conditions. Sequences that hybridize to each other may be completely complementary or partially complementary to the intended target sequence by standard nucleic acid base pairing (e.g. G:C, A:T or A:U pairing). By "sufficiently complementary" or "substantially complementary" is meant a contiguous sequence that is capable of hybridizing to another sequence by hydrogen bonding between a series of complementary bases, which may be complementary at each position in the sequence by standard base pairing or may contain one or more residues, including abasic residues, that are not complementary. Sufficiently complementary contiguous bases are at least 80%, 81%, 82%, 83%, 84%, 85%, 86%, 87%, 88%, 89%, 90%, 91%, 92%, 93%, 94%, 95%, 96%, 97%, 98%, 99% or 100% complementary to the target sequence to which the target hybridizing region hybridizes. Skilled artisans know that such complementarity need not include only whole numbers (e.g., a 27 nucleotide oligomer having 22 nucleotides that are complementary to a target sequence will have an 81.48% complementarity to the target). Sequences that are "sufficiently complementary" allow stable hybridization of a nucleic acid oligomer with its target sequence under appropriate hybridization conditions, even if the sequences are not completely complementary. The same applies to sequence identity, wherein one nucleic acid has a nucleic acid sequence that is all or partially identical to a nucleotide sequence within another nucleic acid molecule.

By "preferentially hybridize" or "specifically hybridize" is meant that under stringent hybridization assay conditions, oligomers hybridize to the reference target sequence, or replicates thereof, to form stable oligomer:target hybrids, while at the same time formation of stable oligomer:non-target hybrids is minimized Thus, an oligomer hybridizes to a target sequence or replicate thereof to a sufficiently greater extent than to a non-target sequence, to enable one having ordinary skill in the art to accurately quantitate the RNA replicates or complementary DNA (cDNA) of the target sequence formed during the amplification. Compositions that are configured to specifically hybridize to a reference sequence are not limited to hybridizing only that reference sequence (e.g., only the *Mycoplasma hominis* species exemplified by SEQ ID NO:1). Rather, all that is meant is that such compositions have a nucleotide sequence that specifically hybridizes to the reference sequence but the composition will hybridize other species sequences (e.g., oligomers configured to specifically hybridize to a region of SEQ ID NO:1 will also hybridize the corresponding region in other *Mycoplasma* species). Compositions that specifically hybridize to a region of a target nucleic acid may have one or more of a nucleotide addition, deletion, mismatch, or modified nucleotide relative to a corresponding residue on the target nucleic acid.

"Sample preparation" refers to any steps or method that treats a sample for subsequent amplification and/or detection of Mollicutes nucleic acids present in the sample. Samples may be complex mixtures of components of which the target nucleic acid is a minority component. Sample preparation may include any known method of concentrating components, such as microbes or nucleic acids, from a larger sample volume, such as by filtration of airborne or waterborne particles from a larger volume sample or by isolation of microbes from a sample by using standard microbiology methods. Sample preparation may include physical disruption and/or chemical lysis of cellular components to release intracellular components into a substantially aqueous or organic phase and removal of debris, such as by using filtration, centrifugation or adsorption. Sample preparation may include use of one or more target capture oligomers.

The term "specificity," in the context of an amplification and/or detection system, is used herein to refer to the characteristic of the system which describes its ability to distinguish between target and non-target sequences dependent on sequence and assay conditions. In terms of nucleic acid amplification, specificity generally refers to the ratio of the number of specific amplicons produced to the number of side-products (e.g., the signal-to-noise ratio). In terms of detection, specificity generally refers to the ratio of signal produced from target nucleic acids to signal produced from non-target nucleic acids.

The term "sensitivity" is used herein to refer to the precision with which a nucleic acid amplification reaction can be detected or quantitated. The sensitivity of an amplification reaction is generally a measure of the smallest copy number of the target nucleic acid that can be reliably detected in the amplification system, and will depend, for example, on the detection assay being employed, and the specificity of the amplification reaction, e.g., the ratio of specific amplicons to side-products.

As used herein, the term "relative fluorescence unit" ("RFU") is an arbitrary unit of measurement of fluorescence intensity. RFU varies with the characteristics of the detection means used for the measurement.

As used herein, the term "TTime" is the threshold time or time of emergence of signal in a real-time plot of the assay data. TTime values estimate the time at which a particular threshold indicating amplicon production is passed in a real-time amplification reaction. TTime and an algorithm for calculating and using TTime values are described in U.S. Pub. No. 2006/0276972, paragraphs [0517] through [0538].

In a preferred embodiment, a 23S rRNA or a gene encoding the 23S rRNA of a species in the class Mollicutes is selectively separated from other sample components by specifically hybridizing the Mollicutes nucleic acid to a target capture oligomer to form a target sequence:target capture probe complex that is then separated from sample components. A preferred method of specific target capture binds the Mollicutes nucleic acid target sequence:target capture probe complex to an immobilized probe to form a nucleic acid target sequence:target capture probe-immobilized probe complex that is separated from the sample and, optionally, washed to remove non-target sample components. Also removed in this preferred embodiment is unhybridized tagged amplification oligomer, and more preferably inactivated unhybridized tagged amplification oligomer. The target capture probe preferably includes a a specific binding partner that attaches the capture probe with its bound target sequence to a solid support, to facilitate separating the target sequence from the sample components. In a preferred embodiment, the specific binding partner of the capture probe is a 3' heteropolymeric or homopolymeric tail sequence that is not complementary to the target sequence but that hybridizes to a complementary sequence on an immobilized probe attached to a solid support. Target capture preferably occurs in a solution phase mixture that contains one or more target capture oligomers that hybridize specifically to the target nucleic acid under hybridizing conditions, usually at a temperature higher than the Tm of the tail sequence:immobilized probe sequence duplex. Then, the target sequence:target capture probe complex is captured by adjusting the hybridization conditions so that the capture probe tail hybridizes to the immobilized probe, and the entire complex on the solid support is then separated from other sample components. Preferred embodiments use a particulate solid support, such as paramagnetic beads, so that particles with the attached target sequence:target capture probe-immobilized probe complex may be suspended in a washing solution and retrieved from the washing solution, preferably by using magnetic attraction. In a more preferred embodiment, the target capture occurs in solution phase and further comprises one or more tagged amplification oligomers, which bind to the target nucleic acid, thus forming part of the captured oligomer complex bound to the solid support. In this preferred embodiment, the tagged amplification oligomer is maintained with its target during the removal step, while unhybridized and/or inactivated unhybridized tagged amplification oligomer is removed, preferably via a wash step.

The following examples illustrate some of the embodiments of the invention for amplification of Mollicutes 23S rRNA target sequences. A plurality of tagged amplification oligomers were prepared and tested for sensitivity and specificity in amplifying and detecting different species in the class Mollicutes without interference from common cross reactors. The target species tested in these following examples include: *M. orale; M. arginini; M. hominis; M. synoviae; M. arthritidis; M. hyorhinis; A. laidlawii; Ureaplasma; S. citri; M. pneumoniae; M. gallisepticum; M. pirum; M. salivarium;* and *M. fermentans*. The following species were used as challenge organisms: *E. coli; C. perfringens; S. bovis; S. epidermidis; S. aureus; P. acnes; E. faecalis; B. subtillis; Clostridium sporogenes; Lactobacillus casei; Corynebacterium pseudodiphthericum; P. Aeruginosa; M. luteus;* and *L. pneumophila*. A Chinese Hamster Ovary (CHO) cell line was also used as a challenge organism. These target and challenge organisms are available from a variety of well known sources, including Poultry Diagnostic Research Center (Athens, Ga.) and biological depositories such as American Type Cell Culture (ATCC, Manassas, Va.) to name a few.

Example 1: Amplification of Target Nucleic Acid from Various Species in the class Mollicutes; Sensitivity and Specificity A first target capture reaction mixture was prepared to comprise a target capture oligomer (SEQ ID NO:29) and one of four tagged amplification oligomers (SEQ ID NO:73; SEQ ID NO:74; SEQ ID NO:75; or SEQ ID NO:76). The target capture oligomer was configured to hybridize to a target species nucleic acid at a position that also allows the target capture oligomer to perform as a blocker oligomer when these tagged amplification oligomers are used for generating an initial amplification product. The amplification reaction mixture comprised a promoter-based amplification oligomer (SEQ ID NO:15) and a tag-targeting amplification oligomer (SEQ ID NO:66). The target capture and amplification reactions were performed as is generally described herein. Briefly, lysates containing either 1000 copies of *M. fermentans* in the presence of either 1E+6 copies of the challenge organism *S. bovis* or 1E+6 copies of the challenge organism *E. coli* were incubated in target capture reagent for 60 minutes at 42.deg.0 followed by 15 minutes at room temp. A capture and was step was performed using magnetic beads and a KingFisher ml purification system. Following target capture, amplification reaction mixture was added to each of the reaction conditions and a TMA reaction was performed at 42.deg.0 using a molecular torch (SEQ ID NO:14). Positive cut-off was set at 1000 RFU. Three of the four tagged amplification oligomers showed good specificity for *M. fermentans* target at 1000 copies in the presence of both challenge organisms; and SEQ ID NO:76 showed was the best performer in this example. The results for SEQ ID NO:73 showed cross reactivity with *S. bovis*, having an average TTime of about 20.71 minutes (±7.1).

Further target capture and amplification reactions were prepared wherein the target capture mixtures comprised a target capture oligomer (SEQ ID NO:25) and one of the following tagged amplification oligomers (SEQ ID NOS:17, 18, 19, 20, 21, 22, 23 or 24) combined separately with each of the following blocker oligomers (SEQ ID NOS:25 or 26). The amplification reagent comprised a promoter-based amplification oligomer (SEQ ID NO:15) and a tag targeting oligomer (SEQ ID NO:16). Target nucleic acid was 0, 1E+3 or 1E+4 copies of *M. fermentans* nucleic acid. Target capture was performed as is generally described herein. Briefly, each of the samples were incubated at 60.deg.0 for 15 minutes followed by room temperature for 5 minutes. Target capture reagent was added to the sample and these mixtures were mixed, incubated and washed. Following target capture, amplification reaction mix was added to each of the reaction conditions and a TMA reaction was performed at 42.deg.0 in the presence of SEQ ID NO:27, which is a molecular torch. *M. fermentans* target nucleic acid was detected at 1E+3 and 1E+4 copies in each reaction condition, with TTimes ranging from about 12 to about 27 minutes. However, there were also false positives in samples comprising SEQ ID NOS:17, 18, 19 and 21 tagged amplification oligomers.

Example 2: Amplification of Target Nucleic Acid from Various Species in the Class Mollicutes; Sensitivity in Uniplex and Duplex Reactions Additional amplification and detection conditions were prepared to test the tagged amplification oligomer SEQ ID NO:76 in a uniplex reaction and in a duplex reaction. Two uniplex target capture reaction mixtures were prepared, the first comprising SEQ ID NO:29 and SEQ ID NO:76; and the second comprising SEQ ID NO:29 and SEQ ID NO:67 as a tagged amplification oligomer. A duplex target capture reaction mixture was prepared to comprise SEQ ID NO:29, SEQ ID NO:76 and SEQ ID NO:67. The amplification reaction mixture comprised SEQ ID NOS:15 & 66. The presence or absence of an amplification product was determined using SEQ ID NO:14. Target was 1E+2 or 1E+3 copies of each of *M. fermentans* (SEQ ID NO:76 uniplex reaction) or *M. gallisepticum; M. pneumoniae* or *Ureaplasma* (SEQ ID NO:67 uniplex reaction) and 1E+2 or 1E+3 copies of each of *M. fermentans, M. hyorhinus* and *M. gallisepticum* for the duplex reaction. Target capture and TMA were performed as is generally described herein. Positive samples were determined as those with RFUs above 1000. The uniplex reactions showed sensitivity to 1E+2 copies of all target nucleic acid tested. The duplex reaction also showed sensitivity to 1E+2 for *M. fermentans* and *M. gallisepticum*, but did not detect *M. hyorhinus*. Thus, the two tagged amplification oligomers did not interfere with each other and did not increase background, however, the oligomers did not detect one of the target species.

Example 3: Amplification of Target Nucleic Acid from Various Species in the class Mollicutes; Sensitivity in Duplex Reactions Additional tagged amplification oligomers were prepared and tested for sensitivity to *M. hyorhinus* sensitivity. *M. gallisepticum* was used as positive control. Four target capture reaction mixtures were prepared to comprise two target capture oligomers (SEQ ID NOS:28 & 29); a first tagged amplification oligomer (SEQ ID NO:67) and one of four second tagged amplification oligomers (SEQ ID NO:68; SEQ ID NO:74; SEQ ID NO:75; or SEQ ID NO:76). Both target capture oligomers were configured to hybridize to a target species nucleic acid at a position that also allows the target capture oligomer to perform as a blocker oligomer. The amplification reaction mixture comprised a promoter-based amplification oligomer (SEQ ID NO:15) and a tag-targeting amplification oligomer (SEQ ID NO:66). The presence or absence of an amplification product was determined using SEQ ID NO:14, a molecular torch. Target was 1E+2 or 1E+3 copies of *M. hyorhinus*. Positive control was 1E+2 or 1E+3 copies of *M. gallisepticum*. Negative control was water. Target capture and TMA amplification was performed as is generally described herein. All duplex reactions showed sensitivity to *M. gallisepticum* down to 1E+2 copies per reaction. Likewise, all duplex reactions amplified 1E+3 copies of *M. hyorhinus*, though only the duplex reactions comprising SEQ ID NO:68; SEQ ID NO:74 or SEQ ID NO:75 could amplify *M. hyorhinus* to 1E+2 copies.

Example 4: Amplification of Target Nucleic Acid from Various Species in the Class Mollicutes; Sensitivity in Multiplex Reactions Target capture reagent mixtures were prepared comprising three tagged amplification oligomers (SEQ ID NOS:67, 68 & 69) and two target capture oligomers (SEQ ID NOS:28 & 29). Samples containing target nucleic acids were prepared as follows, 0, 1E+2 or 1E+3 copies of *M. hyorhinus, M. arginini, M. hominus, M. orales, M. gallisepticum, M. pneumoniae, M. fermentans* or *A. laidlawii*. Target capture was performed as is generally described herein. Amplification reagent comprised SEQ ID NO:15 and SEQ ID NO:66 as promoter-based amplification oligomer and tag targeting amplification oligomer, respectively. TMA amplification was also performed as is generally described herein and detection of amplified product was performed using SEQ ID NO:14. In this multiplex reaction, all target nucleic acids were amplified well at 1E+3 copies of nucleic acid per reaction with an average TTime of about 22.51 minutes (±1.74). Similarly, all target nucleic acids at 1E+2 copies per reaction were amplified in these multiplex reactions average TTime of about 26.2 minutes (±1.78). There were no false positives.

In another multiplex reaction using the target capture reagent and the amplification reagent described directly above (target capture reagent comprises SEQ ID NOS:28, 29, 67, 68 & 69; and amplification reagent comprises SEQ ID NOS:15 & 66). In this reaction, the target nucleic acid was extracted from the following four organisms: *M. arthritidis, M. pirum, M. salvarium* and *M. gallisepticum*. Positive control was 1E+3 copies of 23S rRNA from *M. gallisepticum*. Samples were prepared at 1 CFU per reaction. The presence or absence of target nucleic acid was determined in real time using SEQ ID NO:14. In this multiplex reaction, all target nucleic acids were amplified at 1 CFU (approximately 1E+3 copies per CFU). The positive control was also positive and there were no false positives.

Example 5: Amplification of Target Nucleic Acid from Various Species in the Class Mollicutes in the Presence of Challenge Nucleic Acids; Sensitivity in Multiplex Reactions Target capture reagent mixtures were prepared comprising three tagged amplification oligomers (SEQ ID NOS:67, 68 & 69) and two target capture oligomers (SEQ ID NOS:28 & 29). Samples contained 1E+8 copies of nucleic acid from one of the following challenge organisms: *S. epidermidis, S. bovis, M. luteus, B. subtillis, E. coli, L. pneumophilia, P. aeruginosa*, Chinese Hamster Ovary (CHO) cell, *Clostridium sporo genes, Lactobacillus casel*, or *Corynebacterium pseudodiphtheriticum*. These samples were prepared in duplicate and one of the duplicates contained 1E+3 copies of *M. gallisepticum* and the other of the duplicates did not. Positive control was *M. gallisepticum* (1E+3 copies of target nucleic acid), and negative controls were water. Target capture and TMA was performed as is generally described herein. Amplification product was detected in real time using SEQ ID NO:14. In this example, none of the challenge organisms inhibited amplification of the target nucleic acid (*M. gallisepticum*). 1E+3 copies of *M. gallisepticum* was amplified in the presence of 1E+8 copies of each challenge organisms with average TTimes ranging from about 27.6 to about 28.8 minutes. Six of the challenge organisms were negative (0 of 4). *S. epidermidis, E. coli; S. bovis* and *M. luteus* challenge organisms each showed 1 of 4 positive in this experiment with TTimes of about 36.6 minutes, 42.4 minutes, 40.8 minutes and 56.5 minutes, respectively. *L. pneumophilia* challenge organism showed 3 of 4 positives in this experiment, with an average TTime of about 51.2 minutes (±13.7).

Example 6: Capture and Amplification of Mollecutes Nucleic Acid

Target capture reagents were prepared to comprise the following: two target capture oligomers (SEQ ID NOS:28 & 29) and three tagged amplification oligomers (SEQ ID NOS:6, 30 & 31). The target capture oligomers are also blocker oligomers. The amplification reagent comprised a tag-targeting amplification oligomer (SEQ ID NO:33) and a promoter-based amplification oligomer (SEQ ID NO:15). An internal control was also used in these reactions (target capture reagent comprised SEQ ID NOS:32 & 35, amplification reagent comprised SEQ ID NOS:34 & 36). Amplification product was detected in real time using either SEQ ID NO:14 or SEQ ID NO:37. Target capture and amplification were performed as is generally described herein. Target nucleic acid was 1E+5 copies of *M. gallisepticum* 23S rRNA. Negative control was water. Each sample condition further comprised an in vitro transcript as internal control. Each test reaction condition was positive for 1E+5 copies of *M. gallisepticum*. There were no false positives.

Example 7: Capture and Amplification of Mollecutes Nucleic Acid in the Presence of a Challenge Nucleic Acid The performance of three different target capture systems was compared. Each system was tested with 1E+04 copies

*M. hominis* (ATCC 41561) as positive control and *C. perfringens* (ATCC 13124) lysate as challenge nucleic acid at 1E+07 and 1E+08 copies. Three separate target capture reaction mixtures were prepared, each reaction mixture comprised four tagged amplification oligomers (SEQ ID NOS:5, 6, 7 & 8); and a first of the three reaction mixtures further comprised two target capture oligomers (SEQ ID NOS:11 & SEQ ID NO:12) and two blocker oligomers (SEQ ID NOS:9 & 10), the second of the three reaction mixtures further comprised two target capture oligomers (SEQ ID NOS:64 & 65) and two blocker oligomers (SEQ ID NOS:9 & 10), and the third of the three reaction mixtures further comprised two target capture oligomers (SEQ ID NOS:28 & 29). In the third of the three reaction mixtures, the target capture oligomers were also used as blocker oligomers. The nucleotide sequences of the target hybridizing regions of both SEQ ID NOS:11 & 12 are 2-O-Me RNA residues. An internal control was also used, and thus all three reaction mixtures further comprised an in vitro transcript as internal control and SEQ ID NO:32 as a target capture oligomer for the in vitro transcript. Each of the target capture reagents was added to samples containing either the positive lysates or the cross reactor lysates. A negative control reaction comprised only water. These reactions were incubated at 45 minutes at 60.deg.0 and then cooled at room temperature for 15 minutes. Target capture was then performed using magnetic beads and a KingFisher mL purification system.

Following target capture, amplification reagent was added to each of the reaction conditions. The amplification reagent comprised a promoter-based amplification oligomer (SEQ ID NO:15) and two tag targeting oligomers, (SEQ ID NOS:13 & 33). Amplification oligomers directed to the internal control were also included (SEQ ID NOS:34, 35 & 36). These reaction mixtures were then incubated at 42.deg.C, and amplification product was detected using one molecular torch for the sample and another for the internal control (SEQ ID NOS:14 & 37, respectively). Positive cut-off was set at 2000 RFU. Results are shown in Table 1. Sensitivity of each of the three target capture systems was comparable. The target capture oligomers comprising 2-O-Me nucleotide residues in the target capture regions were more selective against the challenge organism than were the deoxy target capture oligomers.

TABLE 1

Summary of Results.

| Target Capture Oligomer SEQ ID NOS: | Target/Target Amount | Total/# Positive | AVG TTime1/ SD | Avg TTime2/ SD |
|---|---|---|---|---|
| 13 & 14 | ATCC 13124/1E+7 | 12/3 | 35.8/8.92 | 39.36/1.79 |
| 13 & 14 | ATCC 13124/1E+8 | 12/6 | 39.8/8.66 | 39.01/2.07 |
| 13 & 14 | 0/0 | 4/0 | 0/0 | 40.03/1.84 |
| 13 & 14 | ATCC 41561/1E+4 | 4/4 | 24.0/0.86 | 44.32/1.31 |
| 11 & 12 | ATCC 13124 | 12/0 | 0/0 | 36.30/2.82 |
| 11 & 12 | ATCC 13124 | 12/1 | 40.7/0 | 35.99/2.61 |
| 11 & 12 | 0/0 | 4/0 | 0/0 | 35.17/0.78 |
| 11 & 12 | ATCC 41561/1E+4 | 4/4 | 25.8/0.53 | 38.28/2.52 |
| 15 & 16 | ATCC 13124 | 12/2 | 41.3/11.92 | 38.17/1.92 |
| 15 & 16 | ATCC 13124 | 12/7 | 39.2/7.81 | 38.18/1.55 |
| 15 & 16 | 0/0 | 4/0 | 0/0 | 36.73/1.44 |
| 15 & 16 | ATCC 41561/1E+4 | 4/4 | 25.6/1.53 | 38.91/1.51 |

Example 8: Capture and Amplification of Mollecutes Nucleic Acid in the Presence of a Challenge Nucleic Acid The performance of two different target capture systems was compared using 1E+3 copies of *M. gallisepticum* as a positive control and using 1E+7 copies of *S. aureus* or ~2E+8 copies of *E. faecalis* as challenge organisms. In this example, the two lysis reaction mixtures were prepared as described in Example 7, above, for the first reaction mixture comprising two target capture oligomers (SEQ ID NOS:11 & SEQ ID NO:12) and two blocker oligomers (SEQ ID NOS:9 & 10), and for the third reaction mixture comprising two target capture oligomers (SEQ ID NOS:28 & 29). An internal control was used as described above. Each of the lysis reagents was added to samples containing either the positive lysates or one of the cross reactor lysates. A negative control reaction comprised only water. These reactions were incubated at 45 minutes at 60.deg.C and then cooled at room temperature for 15 minutes. Target capture was then performed using magnetic beads and a KingFisher mL purification system. Amplification reagent, described above, was then added to each of the reaction conditions and the reactions were then incubated at 42.deg.C. A molecular torch was also present in the reaction for real time detection of amplification product (SEQ ID NOS:14 for the sample & 37 for the internal control). Positive cut-off was set at 2000 RFU.

The target capture system comprising SEQ ID NOS:28 & 29 as target capture oligomers and SEQ ID NO:33 as a tag-targeting oligomer showed positive results for three of four samples containing 1E+3 copies of *M. gallisepticum*, with an average TTime of about 32.2 minutes (±12.85). This system provided no false positives and no cross reactivity with the *S. aureus* cross reacting organism. However, this system did show 6 of 12 positive reactions for *E. faecalis* with an average TTime of about 38.7 minutes (±7.18). Using the SEQ ID NO:13 tag-targeting oligomer with these same target capture oligomers (SEQ ID NOS:28 & 29) provided positive results for three of four samples containing 1E+3 copies of *M. gallisepticum*, with an average TTime of about 26 minutes (±2.76). This system provided no false positives and no cross reactivity with the *S. aureus* cross reacting organism. But, this system did show 7 of 12 positive reactions for *E. faecalis* with an average TTime of about 40.7 minutes (±4.9). The target capture system comprising SEQ ID NOS:11 & 12 as target capture oligomers and SEQ ID NO:13 as a tag-targeting oligomer showed provided positive results for two of four samples containing 1E+3 copies of *M. gallisepticum*, though one was only weakly positive, with an average TTime of about 41 minutes (±19.47). This system provided no false positives, no cross reactivity with the *S. aureus* challenge organism, and 1 of 12 positive reactions for *E. faecalis* with a TTime of about 37.8 minutes.

Example 9: Amplification of Target Nucleic Acid from Various Species in the Class Mollicutes in the Presence of Challenge Nucleic Acids; Sensitivity in Multiplex Reactions A multiplex reaction was performed to detect each of six different target nucleic acids in the presence of each of four challenge organisms. For this reaction, target organisms were *M. salvarium*, *M. hyorhinis*, *M. synoviae*, *M. arthritidis*, *M. pneumoniae* and *S. citri*. Challenge organisms were *B. subtilis*, *M. luteus*, *P. acnes* and *P. aeruginosa*. Positive control was *M. gallisepticum* and negative control was water. Target and challenge organisms were present at about 1E+4 copies (~1E+3 copies per CFU). Challenge organisms were also tested at about 1E+7 copies per reaction. Target capture reagent comprised the following: two target capture oligomers (SEQ ID NOS:11 & 12), four tagged amplification oligomers (SEQ ID NOS:5, 6, 7 & 8) and two blocker oligomers (SEQ ID NOS:9 & 10). Amplification reagent comprised the following: a tag-targeting oligomer (SEQ ID NOS:13) and a promoter-based amplification oligomer (SEQ ID NO:15). A molecular torch was used for real time detection of amplifications product (SEQ ID NO:14). An internal control system was included as described herein and comprising an in vitro transcript and SEQ ID NOS:32, 34, 35, 36 & 37. Target capture, amplification and real-time detection of amplification product were performed as is generally described herein. Results showed that the *M. gallisepticum* control was positive with TTimes of about 20 to 23 minutes, though there was 1 of 8 false positives. All target organisms were amplified except for *M. pneumoniae*, which was later determined to have been the result of a miscalculation in concentration, see below. *M. salvarium* was positive with an average TTime of about 25 minutes, *M. hyorhinis* was positive with an average TTime of about 25 minutes, *M. synoviae* was positive with an average TTime of about 25 minutes, *M. arthritidis* was positive with an average TTime of about 25 minutes, *M. pneumoniae* and *S. citri* was positive with an average TTime of about 25 minutes. Challenge organisms *B. subtilis, M. luteus, P. acnes* and *P. aeruginosa* were each mostly negative, though *B. subtilis* and *P. aeruginosa* had 1 of 8 positives and *M. luteus* showed a low riser (RFU greater than 2000 at a TTime of about 55-60 minutes).

An amplification reaction was performed as described above, but using a serial dilution of *M. pneumoniae* to determine whether the results obtained in the reaction directly above are due to a concentration error in the stock reagent or are attributable to the assay reagents. Target nucleic acids included 0 or 1E+4 copeis per reaction of the following: *M. hominis, A. laidlawii* and *S. citri*. A serial dilution was made for the stock *M. pneumoniae*, and a 1:10 and 1:100 dilution was tested. Positive control was *M. gallisepticum*. Negative control was water. Target capture, amplification and real-time detection of amplification product were performed as is generally described herein. Results showed an average TTime of about 24 minutes for *M. gallisepticum* positive control. *M. hominis* had an average TTime of about 23 minutes, *A. laidlawii* had an average TTime of about 27 minutes and *S. critri* had an average TTime of about 27 minutes. *M. pneomoniae* serial dilutions showed average TTimes of about 28 minutes for both the 1:10 dilution and the 1:100 dilution. There were no false positives.

Example 10: Exemplary Oligomers, Reference Sequences and Oligomer Regions

In Table 2, below, there are exemplary oligomers, reference sequences and oligomer regions as described herein. The following nucleic acids are illustrated in this Table 2. Reference target nucleic acids are SEQ ID NOS:1-4. Tagged amplification oligomers, include SEQ ID NOS:5-8, 17-24, 30, 31, 40, 41, 49, 56, 57, 63 & 67-72. Tag closing regions (also called target closing regions) can be added or removed or modified on these tagged amplification oligomers as is described herein. Optionally, tag closing regions are joined to tag regions using one or more non-nucleotide linkers. Blocker oligomers include SEQ ID NOS:9, 10, 25 and 27. However, in some examples here, the target hybridizing region of a target capture oligomer also served as a blocker oligomer. Target capture oligomers include SEQ ID NOS: 11, 12, 28, 29, 64 & 65. Promoter-based oligomer includes SEQ ID NOS:15. Detection probes include SEQ ID NO:14 and SEQ ID NO:27. Tag-targeting amplification oligomers include SEQ ID NOS:13, 16, 33, 43, 44 & 66. These sequences or their complements, can also refer to tag region sequences contained within a tagged amplification oligomer, an initial amplification product and/or an amplification product. Target hybridizing regions include SEQ ID NOS:38, 39, 42, 46-48, 50-55 and 58-62. Internal control oligomers include SEQ ID NOS:32 & 34-37. SEQ ID NO:14 preferably comprises at least one 2'-O-Me residue, a 5' fluorescein and 3'dabcyl and/or a C9 linker between residues 20 and 21. SEQ ID NO:27 preferably comprises at least one 2'-O-Me residue, a 5' fluorescein and 3'dabcyl and/or a C9 linker between residues 5 and 6. Some oligomers further comprise one or more of a 2'-O-Me residue, a blocked 3'-terminus or a non-nucleotide linker. SEQ ID NO:77 is an exemplary promoter sequence for promoter-based oligomers.

TABLE 2

Exemplary Oligomers, Reference Sequences and Regions.

SEQ ID NO:Sequence (5' to 3')

| | | |
|---|---|---|
| 1 | | *Mycoplasma hominis*. GenBank Accession No. AF443616.3 GI: 110815963. First seen at NCBI on Jul. 28, 2006 |
| 2 | | *Mycoplasma gallisepticum*. GenBank Accession No. L08897.1 GI: 530152. First seen at NCBI on Aug. 17, 1994 |
| 3 | | Residues 75178 to 78004 of *Acholeplasma laidlawii*. CP000896.1 GI: 161984995. The residues correspond to the 223S rRNA gene. GenBank Accession No. CP000896.1 GI: 161984995 was first seen at NCBI on Dec. 7, 2007. |
| 4 | | *Spiroplasma insolitum*. GenBank Accession No. EU582532.1 GI: 175362846. First seen at NCBI on Apr. 12, 2008 |
| 5 | | CTAAATACTGACCTGCAGTAGGTACCGATGACGACCTTTCGTGCAGGTCAGTATTTAG |
| 6 | | TGTAACCATCTCCAGTAGGTACCGATGACGAGAGACAGTCAAGAGATGGTTACA |
| 7 | | GCCGGcagtaggtaccgatgacgaGTAGCCGGCGTTTTCACCGGC |
| 8 | | TGATCcagtaggtaccgatgacgaGCCGAGACAGCGAAGGGATCA |
| 9 | | CGCCGUUCACUGGGGCUUC |

TABLE 2-continued

Exemplary Oligomers, Reference Sequences and Regions.

| SEQ ID NO: | Sequence (5' to 3') |
|---|---|
| 10 | CGCCGUUCACCCGGGCUUC |
| 11 | ACGUGUGUUCGUUCUCGGaaaaaaaaaaaaaaaaaaaaaaaaaaaaa |
| 12 | CAACAGUUUUCUCGCGCGUtttaaaaaaaaaaaaaaaaaaaaaaaaaaaaa |
| 13 | TCGTcagtaggtaccgatgacga |
| 14 | ccAGGAAUUUCGCUACCUUAccugg |
| 15 | aatttaatacgactcactatagggagaACGGCGGCCGTAACTATAACGGTCCTAAGG |
| 16 | gaacctagttgggcgagttacgga |
| 17 | gaacctagttgggcgagttacggaCCTTTCGTGCAGGTCAGTAGTTAG |
| 18 | CTAACTACTGgaacctagttgggcgagttacggaCCTTTCGTGCAGGTCAGTAGTTAG |
| 19 | gaacctagttgggcgagttacggaCCTTTCGTGCAGGTCAGTA |
| 20 | TACTGgaacctagttgggcgagttacggaCCTTTCGTGCAGGTCAGTA |
| 21 | gaacctagttgggcgagttacggaCCTTTCGTGCAGGTCA |
| 22 | TGACCgaacctagttgggcgagttacggaCCTTTCGTGCAGGTCA |
| 23 | gaacctagttgggcgagttacggaTACACCATTCAAGCGGGACGGAATTTAC |
| 24 | GTAAATTCCGgaacctagttgggcgagttacggaTACACCATTCAAGCGGGACGGAATTTAC |
| 25 | CGCCGUUCACCGGG |
| 26 | CGCCGUUCACCGGGGCUUC |
| 27 | gcgaaCGACAAGGAAUUUCGC |
| 28 | CGCCGUUCACCCGGGCUUCtttaaaaaaaaaaaaaaaaaaaaaaaaaaaaa |
| 29 | CGCCGUUCACUGGGCUUCtttaaaaaaaaaaaaaaaaaaaaaaaaaaaaa |
| 30 | CTAATTACTGACCTGcagtaggtaccgatgacgaTCGTGCAGGTCAGTAATTAG |
| 31 | AACAGACTCGGTcagtaggtaccgatgacgaCAGCTTGATTTCACCGAGTCTGTT |
| 32 | CGUUCACUAUUGGUCUCUGCAUUCtttaaaaaaaaaaaaaaaaaaaaaaaaaaaaa |
| 33 | cagtaggtaccgatgacga |
| 34 | aatttaatacgactcactatagggagaccacaaAATAGATTATATAGGACGACAAGTAAAA |
| 35 | CUAUUGUCACUUCCUUGAGUAU |
| 36 | GACCATGTCCCAATTCGCACCAGG |
| 37 | CCACUUGCGAUGUUUUAAGUGG |
| 38 | TCGTGCAGGTCAGTADTTAG |
| 39 | CCTTTCGTGCAGGTCAGTADTTAG |
| 40 | cagtaggtaccgatgacgaTCGTGCAGGTCAGTADTTAG |
| 41 | CAGTAGGTACCGATGACGACCTTTCGTGCAGGTCAGTADTTAG |
| 42 | ACGGCGGCCGTAACTATAACGGTCCTAAGG |
| 43 | cagtaggtaccgatgacga |
| 44 | gaacctagttgggcgagttacgga |
| 45 | TACACCATTCAAGCGGGACGGAATTTAC |
| 46 | GAGACAGTCAAGAGATGGTTACA |
| 47 | GAGACAGTCAAGAGATGGTTA |

TABLE 2-continued

Exemplary Oligomers, Reference Sequences and Regions.

SEQ ID NO:Sequence (5' to 3')

| | |
|---|---|
| 48 | GAGACAGTCAAGAGATGG |
| 49 | CAGTAGGTACCGATGACGAGAGACAGTCAAGAGATGGTTACA |
| 50 | CAGCTTGATTTCACCGAGTCTGTT |
| 51 | GGCGTTTTCACCGGCAGCT |
| 52 | AGCCGGCGTTTTCACCGGCAG |
| 53 | GGTAGCCGGCGTTTTCACCGGCAG |
| 54 | GTAGCCGGCGTTTTCACCGGC |
| 55 | TAATCGCGGGTAGCCGGCGTT |
| 56 | cagtaggtaccgatgacgaCAGCTTGATTTCACCGAGTCTGTT |
| 57 | cagtaggtaccgatgacgaGTAGCCGGCGTTTTCACCGGC |
| 58 | GCCGAGACAGCGAAGGGATCA |
| 59 | GCAGCCGAGACAGCGAAGGG |
| 60 | AATTTCACCGAGTCTGCAGCC |
| 61 | AAATTTCACCGAGTCTGCAGCC |
| 62 | CTAAAATTTCACCGAGTCTGCAGCC |
| 63 | cagtaggtaccgatgacgaGCCGAGACAGCGAAGGGATCA |
| 64 | CAACAGTTTTCTCGCGCGTTTTAAAAAAAAAAAAAAAAAAAAAAAAAAAA |
| 65 | ACGTGTGTTCGTTCTCGGTTTAAAAAAAAAAAAAAAAAAAAAAAAAAA |
| 66 | GTTGACGTACCGTATTGA |
| 67 | gttgacgtaccgtattgaGAGACAGTCAAGAGATGGTTACA |
| 68 | gttgacgtaccgtattgaTCGTGCAGGTCAGTAATTAG |
| 69 | gttgacgtaccgtattgaCAGCTTGATTTCACCGAGTCTGTT |
| 70 | AGCTGCCGGTGAcagtaggtaccgatgacgaGGCGTTTTCACCGGCAGCT |
| 71 | TCGACGGCCACTcagtaggtaccgatgacgaGTAGCCGGCGTTTTCACCGGC |
| 72 | GTGAAATTTTAGcagtaggtaccgatgacgaCTAAAATTTCACCGAGTCTGCAGCC |
| 73 | GTTGACGTACCGTATTGACCTTTCGTGCAGGTCAGTAGTTAG |
| 74 | GTTGACGTACCGTATTGATTTCGTGCAGGTCAGTAGTTAG |
| 75 | GTTGACGTACCGTATTGATCGTGCAGGTCAGTAGTTAG |
| 76 | GTTGACGTACCGTATTGAGTGCAGGTCAGTAGTTAG |
| 78 | CGCCGUUCACYKGGGCUUC |

The methods illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the invention claimed. Thus, it should be understood that although the present invention has been specifically disclosed by preferred embodiments and optional features, modification and variation of the invention embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

Other embodiments also fall within the following claims. In addition, where features or aspects of the methods are described in terms of Markush groups, those skilled in the art will recognize that the invention is also thereby described in terms of any individual member or subgroup of members of the Markush group.

The invention claimed is:

1. A method for the in vitro amplification of a nucleic acid in a sample, the nucleic acid being from one or more species in the class Mollicutes, comprising the steps of:
(a) contacting a sample with at least two tagged amplification oligomers, each of which individually comprises a target hybridizing region and a tag region, wherein the at least two tagged amplification oligomers are selected from the group consisting of:
  (i) a tagged amplification oligomer comprising a target hybridizing region that is from 15 to 50 nucleobases in length and contains a nucleotide sequence that is configured to specifically hybridize to all or a portion of a region of a target nucleic acid corresponding to residues 5065 to 5088 of SEQ ID NO:1;
  (ii) a tagged amplification oligomer comprising a target hybridizing region that is from 15 to 50 nucleobases in length and contains a nucleotide sequence that is configured to specifically hybridize to all or a portion of a region of a target nucleic acid corresponding to residues 4752 to 4798 of SEQ ID NO:2;
  (iii) a tagged amplification oligomer comprising a target hybridizing region that is from 15 to 50 nucleobases in length and contains a nucleotide sequence that is configured to specifically hybridize to all or a portion of a region of a target nucleic acid corresponding to residues 1954 to 2006 of SEQ ID NO:3; and
  (iv) a tagged amplification oligomer comprising a target hybridizing region that is from 15 to 50 nucleobases in length and contains a nucleotide sequence that is configured to specifically hybridize to all or a portion of a region of a target nucleic acid corresponding to residues 1994 to 2036 of SEQ ID NO:4;
  wherein the tag region of each tagged amplification oligomer has the same nucleotide sequence; and
(b) providing suitable conditions for performing an in vitro amplification reaction.

2. A reaction mixture for generating initial amplification products from one or more species of the class Mollicutes in a sample, wherein the reaction mixture comprises at least four different tagged amplification oligomers wherein each of the at least four different tagged amplification oligomers is selected from the group consisting of:
  (i) a tagged amplification oligomer comprising a target hybridizing region that is from 15 to 50 nucleobases in length and contains a nucleotide sequence that is configured to specifically hybridize to all or a portion of a region of a target nucleic acid corresponding to residues 5065 to 5088 of SEQ ID NO:1;
  (ii) a tagged amplification oligomer comprising a target hybridizing region that is from 15 to 50 nucleobases in length and contains a nucleotide sequence that is configured to specifically hybridize to all or a portion of a region of a target nucleic acid corresponding to residues 4752 to 4798 of SEQ ID NO:2;
  (iii) a tagged amplification oligomer comprising a target hybridizing region that is from 15 to 50 nucleobases in length and contains a nucleotide sequence that is configured to specifically hybridize to all or a portion of a region of a target nucleic acid corresponding to residues 1954 to 2006 of SEQ ID NO:3; and
  (iv) a tagged amplification oligomer comprising a target hybridizing region that is from 15 to 50 nucleobases in length and contains a nucleotide sequence that is configured to specifically hybridize to all or a portion of a region of a target nucleic acid corresponding to residues 1994 to 2036 of SEQ ID No:4,
  wherein each of the at least four different tagged amplification oligomers contains a tag region comprising a tag sequence located 5' of the target hybridizing sequence, wherein the tag sequence for each of the at least four different tagged amplification oligomers comprises the same nucleotide sequence or a complement thereof, and wherein the tag sequence is not identical to a Mollicute nucleotide sequence, and
  wherein each of the at least four different tagged amplification oligomers is capable of generating an initial nucleic acid amplification product from a different species of the class Mollicutes.

3. The reaction mixture of claim 2, wherein at least one of the at least four different tagged amplification oligomers is (iv), wherein the target hybridizing region is from 20 to 25 nucleobases in length.

4. The reaction mixture of claim 2, wherein the tag sequence is from 18 to 24 nucleobases in length.

5. The reaction mixture of claim 4, wherein the tag sequence comprises a sequence having at least 95% identity to SEQ ID NO:43 or a complement thereof, or a sequence having at least 95% identity to SEQ ID NO:44 or a complement thereof.

6. The reaction mixture of claim 2, wherein one or more of the four tagged amplification oligomers further comprises a tag-closing region that is 3 to 20 nucleobases in length and that hybridizes under a set of conditions to all or a portion of the target hybridizing region and thereby places the tagged amplification oligomer into a closed inactive configuration.

7. The reaction mixture of claim 2, wherein the reaction mixture further contains a promoter-based amplification oligonucleotide.

8. The reaction mixture of claim 2, further comprising one or more additional amplification oligomers selected from the group consisting of: a tag-targeting amplification oligomer, a primer oligomer, a promoter-based amplification oligomer, and combinations thereof.

9. The reaction mixture of claim 2, further comprising a tag-targeting amplification oligomer comprising a target hybridizing region configured to specifically hybridize to the tag sequence, wherein the tag sequence comprises a sequence having at least 95% identity to SEQ ID NO:43 or a complement thereof, or a sequence having at least 95% identity to SEQ ID NO:44 or a complement thereof and optionally, wherein the target hybridizing region of the tag-targeting amplification oligomer is from 18 to 24 nucleobases in length.

10. The reaction mixture of claim 2, further comprising a promoter-based amplification oligomer comprising a target hybridizing region that is from 10 to 50 nucleobases in length, wherein (a) the target hybridizing region of the promoter-based amplification oligomer comprises a sequence configured to specifically hybridize to at least 10 contiguous nucleotides of residues 5016 to 5045 of SEQ ID NO:1; (b) the target hybridizing region of the promoter-based amplification oligomer comprises a sequence that is at least 95% identical to SEQ ID NO:42; or, (c) the promoter-based amplification oligomer has a sequence consisting of the sequence of SEQ ID NO:15.

11. The reaction mixture of claim 2, wherein the reaction mixture further comprises a blocker oligomer consisting of SEQ ID NO:78.

12. The reaction mixture of claim 2, wherein the reaction mixture further comprises two blocker oligomers, the first consisting of SEQ ID NO:9 and the second consisting of SEQ ID NO:10.

13. The reaction mixture of claim 2, further comprising at least one target capture oligomer.

14. The reaction mixture of claim 13, wherein the at least one target capture oligomer is selected from the group consisting of SEQ ID NO:11, SEQ ID NO:12, SEQ ID NO:28, SEQ ID NO:29, SEQ ID NO:64, SEQ ID NO:65 and combinations thereof.

15. A composition for determining the presence or absence of one or more species from the Mollicutes class in a sample, the composition comprising four different tagged amplification oligomers, each comprising a target hybridizing region and a tag region, wherein each of the four different tagged amplification oligomers is selected from the group consisting of:
(i) a tagged amplification oligomer comprising a target hybridizing region that is from 15 to 50 nucleobases in length and contains a nucleotide sequence that is configured to specifically hybridize to all or a portion of a region of a target nucleic acid corresponding to residues 5065 to 5088 of SEQ ID NO:1;
(ii) a tagged amplification oligomer comprising a target hybridizing region that is from 15 to 50 nucleobases in length and contains a nucleotide sequence that is configured to specifically hybridize to all or a portion of a region of a target nucleic acid corresponding to residues 4752 to 4798 of SEQ ID NO:2;
(iii) a tagged amplification oligomer comprising a target hybridizing region that is from 15 to 50 nucleobases in length and contains a nucleotide sequence that is configured to specifically hybridize to all or a portion of a region of a target nucleic acid corresponding to residues 1954 to 2006 of SEQ ID NO:3; and
(iv) a tagged amplification oligomer comprising a target hybridizing region that is from 15 to 50 nucleobases in length and contains a nucleotide sequence that is configured to specifically hybridize to all or a portion of a region of a target nucleic acid corresponding to residues 1994 to 2036 of SEQ ID NO:4,
wherein the tag region of each tagged amplification oligomer has the same nucleotide sequence, wherein the tag region is located 5' of the target hybridizing sequence, and wherein the tag region nucleotide sequence is not identical to a Mollicute nucleotide sequence.

16. The composition of claim 15, wherein at least one of the four different amplification oligomers is (iv), wherein the target hybridizing region is from 20 to 25 nucleotides in length, and wherein the tag region nucleotide sequence comprises a sequence having at least 95% identity to SEQ ID NO: 43, or a complement thereof, or a sequence having at least 95% identity to SEQ ID NO: 44 or a complement thereof.

17. The composition of claim 15, wherein the four different tagged amplification oligomers comprise a first tagged amplification oligomer and a second tagged amplification oligomer, wherein the first tagged amplification oligomer comprises the nucleotide sequence of SEQ ID NO:5, and the second tagged amplification oligomer comprises a nucleotide sequence selected from the group consisting of: a sequence having at least 95% identity to SEQ ID NO:6, a sequence having at least 95% identity to SEQ ID NO:7, and a sequence having at least 95% identity to SEQ ID NO:8.

18. The composition of claim 15, wherein the four different tagged amplification oligomers comprise a first tagged amplification oligomer and a second tagged amplification oligomer, wherein the first tagged amplification oligomer comprises the nucleotide sequence of SEQ ID NO:6, and the second tagged amplification oligomer comprises a nucleotide sequence selected from the group consisting of: a sequence having at least 95% identity to SEQ ID NO:5, a sequence having at least 95% identity to SEQ ID NO:7, and a sequence having at least 95% identity to SEQ ID NO:8.

19. The composition of claim 15, wherein the four different tagged amplification oligomers comprise a first tagged amplification oligomer and a second tagged amplification oligomer, wherein the first tagged amplification oligomer comprises the nucleotide sequence of SEQ ID NO:7, and the second tagged amplification oligomer comprises a nucleotide sequence selected from the group consisting of: a sequence having at least 95% identity to SEQ ID NO:5, a sequence having at least 95% identity to SEQ ID NO:6, and a sequence having at least 95% identity to SEQ ID NO:8.

20. The composition of claim 15, wherein the four different tagged amplification oligomers comprise a first tagged amplification oligomer and a second tagged amplification oligomer, wherein the first tagged amplification oligomer comprises the nucleotide sequence of SEQ ID NO:8, and the second tagged amplification oligomer comprises a nucleotide sequence selected from the group consisting of: a sequence having at least 95% identity to SEQ ID NO:5, a sequence having at least 95% identity to SEQ ID NO:6, and a sequence having at least 95% identity to SEQ ID NO:7.

21. The reaction mixture of claim 2, wherein the four different tagged amplification oligomers comprise:

(a) a first tagged amplification oligomer comprising a target hybridizing region that is from 15 to 50 nucleobases in length and contains a nucleotide sequence that is configured to specifically hybridize to all or a portion of a region of a target nucleic acid corresponding to residues 5065 to 5088 of SEQ ID NO:1;

(b) a second tagged amplification oligomer comprising a target hybridizing region that is from 15 to 50 nucleobases in length and contains a nucleotide sequence that is configured to specifically hybridize to all or a portion of a region of a target nucleic acid corresponding to residues 4752 to 4798 of SEQ ID NO:2;

(c) a third tagged amplification oligomer comprising a target hybridizing region that is from 15 to 50 nucleobases in length and contains a nucleotide sequence that is configured to specifically hybridize to all or a portion of a region of a target nucleic acid corresponding to residues 1954 to 2006 of SEQ ID NO:3; and (d) a fourth tagged amplification oligomer comprising a target hybridizing region that is from 15 to 50 nucleobases in length and contains a nucleotide sequence that is configured to specifically hybridize to all or a portion of a region of a target nucleic acid corresponding to residues 1994 to 2036 of SEQ ID NO:4.

* * * * *